US008003655B2

(12) United States Patent
Hartung et al.

(10) Patent No.: US 8,003,655 B2
(45) Date of Patent: Aug. 23, 2011

(54) SUBSTITUTED SULPHOXIMINES AS TIE2 INHIBITORS AND SALTS THEREOF, PHARMACEUTICAL COMPOSITIONS COMPRISING SAME, METHODS OF PREPARING SAME AND USES OF SAME

(75) Inventors: Ingo Hartung, Berlin (DE); Georg Kettschau, Berlin (DE); Hans Briem, Bremen (DE); Karl-Heinz Thierauch, Berlin (DE); Ulrich Luecking, Berlin (DE); Ulf Boemer, Glienicke/Nordbahn (DE); Martin Krueger, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1045 days.

(21) Appl. No.: 11/776,231

(22) Filed: Jul. 11, 2007

(65) Prior Publication Data

US 2008/0064696 A1 Mar. 13, 2008

Related U.S. Application Data

(60) Provisional application No. 60/831,197, filed on Jul. 17, 2006.

(30) Foreign Application Priority Data

Jul. 12, 2006 (EP) .................... 06090121

(51) Int. Cl.
C07D 439/02 (2006.01)
C07D 239/42 (2006.01)
A01N 43/54 (2006.01)
(52) U.S. Cl. ........................ 514/256; 544/332
(58) Field of Classification Search .................. 544/242, 544/322, 330, 332; 514/256
See application file for complete search history.

(56) References Cited

U.S. PATENT DOCUMENTS

2004/0102630 A1 5/2004 Brumby et al.

FOREIGN PATENT DOCUMENTS

WO WO 02/096888 A1 12/2002
WO WO 03/066601 A1 8/2003
WO WO 2005/037800 A1 4/2005

OTHER PUBLICATIONS

Pinedo et al., "Translational Research . . .", The Oncologist 2000,, 5 (suppl1): 1-2 (www.The Oncologist.com).*
McMahon, Gerald, "VEGF Receptor Signaling in Tumor Angiogenesis", The Oncologist 2000; 5(suppl 1): 3-10 (www.The Oncologist.com).*
Vippagunta et al., "Crystalline Solids", Adv. Drug Del. Rev., 48 (2001) 3-26.*

* cited by examiner

Primary Examiner — Paul V. Ward
(74) Attorney, Agent, or Firm — Millen, White, Zelano & Branigan, P.C.

(57) ABSTRACT

The invention relates to substituted sulphoximines according to the general formula (I):

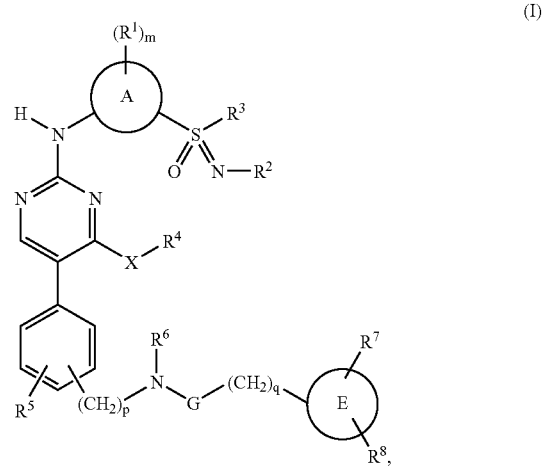

in which A, E, G, X, $R^1$, $R^2$, $R^3$, $R^4$, $R^5$, $R^6$, $R^7$, $R^8$, m, p, q, are given in the claims, and salts thereof, to pharmaceutical compositions comprising said substituted sulphoximines, to methods of preparing said substituted sulphoximines as well as the use thereof for manufacturing a pharmaceutical composition for the treatment of diseases of dysregulated vascular growth or of diseases which are accompanied with dysregulated vascular growth, wherein the compounds effectively interfere with Tie2 signalling.

23 Claims, No Drawings

SUBSTITUTED SULPHOXIMINES AS TIE2 INHIBITORS AND SALTS THEREOF, PHARMACEUTICAL COMPOSITIONS COMPRISING SAME, METHODS OF PREPARING SAME AND USES OF SAME

This application claims the benefit of the filing date of U.S. Provisional Application Ser. No. 60/831,197 filed Jul. 17, 2006, which is incorporated by reference herein.

The present invention relates to substituted sulphoximines of general formula (I) infra and salts thereof, to pharmaceutical compositions comprising said substituted sulphoximines, to methods of preparing said substituted sulphoximines, as well as to uses thereof.

SCIENTIFIC BACKGROUND

Dysregulated vascular growth plays a critical role in a variety of inflammatory diseases, in particular psoriasis, delayed type hypersensitivity, contact dermatitis, asthma, multiple sclerosis, restenosis, rheumatoid arthritis and inflammatory bowl disease. Aberrant vascular growth is also involved in neovascular ocular diseases such as age-related macular degeneration and diabetic retinopathy. Additionally, sustained vascular growth is accepted as one hallmark of cancer development (Hanahan, D.; Weinberg, R. A. *Cell* 2000, 100, 57). While tumours initially grow either as an avascular mass or by co-opting existing host vessels, growth beyond a few $mm^3$ in size is depending on the induction of vessel neogrowth in order to sufficiently provide the tumour with oxygen and nutrients. Induction of angiogenesis is a prerequisite that the tumour surpasses a certain size (the so called angiogenic switch). An intricate signalling interaction network between cancer cells and the tumour microenvironment triggers the induction of vessel growth from existing vasculature. The dependence of tumours on neovascularization has led to a new treatment paradigm in cancer therapy (Ferrara et al. *Nature* 2005, 438, 967; Carmeliet *Nature* 2005, 438, 932). Blocking tumour neovascularization by small molecule or antibody-mediated inhibition of relevant signal transduction pathways holds a great promise for extending currently available therapy options.

The development of the cardiovascular system involves two basic stages. In the initial vasculogenesis stage, which only occurs during embryonic development, angioblasts differentiate into endothelial cells which subsequently form a primitive vessel network. The subsequent stage, termed angiogenesis, involves the remodelling of the initial vasculature and sprouting of new vessels (Risau, W. *Nature* 1997, 386, 671; Jain, R. K. *Nat. Med.* 2003, 9, 685). Physiologically, angiogenesis occurs in wound healing, muscle growth, the female cycle and in the above mentioned disease states.

It has been found that receptor tyrosine kinases of the vascular endothelial growth factor (VEGF) family and the Tie (tyrosine kinase with immunoglobulin and epidermal growth factor homology domain) receptor tyrosine kinases are essential for both developmental and disease-associated angiogenesis (Ferrara et al *Nat. Med.* 2003, 9, 669; Dumont et al. *Genes Dev.* 1994, 8, 1897; Sato et al. *Nature* 1995, 376, 70).

In adults the Tie2 receptor tyrosine kinase is selectively expressed on endothelial cells (EC) of the adult vasculature (Schlaeger et al. *Proc. Nat. Acad. Sci. USA* 1997, 94, 3058). Immunohistochemical analysis demonstrated the expression of Tie2 in adult rat tissues undergoing angiogenesis. During ovarian folliculogenesis, Tie2 is expressed in neovessels of the developing corpus luteum. Four endogenous ligands—angiopoietins 1 to 4—have been identified for the type 1 transmembrane Tie2 (also named Tek) receptor, while no ligands have been identified so far for the Tie1 receptor. Binding of the extracellular Tie2 domain to the C-terminal fibrinogen-like domains of the various angiopoietins leads to significantly different cellular effects. In addition, heterodimerizations between Tie1 and Tie2 receptors have been postulated to influence ligand binding.

Binding of Ang1 to Tie2 expressed on EC induces receptor cross-phosphorylation and kinase activation thus triggering various intracellular signalling pathways. The intracellular C-terminal tail of the Tie2 protein plays a crucial role in Tie2 signalling (Shewchuk et al. *Structure* 2000, 8, 1105). Upon ligand binding, a conformational change is induced which removes the C-tail out of its inhibitory conformation thus allowing kinase activation by cross-phoshorylation of various Tyr residues in the C-tail, which subsequently function as docking sites for phosphotyrosine-binding (PTB) site possessing down-stream mediators. Cellular effects initiated by Ang1 activation of Tie2 include inhibition of EC apoptosis, stimulation of EC migration and blood vessel reorganization, suppression of inflammatory gene expression and suppression of vascular permeability (Brindle et al. *Circ. Res.* 2006, 98, 1014). In contrast to VEGF-VEGFR signalling in EC, Ang1 activation of Tie2 does not stimulate EC proliferation in the majority of published assay settings.

The anti-apoptotic effect of Tie2 signalling was shown to be mediated mainly by the PI3K-Akt signalling axis which is activated by binding of the regulatory p85 subunit of PI3K to Y1102 in the Tie2 C-tail (DeBusk et al. *Exp. Cell. Res.* 2004, 298, 167; Papapetropoulos et al. *J. Biol. Chem.* 2000, 275, 9102; Kim et al. *Circ. Res.* 2000, 86, 24). In contrast, the chemotactic response downstream of the activated Tie2 receptor requires crosstalk between PI3K and the adaptor protein Dok-R. Membrane localization of Dok-R via binding of its plekstrin homology (PH) domain to PI3K and simultaneous binding to Y1108 in the Tie2 C-tail via its PTB domain leads to Dok-R phoshorylation and downstream signalling via Nck and Pak-1 (Jones et al. *Mol. Cell. Biol.* 2003, 23, 2658; Master et al. *EMBO J.* 2001, 20, 5919). PI3K-mediated recruitment of the adaptor protein ShcA to Y1102 of the Tie2 C-tail is also believed to induce cellular sprouting and motility effects involving activation of endothelial nitric oxide synthase (eNOS), focal adhesion kinase (FAK) and the GTPases RhoA and Rac1. Other downstream mediators of Tie2 signalling include the adaptor protein Grb2, which mediates Erk1/2 stimulation, and the SHP-2 phosphatase.

In conclusion, basal activation of the Tie2 pathway by Ang1 is believed to maintain quiescence and integrity of the endothelium of the adult vasculature by providing a cell survival signal for ECs and by maintaining the integrity of the EC lining of blood vessels (Peters et al. *Recent Prog. Horm. Res.* 2004, 59, 51).

In contrast to Ang1, Ang2 is not able to activate Tie2 on EC unless Ang2 is present in high concentration or for prolonged periods. However, Ang2 functions as a Tie2 agonist in non-endothelial cells transfected with Tie2. The structural basis for this context-dependence of the Ang2-Tie2 interaction is to date not understood.

In endothelial cells, however, Ang2 functions as Tie2 antagonist and thus blocks the agonistic activity of Ang1 (Maisonpierre et al. *Science* 1997, 277, 55). Ang2 binding to Tie2 prevents Ang1-mediated Tie2 activation which leads to vessel destabilization and results in vessel regression in the absence of pro-angiogenic stimuli such as VEGF. While Ang1 is widely expressed by periendothelial cells in quiescent vasculature such as pericytes or smooth muscle cells, Ang2 expression occurs in areas of ongoing angiogenesis.

Ang2 can be stored in Weibel-Palade bodies in the cytoplasm of EC allowing for a quick vascular response upon stimulation.

Ang1 and Ang2 are expressed in the corpus luteum, with Ang2 localizing to the leading edge of proliferating vessels and Ang1 localizing diffusively behind the leading edge. Ang2 expression is inter alia initiated by hypoxia (Pichiule et al. *J. Biol. Chem.* 2004, 279, 12171). Ang2 is upregulated in the tumour vasculature and represents one of the earliest tumour markers. In the hypoxic tumour tissue, Ang2 expression induces vessel permeability and—in the presence of e.g. pro-angiogenic VEGF—triggers angiogenesis. After VEGF mediated EC proliferation and vessel sprouting maturation of the newly formed vessels again necessitates Tie2 activation by Ang1. Therefore, a subtle balancing of Tie2 activity plays a pivotal role in the early as well as late stages of neovascularization. These observations render the Tie2 RTK an attractive target for anti-angiogenesis therapy in diseases caused by or associated with dysregulated vascular growth. However, it remains to be shown if targeting the Tie2 pathway alone will be sufficient to achieve efficacious blockade of neovascularization. In certain diseases or disease subtypes it might be necessary or more efficacious to block several angiogenesis-relevant signalling pathways simultaneously.

Various theories have been discussed to explain the differential effects of Ang1 and Ang2 on Tie2 downstream signalling events. Binding of Ang1 and Ang2 in a structurally different manner to the Tie2 ectodomain could induce ligand-specific conformational changes of the intracellular kinase domain explaining different cellular effects. Mutational studies however point toward similar binding sites of Ang1 and Ang2. In contrast, various publications have focussed on different oligomerization states of Ang1 vs. Ang2 as basis for different receptor multimerization states upon ligand binding. Only Ang1 present in its tetramer or higher-order structure initiates Tie2 activation in EC while Ang2 was reported to exist as a homodimer in its native state (Kim et al. *J. Biol. Chem.* 2005, 280, 20126; Davis et al. *Nat. Struc. Biol.* 2003, 10, 38; Barton et al. *Structure* 2005, 13, 825). Finally, specific interactions of Ang1 or Ang2 with additional cell-specific co-receptors could be responsible for the different cellular effects of Ang1 vs. Ang2 binding to Tie2. Interaction of Ang1 with integrin α5β1 has been reported to be essential for certain cellular effects (Carlson et al. *J. Biol. Chem.* 2001, 276, 26516; Dallabrida et al. *Circ. Res.* 2005, 96, e8). Integrin α5β1 associates constitutively with Tie2 and increases the receptor's binding affinity for Ang1 resulting in initiation of downstream signalling at lower Ang1 effector concentrations in situations where integrin α5β1 is present. The recently solved crystal structure of the Tie2-Ang2 complex suggests however that neither the oligomerization state nor a different binding mode causes the opposing cellular effects (Barton et al. *Nat. Struc. Mol. Biol.* 2006, 13, 524).

Ang1-Tie2 signalling plays also a role in the development of the lymphatic system and in lymphatic maintenance and sprouting (Tammela et al. *Blood* 2005, 105, 4642). An intimate cross-talk between Tie2 and VEGFR-3 signalling in lymphangiogenesis seems to equal the Tie2-KDR cross-talk in blood vessel angiogenesis.

A multitude of studies have underscored the functional significance of Tie2 signalling in the development and maintenance of the vasculature. Disruption of Tie2 function in Tie2$^{-/-}$ transgenic mice leads to early embryonic lethality between days 9.5 and 12.5 as a consequence of vascular abnormalities. Tie2$^{-/-}$ embryos fail to develop the normal vessel hierarchy suggesting a failure of vascular branching and differentiation. The heart and vessels in Tie2$^{-/-}$ embryos show a decreased lining of EC and a loosened interaction between EC and underlying pericyte/smooth muscle cell matrix. Mice lacking functional Ang1 expression and mice overexpressing Ang2 display a phenotype reminiscent of the phenotype of Tie2$^{-/-}$ mice (Suri et al. *Cell* 1996, 87, 1171). Ang2$^{-/-}$ mice have profound defects in the growth and patterning of lymphatic vasculature and fail to remodel and regress the hyaloid vasculature of the neonatal lens (Gale et al. *Dev. Cell* 2002, 3, 411). Ang1 rescued the lymphatic defects, but not the vascular remodelling defects. Therefore, Ang2 might function as a Tie2 antagonist in blood vasculature but as a Tie2 agonist in developing lymph vasculature suggesting redundant roles of Ang1 and Ang2 in lymphatic development.

Aberrant activation of the Tie2 pathway is involved in various pathological settings. Activating Tie2 mutations leading to increased ligand-dependent and ligand-independent Tie2 kinase activity cause inherited venous malformations (Vikkula et al. *Cell* 1996, 87, 1181). Increased Ang1 mRNA and protein levels as well as increased Tie2 activation have been reported in patients with pulmonary hypertension (PH). Increased pulmonary arterial pressure in PH patients results from increased coverage of pulmonary arterioles with smooth muscle cells (Sullivan et al. *Proc. Natl. Acad. Sci. USA* 2003, 100, 12331). In chronic inflammatory diseases, like in psoriasis, Tie2 and the ligands Ang1 and Ang2 are greatly upregulated in lesions, whereas a significant decrease in expression of Tie2 and ligands occur under anti-psoriatic treatment (Kuroda et al. *J. Invest. Dermatol* 2001, 116, 713). Direct association of pathogenesis of disease with Tie2 expression has been demonstrated recently in transgenic mice overexpressing Tie2 (Voskas et al. *Am. J. Pathol.* 2005, 166, 843). In these mice overexpression of Tie2 causes a psoriasis-like phenotype (such as epidermal thickening, rete ridges and lymphocyte infiltration). These skin abnormalities are resolved completely upon suppression of transgene expression, thereby illustrating a complete dependence on Tie2 signalling for disease maintenance and progression. A recent study underscored the connection of the Ang1/Ang2-Tie2 signalling axis to the induction of inflammation (Fiedler et al. *Nat. Med.* 2006, 12, 235). Inhibition of the Tie2 signalling pathway is therefore expected to be useful in the therapy of a broad range of inflammatory diseases.

Tie2 expression was investigated in human breast cancer specimens and Tie2 expression was found in the vascular endothelium both in normal breast tissue as well as in tumour tissue. The proportion of Tie2-positive microvessels was increased in tumours as compared to normal breast tissue (Peters et al. *Br. J. Canc.* 1998, 77, 51). However, significant heterogeneity in endothelial Tie2 expression was observed in clinical specimen from a variety of human cancers (Fathers et al. *Am. J. Path.* 2005, 167, 1753). In contrast, Tie2 and angiopoietins were found to be highly expressed in the cytoplasm of human colorectal adenocarcinoma cells indicating at the potential presence of an autocrine/paracrine growth loop in certain cancers (Nakayama et al. *World J. Gastroenterol.* 2005, 11, 964). A similar autocrine/paracrine Ang1-Ang2-Tie2 loop was postulated for certain human gastric cancer cell lines (Wang et al. *Biochem. Biophys. Res. Comm.* 2005, 337, 386).

The relevance of the Ang1-Tie2 signalling axis was challenged with various biochemical techniques. Inhibition of Ang1 expression by an antisense RNA approach resulted in decreased xenograft tumour growth (Shim et al. *Int. J. Canc.* 2001, 94, 6; Shim et al. *Exp. Cell Research* 2002, 279, 299). However, other studies report that experimental overexpression of Ang1 in tumour models leads to decreased tumour growth (Hayes et al. *Br. J. Canc.* 2000, 83, 1154; Hawighorst et al. *Am. J. Pathol.* 2002, 160, 1381; Stoeltzing et al. *Cancer Res.* 2003, 63, 3370). The latter results can be rationalized by the ligand's ability to stabilize the endothelial lining of vessels rendering vessels less sensitive for angiogenic stimuli. Interference with the dynamics of Ang1-Tie2 signalling either by over-stimulation or by stimulus deprivation seemingly leads to similar phenotypes.

The pharmacological relevance of inhibiting Tie2 signalling was tested applying various non-small molecule approaches. A peptidic inhibitor of Ang1/2 binding to Tie2 was shown to inhibit Ang1-induced HUVEC migration and angiogenesis induction in an in vivo model (Tournaire et al. *EMBO Rep.* 2005, 5, 1). Corneal angiogenesis induced by tumour cell conditioned medium was inhibited by a recombinant soluble Tie2 receptor (sTie2) despite the presence of VEGF (Lin et al. *J. Clin. Invest.* 1997, 100, 2072; see also Singh et al. *Biochem. Biophys. Res. Comm.* 2005, 332, 194). Gene therapy by adenoviral vector delivered sTie2 was capable of reducing tumour growth rates of a murine mammary carcinoma and a murine melanoma and resulted in reduction of metastasis formation (Lin et al. *Proc. Natl. Acad. Sci. USA* 1998, 95, 8829). Similar effects were observed with related sTie2 constructs (Siemeister et al. *Cancer Res.* 1999, 59, 3185) and a Tek-Fc construct (Fathers et al. *Am. J. Path.* 2005, 167, 1753).

Adenovirus-delivered anti-Tie2 intrabodies were shown to inhibit growth of a human Kaposi's sarcoma and a human colon carcinoma upon peritumoural administration (Popkov et al. *Cancer Res.* 2005, 65, 972). Histopathological analysis revealed a marked decrease in vessel density in treated vs. control tumours. Phenotypic simultaneous knockout of KDR and Tie2 by an adenovirus delivered intradiabody resulted in significantly higher growth inhibition of a human melanoma xenograft model than KDR knockout alone (Jendreyko et al. *Proc. Natl. Acad. Sci. USA* 2005, 102, 8293). Similarly, the bispecific Tie2-KDR intradiabody was more active in an in vitro EC tube formation inhibition assay than the two monospecific intrabodies alone (Jendreyko et al. *J. Biol. Chem.* 2003, 278, 47812). Systematic treatment of tumour-bearing mice with Ang2-blocking antibodies and peptide-Fc fusion proteins led to tumour stasis and elimination of tumour burden in a subset of animals (Oliner et al. *Cancer Cell* 2004, 6, 507). For a recent report on an immunization approach, see Luo et al. *Clin. Cancer Res.* 2006, 12, 1813.

However, from the above studies using biochemical techniques to interfere with Tie2 signalling it is not clear, whether similar phenotypes will be observed with small molecule inhibitors of the Tie2 kinase activity. Small molecule inhibitors of kinases by definition block only those cellular effects which are mediated by the receptor's kinase activity and not those which might involve the kinase only as a co-receptor or scaffolding component in multi-enzyme complexes. So far, studies describing in vivo pharmacodynamic effects of small molecule Tie2 inhibitors are rare (Scharpfenecker et al. *J. Cell Sci.* 2005, 118, 771; J. M. Chen, *Medicinal Chemistry and High Speed Synthesis—The Tie-2 story*; presentation held at the Centennial AACR, April 2007, Los Angeles, U.S.A.) It remains to be shown that small molecule inhibitors of the Tie2 kinase will be as efficacious in inhibiting angiogenesis as e.g. ligand antibodies, soluble decoy receptors or receptor intrabodies. As discussed above, in certain settings inhibition of Tie2 signalling alone might not be sufficient to induce an adequate antiangiogenic effect. Simultaneous inhibition of several angiogenesis relevant signalling pathways could overcome such inadequacies. In conclusion, there is a great need for novel chemotypes for small molecule inhibitors of the Tie2 kinase. Fine tuning of additive anti-angiogenic activities as well as pharmacokinetic parameters such as e.g. solubility, membrane permeability, tissue distribution and metabolism will finally allow for chosing compounds of accurate profiles for various diseases caused by or associated with dysregulated vascular growth.

PRIOR ART

To date, a small number of therapeutic agents with antiangiogenic activity have been approved for cancer treatment. Avastin (Bevacizumab), a VEGF neutralizing antibody, blocks KDR and VEGFR1 signalling and has been approved for first-line treatment of metastatic colorectal cancer. The small molecule multi-targeted kinase inhibitor Nexavar (Sorafenib) inhibits inter alia members of the VEGFR family and has been approved for the treatment of advanced renal cell carcinoma. Sutent (Sunitinib), another multi-targeted kinase inhibitor with activity vs. VEGFR family members, has been approved by the FDA for treatment of patients with gastrointestinal stromal tumours (GIST) or advanced kidney tumours. Several other small molecule inhibitors of angiogenesis-relevant targets are in clinical and pre-clinical development. AMG-386, an angiopoietin-targeting recombinant Fc fusion protein, is in phase I clinical development in patients with advanced solid tumours. Several multi-targeted small molecule inhibitors with activity against Tie2 are (or have been) in preclinical evaluation for cancer therapy, including ABT-869, CE-245677, GW697465A and A-422885.88 (BSF466895). The first compound, however, was reported to possess higher inhibitory activity against other kinase targets including non-angiogenesis kinases and oncogenic kinases. This agent is therefore not considered to be a purely antiangiogenic agent and its applicability to non-cancer diseases remains to be shown.

Pyrimidines and their derivatives have been frequently described as therapeutic agents for diverse diseases. Various recently published patent applications describe their use as inhibitors of protein kinases, for example in WO2001064654 and WO 2002096888 for use as CDK inhibitors, in WO 2003032997 for use as CDK and Aurora A kinase inhibitors, in WO 2003063794 for use as Syk kinase inhibitors, in WO 2003078404 for use as ZAP-70 and/or Syk or FAK kinase inhibitors, in WO 2004074244 for use as PLK inhibitors, in WO 2005026158 as ZAP-70 and/or Syk kinase inhibitors, and in WO 2005026130 as Alk inhibitors.

More specifically, certain 2,4-diaminosubstituted pyrimidine derivatives have been disclosed as inhibitors of protein kinases involved in angiogenesis, such as VEGFR-2 (KDR) and/or Tie2 kinase, for example benzimidazole substituted 2,4-diaminopyrimidines (WO 2003074515) or bis-2,4-anilino-pyrimidines (WO 2003066601).

Incorporation of pyrimidines into a bicyclic structure has been reported to provide compounds with Tie2/VEGFR-2 dual inhibitory activity (WO 2003022582). Pyrimidine derivatives in which the pyrimidine constitutes a part of a macrocyclic ring system have been reported to be inhibitors of CDKs and/or VEGFRs (WO 2004026881), or of CDK2 and/or CDK5, respectively (WO 2004078682). Very recently, macrocycles containing a pyrimidine have been disclosed as inhibitors of Tie2 (WO 2006066956 and WO 2006066957 (EP 1674469 and EP 1674470)). Sulfoximine substituted pyrimidines have been disclosed very recently (WO2005037800) as potent inhibitors of CDK and VEGFR.

TECHNICAL PROBLEM TO BE SOLVED

Despite the fact that various inhibitors of Tie2 and other kinases involved in angiogenesis are known, there remains a well recognised need for novel chemotypes of Tie2 kinase inhibitors to be used for the treatment of oncological and/or non-oncological disorders which offer one or more advantages over the compounds known from prior art, such as:
- improved activity and/or efficacy
- beneficial kinase selectivity profile according to the respective therapeutic need
- improved side effect profile, such as fewer undesired side effects, lower intensity of side effects, or reduced (cyto) toxicity
- improved physicochemical properties, such as solubility in water and body fluids
- improved pharmacokinetic properties, allowing e.g. for dose reduction or an easier dosing scheme
- easier drug substance manufacturing e.g. by shorter synthetic routes or easier purification.

DESCRIPTION OF THE INVENTION

Surprisingly, it has been found that the novel technical problem set forth above has been solved in an unexpected manner by the inventors by providing a novel chemotype for potent inhibitors of the endothelial cell specific receptor tyrosine kinase Tie2. In addition to being potent Tie2 inhibitors, compounds of the present invention were surprisingly found to possess significantly lower potency as inhibitors of CDK2.

Hence, the invention relates to compounds of the general Formula I:

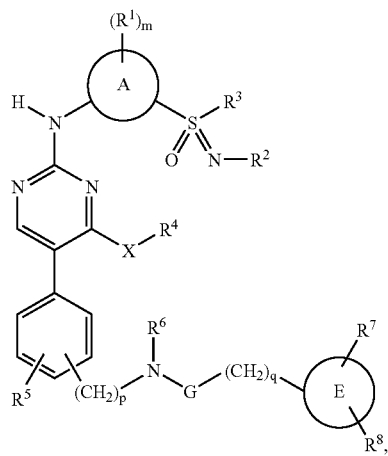

(I)

in which

A and E are the same or different and are selected, independently from each other, from the group consisting of phenylene and a five- or six-membered heteroarylene;

G is selected from the group comprising, preferably consisting of, $-C(O)NR^9-$, $-S(O)_2-$, and $-C(O)-Y-$;

X is selected from the group comprising, preferably consisting of $-O-$, $-S-$, and $-NR^{10}-$;

Y is selected from the group comprising, preferably consisting of $-C_1-C_6$-alkylene and $-C_3-C_8$-cycloalkylene;

$R^1$ is selected from the group comprising, preferably consisting of, hydrogen, halogen, nitro, cyano, $-C_1-C_6$-alkyl, $-(CH_2)_nOR^{11}$, $-(CH_2)_nNR^{11}R^{12}$, $-(CH_2)_nC(O)R^{13}$, $-(CH_2)_nNHC(O)R^{13}$, $-(CH_2)_nNHC(O)NR^{11}R^{12}$, $-(CH_2)_nNHS(O)_2R^{14}$, and $-(CH_2)_nC(O)NR^{11}R^{12}$;

$R^2$ represents hydrogen, $-C(O)R^{13a}$, $-S(O)_2R^{14a}$, or $-S(O)_2-(CH_2)_r-Si(R^{15}R^{16}R^{17})$, or is selected from a group comprising, preferably consisting of $-C_1-C_6$-alkyl, $-C_2-C_6$-alkenyl, $-C_2-C_6$-alkynyl, $-C_3-C_{10}$-cycloalkyl, $-C_3-C_{10}$-heterocycloalkyl, $-(CH_2)_s$-aryl and $-(CH_2)_s$-heteroaryl, wherein said residues are unsubstituted or substituted one or more times independently from each other with halogen, nitro, cyano, $-C_1-C_6$-alkyl, $-OR^{11a}$, $-NR^{11a}R^{12a}$, $-C_1-C_6$-haloalkyl, $-C(O)R^{13a}$, or $-S(O)_2R^{14a}$;

$R^3$ is selected from a group comprising, preferably consisting of $-C_1-C_6$-alkyl, $-C_2-C_6$-alkenyl, $-C_2-C_6$-alkynyl, $-C_3-C_{10}$-cycloalkyl, $-(CH_2)_t$-aryl and $-(CH_2)_t$-heteroaryl, wherein said residues are unsubstituted or substituted one or more times independently from each other with halogen, nitro, cyano, $-C_1-C_6$-alkyl, $-OR^{11b}$, $-NR^{11b}R^{12b}$, $-C_1-C_6$-haloalkyl, $-C(O)R^{13b}$, or $-S(O)_2R^{14b}$;

$R^4$ is selected from a group comprising, preferably consisting of $-C_1-C_6$-alkyl, $-C_2-C_6$-alkenyl, $-C_2-C_6$-alkynyl, $-C_3-C_{10}$-cycloalkyl, $-C_3-C_{10}$-heterocycloalkyl, $-(CH_2)_u$-aryl and $-(CH_2)_u$-heteroaryl, wherein said residues are unsubstituted or substituted one or more times independently from each other with halogen, nitro, cyano, $-C_1-C_6$-alkyl, $-C_3-C_{10}$-cycloalkyl, $-C_3-C_{10}$-heterocycloalkyl, $-OR^{11c}$, $-NR^{11c}R^{12c}$, $-C_1-C_6$-haloalkyl, $-C(O)R^{13c}$, or $-S(O)_2R^{14c}$;

$R^5$ is selected from the group comprising, preferably consisting of, hydrogen, halogen, nitro, cyano, $-C_1-C_6$-alkyl, $-OR^{11d}$, $-NR^{11d}R^{12d}$, $-C_1-C_6$-haloalkyl, $-C_1-C_6$-alkylthio and $-C_1-C_6$-alkylcarbonyl;

$R^6$ is hydrogen or $-C_1-C_6$-alkyl;

$R^7$, $R^8$ are the same or different, independently selected from each other, from the group comprising, preferably consisting of hydrogen, halogen, nitro, cyano, $-(CH_2)_vOR^{11e}$, $(CH_2)_vNR^{11e}R^{12e}$, $-C_1-C_6$-alkyl, $-C_3-C_{10}$-cycloalkyl, $-C_3-C_{10}$-heterocycloalkyl, $-C_1-C_6$-haloalkyl, $-C_1-C_6$-alkylthio, $-(CH_2)_vC(O)R^{13e}$, $-(CH_2)_vC(O)NR^{11e}R^{12e}$ and $-(CH_2)_vS(O)_2NR^{11e}R^{12e}$;

$R^9$ and $R^{10}$ are the same or different, independently selected from each other, from the group comprising, preferably consisting of hydrogen and $-C_1-C_6$-alkyl;

$R^{11}$, $R^{11a}$,
$R^{11b}$, $R^{11c}$,
$R^{11d}$, $R^{11e}$,
$R^{11f}$, $R^{11g}$,
$R^{12}$, $R^{12a}$,
$R^{12b}$, $R^{12c}$,
$R^{12d}$, $R^{12e}$,
$R^{12f}$ independently from each other represent hydrogen, $-C(O)R^{13f}$, or $-S(O)_2R^{14f}$, or are selected from the group comprising, preferably consisting of, $-C_1-C_6$-alkyl, $-C_1-C_6$-alkoxy, $-C_2-C_6$-alkenyl, $-C_2-C_6$-alkynyl, $-C_3-C_{10}$-cycloalkyl, $-C_3-C_{10}$-heterocycloalkyl, $-(CH_2)_x$-aryl and $-(CH_2)_x$-heteroaryl, wherein said residues of $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are unsubstituted or substituted one or more times independently from each other with halogen, nitro, cyano, $-C_1-C_6$-alkyl, $-OR^{11f}$, $-NR^{11f}R^{12f}$, $-C_1-C_6$-haloalkyl, $-C_1-C_6$-haloalkoxy, $-C_1-C_6$-alkylthio, $-C(O)OR^{18}$, $-C(O)NR^{18}R^{18a}$, or $-S(O)_2NR^{18}R^{18a}$; and wherein said residues of $R^{11f}$, $R^{12f}$ are unsubstituted or substituted one or more times independently from each other with halogen, nitro, cyano, $-C_1-C_6$-alkyl, $-C_1-C_6$-haloalkyl, $-C_1-C_6$-haloalkoxy, $-C_1-C_6$-alkylthio, $-C(O)OR^{18}$, $-C(O)NR^{18}R^{18a}$, or $-S(O)_2NR^{18}R^{18a}$, or substituted one time with $-OR^{11f}$ or $-NR^{11f}R^{12f}$; or $R^{11}$ and $R^{12}$,
$R^{11a}$ and $R^{12a}$, $R^{11b}$ and $R^{12b}$,
$R^{11c}$ and $R^{12c}$,
$R^{11d}$ and $R^{12d}$,
$R^{11e}$ and $R^{12e}$,
and
$R^{12f}$ and $R^{12f}$ independently from each other, together with the nitrogen atom to which they are attached in groups —$NR^{11}R^{12}$, —$NR^{11a}R^{12a}$, —$NR^{11b}R^{12b}$, —$NR^{11c}R^{12c}$, —$NR^{11d}R^{12d}$, $NR^{11e}R^{12e}$, and —$NR^{11f}R^{12f}$ form a 3 to 10 membered heterocycloalkyl ring, wherein the carbon backbone of this heterocycloalkyl ring is optionally interrupted one or more times, the same way or differently, by a member of the group comprising, preferably consisting of, —$NR^{11g}$—, —O—, —S—, —C(O)—, —S(O)—, and —$S(O)_2$—, and optionally contains one or more double bonds;

$R^{13}$, $R^{13a}$,
$R^{13b}$, $R^{13c}$,
$R^{13e}$,
and $R^{13f}$ independently from each other represent hydrogen, hydroxy or —$NR^{19}R^{20}$, or are, independently from each other, selected from a group comprising, preferably consisting of, —$C_1$-$C_6$-alkyl, —$C_1$-$C_6$-alkoxy, —$C_3$-$C_{10}$-cycloalkyl and —$C_3$-$C_{10}$-heterocycloalkyl, wherein said residues are unsubstituted or substituted one or more times independently from each other with halogen, nitro, cyano, —$C_1$-$C_6$-alkyl, —$C_1$-$C_6$-haloalkyl, aryl, or heteroaryl, wherein aryl or heteroaryl are unsubstituted or substituted one or more times with halogen, nitro, cyano, —$C_1$-$C_6$-alkyl, —$C_1$-$C_6$-alkoxy, —$C_1$-$C_6$-haloalkyl, or —$C_1$-$C_6$-haloalkoxy;

$R^{14}$, $R^{14a}$,
$R^{14b}$, $R^{14c}$,
and $R^{14f}$ independently from each other represent hydrogen or —$NR^{19a}R^{20a}$, or are, independently from each other, selected from a group comprising, preferably consisting of, —$C_1$-$C_6$-alkyl, —$C_3$-$C_{10}$-cycloalkyl and —$C_3$-$C_{10}$-heterocycloalkyl, wherein said residues are unsubstituted or substituted one or more times independently from each other with halogen, nitro, cyano, —$C_1$-$C_6$-alkyl, —$C_1$-$C_6$-haloalkyl, aryl, or heteroaryl, wherein aryl or heteroaryl are unsubstituted or substituted one or more times with halogen, nitro, cyano, —$C_1$-$C_6$-alkyl, —$C_1$-$C_6$-alkoxy, —$C_1$-$C_6$-haloalkyl, or —$C_1$-$C_6$-haloalkoxy;

$R^{15}$, $R^{16}$,
and $R^{17}$ independently from each other represent —$C_1$-$C_6$-alkyl or phenyl;

$R^{18}$ and $R^{18a}$, independently from each other represent hydrogen, or are selected from the group comprising, preferably consisting of, —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{10}$-heterocycloalkyl, —$(CH_2)_y$-aryl and —$(CH_2)_y$-heteroaryl, wherein said residues are unsubstituted or substituted one or more times independently from each other with halogen, nitro, cyano, —$C_1$-$C_6$-alkyl, or —$C_1$-$C_6$-haloalkyl; or $R^{18}$ and $R^{18a}$, together with the nitrogen atom to which they are attached form a 3 to 10 membered heterocycloalkyl ring, wherein the carbon backbone of this heterocycloalkyl ring is optionally interrupted one or more times, the same way or differently, by a member of the group comprising, preferably consisting of, —$NR^{11g}$—, —O—, —S—, —C(O)—, —S(O)—, and —$S(O)_2$—, and optionally contains one or more double bonds;

$R^{19}$, $R^{19a}$,
$R^{20}$,
and $R^{20a}$ independently from each other represent hydrogen, —$C_1$-$C_6$-alkyl or —$(CH_2)_z$-phenyl;

m and r independently from each other represent an integer of 1 or 2;

n, p, q,
r, s, t,
u, v, x,
y and z independently from each other represent an integer of 0, 1, 2, 3 or 4, wherein when m represents an integer of 2, said substituents $R^1$ are independent of each other;

or a salt, N-oxide, solvate, or in vivo hydroysable ester thereof.

In accordance with a preferred embodiment, the present invention relates to compounds of general formula I, supra, in which:

A and E are the same or different and are selected, independently from each other, from the group consisting of phenylene and a five- or six-membered heteroarylene;

G is selected from the group comprising, preferably consisting of, —C(O)$NR^9$—, —$S(O)_2$—, and —C(O)—Y—;

X is selected from the group comprising, preferably consisting of —O—, —S—, and —$NR^{10}$—;

Y is selected from the group comprising, preferably consisting of —$C_1$-$C_6$-alkylene and —$C_3$-$C_8$-cycloalkylene;

$R^1$ is selected from the group comprising, preferably consisting of, hydrogen, halogen, nitro, cyano, —$C_1$-$C_6$-alkyl, —$(CH_2)_n OR^{11}$, —$(CH_2)_n NHC(O)R^{13}$, —$(CH_2)_n NHC(O)NR^{11}R^{12}$, and —$(CH_2)_n NHS(O)_2 R^{14}$;

$R^2$ represents hydrogen, —C(O)$R^{13a}$, —$S(O)_2 R^{14a}$, or —$S(O)_2$—$(CH_2)_r$—Si($R^{15}R^{16}R^{17}$), or is selected from a group comprising, preferably consisting of —$C_1$-$C_6$-alkyl, —$C_3$-$C_{10}$-cycloalkyl, and —$(CH_2)_s$-aryl, wherein said residues are unsubstituted or substituted one or more times independently from each other with halogen, nitro, cyano, —$C_1$-$C_6$-alkyl, —$OR^{11a}$, —$NR^{11a}R^{12a}$, —$C_1$-$C_6$-haloalkyl, —C(O)$R^{13a}$, or —$S(O)_2 R^{14a}$;

$R^3$ is selected from a group comprising, preferably consisting of —$C_1$-$C_6$-alkyl, —$C_3$-$C_{10}$-cycloalkyl, and —$(CH_2)_t$-aryl, wherein said residues are unsubstituted or substituted one or more times independently from each other with halogen, nitro, cyano, —$C_1$-$C_6$-alkyl, —$OR^{11b}$, —$NR^{11b}R^{12b}$, —$C_1$-$C_6$-haloalkyl, —C(O)$R^{13b}$, or —$S(O)_2 R^{14b}$;

$R^4$ is selected from a group comprising, preferably consisting of —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{10}$-heterocycloalkyl, —$(CH_2)_u$-aryl and —$(CH_2)_u$-heteroaryl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, —$OR^{11c}$, —$NR^{11c}R^{12c}$, —$C_1$-$C_6$-haloalkyl, —C(O)$R^{13c}$, or —$S(O)_2 R^{14c}$;

$R^5$ is selected from the group comprising, preferably consisting of, hydrogen, halogen, —$C_1$-$C_6$-alkyl, —$OR^{11d}$, and —$NR^{11d}R^{12d}$;

$R^6$ is hydrogen or —$C_1$-$C_6$-alkyl;

$R^7$, $R^8$ are the same or different, independently selected from each other, from the group comprising, preferably consisting of hydrogen, halogen, nitro, cyano, —$(CH_2)_v OR^{11e}$, —$(CH_2)_v NR^{11e}R^{12e}$, —$C_1$-$C_6$-alkyl, —$C_3$-$C_{10}$-cycloalkyl, —$C_3$-$C_{10}$-heterocycloalkyl, —$C_1$-$C_6$-haloalkyl, —$C_1$-$C_6$-alkylthio, —$(CH_2)_v C(O)R^{13e}$, —$(CH_2)_v C(O)NR^{11e}R^{12e}$ and —$(CH_2)_v S(O)_2 NR^{11e}R^{12e}$;

$R^9$ and $R^{10}$ are the same or different, independently selected from each other, from the group comprising, preferably consisting of hydrogen and —$C_1$-$C_6$-alkyl;

$R^{11}$, $R^{11a}$,
$R^{11b}$, $R^{11c}$, $R^{11d}$, $R^{11e}$,
$R^{11f}$, $R^{11g}$,
$R^{12}$, $R^{12a}$,
$R^{12b}$, $R^{12c}$,
$R^{12d}$, $R^{12e}$,
$R^{12f}$ independently from each other represent hydrogen, —C(O)R$^{13f}$, or —S(O)$_2$R$^{14f}$, or are selected from the group comprising, preferably consisting of, —C$_1$-C$_6$-alkyl, —C$_1$-C$_6$-alkoxy, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_x$-aryl and —(CH$_2$)$_x$-heteroaryl, wherein said residues of $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are unsubstituted or substituted one or more times independently from each other with halogen, nitro, cyano, —C$_1$-C$_6$-alkyl, —OR$^{11f}$, —NR$^{11f}$R$^{12f}$, —C$_1$-C$_6$-haloalkyl, —C$_1$-C$_6$-haloalkoxy, —C$_1$-C$_6$-alkylthio, —C(O)OR$^{18}$, —C(O)NR$^{18}$R$^{18a}$, or —S(O)$_2$NR$^{18}$R$^{18a}$; and wherein said residues of $R^{11f}$, $R^{12f}$ are unsubstituted or substituted one or more times independently from each other with halogen, nitro, cyano, —C$_1$-C$_6$-alkyl, —C$_1$-C$_6$-haloalkyl, —C$_1$-C$_6$-haloalkoxy, —C$_1$-C$_6$-alkylthio, —C(O)OR$^{18}$, —C(O)NR$^{18}$R$^{18a}$, or —S(O)$_2$NR$^{18}$R$^{18a}$, or substituted one time with —OR$^{11f}$ or —NR$^{11f}$R$^{12f}$; or $R^{11}$ and $R^{12}$,
$R^{11a}$ and $R^{12a}$,
$R^{11b}$ and $R^{12b}$,
$R^{11c}$ and $R^{12c}$,
$R^{11d}$ and $R^{12d}$,
$R^{11e}$ and $R^{12e}$,
and
$R^{12f}$ and $R^{12f}$ independently from each other, together with the nitrogen atom to which they are attached in groups —NR$^{11}$R$^{12}$, —NR$^{11a}$R$^{12a}$, —NR$^{11b}$R$^{12b}$, —NR$^{11c}$R$^{12c}$, —NR$^{11d}$R$^{12d}$, —NR$^{11e}$R$^{12e}$, and —NR$^{11f}$R$^{12f}$ form a 3 to 10 membered heterocycloalkyl ring, wherein the carbon backbone of this heterocycloalkyl ring is optionally interrupted one or more times, the same way or differently, by a member of the group comprising, preferably consisting of, —NR$^{11g}$—, —O—, —S—, —C(O)—, —S(O)—, and —S(O)$_2$—, and optionally contains one or more double bonds;

$R^{13}$, $R^{13a}$,
$R^{13b}$, $R^{13c}$,
$R^{13e}$,
and $R^{13f}$ independently from each other represent hydrogen, hydroxy or —NR$^{19}$R$^{20}$, or are, independently from each other, selected from a group comprising, preferably consisting of, —C$_1$-C$_6$-alkyl, —C$_1$-C$_6$-alkoxy, —C$_3$-C$_{10}$-cycloalkyl and —C$_3$-C$_{10}$-heterocycloalkyl, wherein said residues are unsubstituted or substituted one or more times independently from each other with halogen, nitro, cyano, —C$_1$-C$_6$-alkyl, —C$_1$-C$_6$-haloalkyl, aryl, or heteroaryl, wherein aryl or heteroaryl are unsubstituted or substituted one or more times with halogen, nitro, cyano, —C$_1$-C$_6$-alkyl, —C$_1$-C$_6$-alkoxy, —C$_1$-C$_6$-haloalkyl, or —C$_1$-C$_6$-haloalkoxy;

$R^{14}$, $R^{14a}$,
$R^{14b}$, $R^{14c}$,
and $R^{14f}$ independently from each other represent hydrogen or —NR$^{19a}$R$^{20a}$, or are, independently from each other, selected from a group comprising, preferably consisting of, —C$_1$-C$_6$-alkyl, —C$_3$-C$_{10}$-cycloalkyl and —C$_3$-C$_{10}$-heterocycloalkyl, wherein said residues are unsubstituted or substituted one or more times independently from each other with halogen, nitro, cyano, —C$_1$-C$_6$-alkyl, —C$_1$-C$_6$-haloalkyl, aryl, or heteroaryl, wherein aryl or heteroaryl are unsubstituted or substituted one or more times with halogen, nitro, cyano, —C$_1$-C$_6$-alkyl, —C$_1$-C$_6$-alkoxy, —C$_1$-C$_6$-haloalkyl, or —C$_1$-C$_6$-haloalkoxy;

$R^{15}$, $R^{16}$,
and $R^{17}$ independently from each other represent —C$_1$-C$_6$-alkyl or phenyl;

$R^{18}$ and $R^{18a}$ independently from each other represent hydrogen, or are selected from the group comprising, preferably consisting of, —C$_1$-C$_6$-alkyl, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_y$-aryl and —(CH$_2$)$_y$-heteroaryl, wherein said residues are unsubstituted or substituted one or more times independently from each other with halogen, nitro, cyano, —C$_1$-C$_6$-alkyl, or —C$_1$-C$_6$-haloalkyl; or $R^{18}$ and $R^{18a}$, together with the nitrogen atom to which they are attached form a 3 to 10 membered heterocycloalkyl ring, wherein the carbon backbone of this heterocycloalkyl ring is optionally interrupted one or more times, the same way or differently, by a member of the group comprising, preferably consisting of, —NR$^{11g}$—, —O—, —S—, —C(O)—, —S(O)—, and —S(O)$_2$—, and optionally contains one or more double bonds;

$R^{19}$, $R^{19a}$,
$R^{20}$,
and $R^{20a}$ independently from each other represent hydrogen, —C$_1$-C$_6$-alkyl or —(CH$_2$)$_z$-phenyl;

m represents an integer of 1 or 2;
r represents an integer of 2;
s and t independently from each other represent an integer of 0, 1, or 2;
n represents an integer of 0 or 1;
p, q,
u, v, x,
y and z independently from each other represent an integer of 0, 1, 2, 3 or 4,
wherein when m represents an integer of 2, said substituents $R^1$ are independent of each other.

In accordance with a more preferred embodiment, the present invention relates to compounds of general formula I, supra, in which A is phenylene;
E is selected from the group consisting of phenylene and a five- or six-membered heteroarylene;
G is selected from the group comprising, preferably consisting of, —C(O)NR$^9$—, —S(O)$_2$—, and —C(O)—Y—;
X is selected from the group comprising, preferably consisting of —O—, —S—, and —NR$^{10}$—;
Y is selected from the group comprising, preferably consisting of —C$_1$-C$_6$-alkylene and —C$_3$-C$_8$-cycloalkylene;
$R^1$ is hydrogen;
$R^2$ represents hydrogen, —C(O)R$^{13a}$, or is selected from a group comprising, preferably consisting of —C$_1$-C$_6$-alkyl, —C$_3$-C$_{10}$-cycloalkyl, and —(CH$_2$)$_s$-aryl, wherein said residues are unsubstituted or substituted one or more times independently from each other with halogen, nitro, cyano, —C$_1$-C$_6$-alkyl, —OR$^{11a}$, —NR$^{11a}$R$^{12a}$, or —C$_1$-C$_6$-haloalkyl;
$R^3$ is selected from a group comprising, preferably consisting of —C$_1$-C$_6$-alkyl, —C$_3$-C$_{10}$-cycloalkyl, and —(CH$_2$)$_t$-aryl, wherein said residues are unsubstituted or substituted one or more times independently from each other with halogen, nitro, cyano, —C$_1$-C$_6$-alkyl, —OR$^{11b}$, —NR$^{11b}$R$^{12b}$, or —C$_1$-C$_6$-haloalkyl;
$R^4$ is selected from a group comprising, preferably consisting of —C$_1$-C$_6$-alkyl, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_u$-aryl and —(CH$_2$)$_u$-heteroaryl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, —$OR^{11c}$, —$NR^{11c}R^{12c}$, —$C_1$-$C_6$-haloalkyl, —$C(O)R^{13c}$, or —$S(O)_2R^{14c}$;

$R^5$ is selected from the group comprising, preferably consisting of, hydrogen, methyl, fluoro, and chloro;

$R^6$ is hydrogen or methyl;

$R^7$, $R^8$ are the same or different, independently selected from each other, from the group comprising, preferably consisting of hydrogen, halogen, nitro, cyano, —$(CH_2)_vOR^{11e}$, —$(CH_2)_vNR^{11e}R^{12e}$, —$C_1$-$C_6$-alkyl, —$C_3$-$C_{10}$-cycloalkyl, —$C_3$-$C_{10}$-heterocycloalkyl, —$C_1$-$C_6$-haloalkyl, —$C_1$-$C_6$-alkylthio, —$(CH_2)_xC(O)R^{13e}$, —$(CH_2)_vC(O)NR^{11e}R^{12e}$ and —$(CH_2)_vS(O)_2NR^{11e}R^{12e}$;

$R^9$ is hydrogen or methyl;

$R^{10}$ is hydrogen;

$R^{11a}$, $R^{11b}$,
$R^{11c}$, $R^{11e}$,
$R^{11f}$, $R^{11g}$,
$R^{12a}$, $R^{12b}$,
$R^{12c}$, $R^{12e}$, $R^{12f}$ independently from each other represent hydrogen, —$C(O)R^{13f}$, or —$S(O)_2R^{14f}$, or are selected from the group comprising, preferably consisting of, —$C_1$-$C_6$-alkyl, —$C_3$-$C_{10}$-cycloalkyl, and —$(CH_2)_x$-aryl, wherein said residues of $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are unsubstituted or substituted one or more times independently from each other with halogen, nitro, cyano, —$C_1$-$C_6$-alkyl, —$OR^{11f}$, —$NR^{11f}R^{12f}$, —$C_1$-$C_6$-haloalkyl, or —$C_1$-$C_6$-haloalkoxy; and wherein said residues of $R^{11f}$, $R^{12f}$ are unsubstituted or substituted one or more times independently from each other with halogen, nitro, cyano, —$C_1$-$C_6$-alkyl, —$C_1$-$C_6$-haloalkyl, or —$C_1$-$C_6$-haloalkoxy, or substituted one time with —$OR^{11f}$ or —$NR^{11f}R^{12f}$; or $R^{11a}$ and $R^{12a}$,
$R^{11b}$ and $R^{12b}$,
$R^{11c}$ and $R^{12c}$,
$R^{11e}$ and $R^{12e}$,
and
$R^{12f}$ and $R^{12f}$ independently from each other, together with the nitrogen atom to which they are attached in groups —$NR^{11a}R^{12a}$, —$NR^{11b}R^{12b}$, —$NR^{11c}R^{12c}$, —$NR^{11e}R^{12e}$, and —$NR^{11f}R^{12f}$ form a 3 to 7 membered heterocycloalkyl ring, wherein the carbon backbone of this heterocycloalkyl ring is optionally interrupted one or more times, the same way or differently, by a member of the group comprising, preferably consisting of, —$NR^{11g}$—, or —O—;

$R^{13a}$, $R^{13c}$,
$R^{13e}$,
and $R^{13f}$ independently from each other represent hydrogen, hydroxy or —$NR^{19}R^{20}$, or are, independently from each other, selected from a group comprising, preferably consisting of, —$C_1$-$C_6$-alkyl, —$C_1$-$C_6$-alkoxy, —$C_3$-$C_{10}$-cycloalkyl and —$C_3$-$C_{10}$-heterocycloalkyl, wherein said residues are unsubstituted or substituted one or more times independently from each other with halogen, nitro, cyano, —$C_1$-$C_6$-alkyl, or aryl, wherein aryl is unsubstituted or substituted one or more times with halogen, nitro, cyano, —$C_1$-$C_6$-alkyl, —$C_1$-$C_6$-alkoxy, —$C_1$-$C_6$-haloalkyl, or —$C_1$-$C_6$-haloalkoxy;

$R^{14c}$ and $R^{14f}$ independently from each other represent hydrogen or —$NR^{19a}R^{20a}$, or are, independently from each other, selected from a group comprising, preferably consisting of, —$C_1$-$C_6$-alkyl, —$C_3$-$C_{10}$-cycloalkyl and —$C_3$-$C_{10}$-heterocycloalkyl, wherein said residues are unsubstituted or substituted one or more times independently from each other with halogen, —$C_1$-$C_6$-alkyl, or aryl, wherein aryl is unsubstituted or substituted one or more times with halogen, nitro, cyano, —$C_1$-$C_6$-alkyl, —$C_1$-$C_6$-alkoxy, —$C_1$-$C_6$-haloalkyl, or —$C_1$-$C_6$-haloalkoxy;

$R^{19}$, $R^{19a}$,
$R^{20}$,
and $R^{20a}$ independently from each other represent hydrogen, —$C_1$-$C_6$-alkyl or —$(CH_2)_z$-phenyl;

s, t and x independently from each other represent an integer of 0, 1, or 2;

p, q,
u, and v independently from each other represent an integer of 0, 1, 2, 3 or 4;

z represents an integer of 0 or 1.

In accordance with a more particularly preferred embodiment, the present invention relates to compounds of general formula I, supra, in which:

A and E are phenylene;

G is selected from the group comprising, preferably consisting of, —$C(O)NR^9$—, —$S(O)_2$—, and —$C(O)$—Y—;

X is selected from the group comprising, preferably consisting of —O—, —S—, and —$NR^{10}$—;

Y is selected from the group comprising, preferably consisting of —$C_1$-$C_3$-alkylene and —$C_3$-cycloalkylene;

$R^1$ is hydrogen;

$R^2$ represents hydrogen, or —$C(O)R^{13a}$;

$R^3$ is selected from a group comprising, preferably consisting of —$C_1$-$C_6$-alkyl, $C_3$-$C_6$-cycloalkyl, and phenyl;

$R^4$ is selected from a group comprising, preferably consisting of —$C_1$-$C_6$-alkyl, and —$(CH_2)_u$-aryl, wherein said residues are unsubstituted or substituted one or more times independently from each other with halogen, —$C_1$-$C_6$-alkyl, —$C_3$-$C_{10}$-cycloalkyl, —$C_3$-$C_{10}$-heterocycloalkyl, —$OR^{11c}$, or —$NR^{11c}R^{12c}$;

$R^5$ is selected from the group comprising, preferably consisting of, hydrogen, methyl, fluoro, and chloro;

$R^6$ is hydrogen;

$R^7$ is a substituent selected from the group comprising, preferably consisting of hydrogen, halogen, cyano, hydroxyl, $C_1$-$C_6$-alkoxy, $C_1$-$C_6$-haloalkoxy, —$C_1$-$C_6$-alkyl, and —$C_1$-$C_6$-haloalkyl;

$R^8$ is a substituent selected from the group comprising, preferably consisting of hydrogen, halogen, cyano, —$(CH_2)_v$$OR^{11e}$, —$(CH_2)_vNR^{11e}R^{12e}$, —$C_1$-$C_6$-alkyl, —$C_3$-$C_{10}$-cycloalkyl, —$C_3$-$C_{10}$-heterocycloalkyl, —$C_1$-$C_6$-haloalkyl, —$(CH_2)_vC(O)R^{13e}$, —$(CH_2)_vC(O)NR^{11e}R^{12e}$ and —$(CH_2)_vS(O)_2NR^{11e}R^{12e}$;

$R^9$ and $R^{10}$ are hydrogen;

$R^{11c}$, $R^{11e}$,
$R^{11f}$, $R^{11g}$,
$R^{12c}$, $R^{12e}$, and $R^{12f}$ independently from each other represent hydrogen, or —$C(O)R^{13f}$, or are selected from the group comprising, preferably consisting of, —$C_1$-$C_6$-alkyl, and —$C_3$-$C_{10}$-cycloalkyl, wherein said residues of $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are unsubstituted or substituted one or more times independently from each other with halogen, —$OR^{11f}$, or —$NR^{11f}R^{12f}$; and wherein said residues of $R^{11f}$, $R^{12f}$ are unsubstituted or substituted one or more times independently from each other with halogen, or substituted one time with —$OR^{11f}$ or —$NR^{11f}R^{12f}$; or $R^{11c}$ and $R^{12c}$,
$R^{11e}$ and $R^{12e}$,
and
$R^{12f}$ and $R^{12f}$ independently from each other, together with the nitrogen atom to which they are attached in groups —$NR^{11c}R^{12c}$, —$NR^{11e}R^{12e}$, and —$NR^{11f}R^{12f}$ form a 3 to 7 membered heterocycloalkyl ring, wherein the carbon backbone of this heterocycloalkyl ring is optionally interrupted one or more times, the same way or differently, by a member of the group comprising, preferably consisting of, —$NR^{11g}$—, or —O—;

$R^{13a}, R^{13e}$, and $R^{13f}$ independently from each other represent hydrogen, hydroxy or —$NR^{19}R^{20}$, or are, independently from each other, selected form a group comprising, preferably consisting of, —$C_1$-$C_6$-alkyl, or —$C_1$-$C_6$-alkoxy, wherein said residues are unsubstituted or substituted one or more times independently from each other with halogen, or phenyl;

$R^{19}$ and $R^{20}$ independently from each other represent hydrogen, —$C_1$-$C_6$-alkyl or —$(CH_2)_z$-phenyl;

p, q, and z, independently of each other, represent an integer of 0 or 1;

u, and v independently of each other, represent an integer of 0, 1, 2, 3, or 4.

In accordance with a variant, the present invention relates to compounds of general formula I, supra, in which:

A and E are phenylene;

G is selected from the group comprising, preferably consisting of, —C(O)$NR^9$—, —$S(O)_2$—, and —C(O)—Y—;

X is selected from the group comprising, preferably consisting of —O—, —S—, and —$NR^{10}$—;

Y is selected from the group comprising, preferably consisting of —$C_1$-$C_3$-alkylene and —$C_3$-cycloalkylene;

$R^1$ is hydrogen;

$R^2$ represents hydrogen, or —C(O)$R^{13a}$;

$R^3$ is selected from a group comprising, preferably consisting of —$C_1$-$C_6$-alkyl, $C_3$-$C_6$-cycloalkyl, and phenyl;

$R^4$ is selected from a group comprising, preferably consisting of —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{10}$-heterocycloalkyl, —$(CH_2)_u$-aryl and —$(CH_2)_u$-heteroaryl, wherein said residues are unsubstituted or substituted one or more times independently from each other with halogen, nitro, cyano, —$C_1$-$C_6$-alkyl, —$C_3$-$C_{10}$-cycloalkyl, —$C_3$-$C_{10}$-heterocycloalkyl, —$OR^{11c}$, —$NR^{11c}R^{12c}$, —$C_1$-$C_6$-haloalkyl, —C(O)$R^{13c}$, or —$S(O)_2R^{14c}$;

$R^5$ is selected from the group comprising, preferably consisting of, hydrogen, methyl, fluoro, and chloro;

$R^6$ is hydrogen;

$R^7$ is hydrogen, halogen, $C_1$-$C_6$-alkyl, or $C_1$-$C_6$-haloalkyl;

$R^8$ is a substituent selected from the group comprising, preferably consisting of hydrogen, halogen, $C_1$-$C_6$-alkyl, $C_1$-$C_6$-alkoxy, $C_1$-$C_6$-haloalkyl, and $C_1$-$C_6$-haloalkoxy;

$R^9$ and $R^{10}$ are hydrogen;

$R^{11a}, R^{11c}$,
$R^{11e}, R^{11f}$,
$R^{11g}, R^{12c}$, $R^{12e}, R^{12f}$ independently from each other represent hydrogen or —C(O)$R^{13f}$, or are selected from the group comprising, preferably consisting of, —$C_1$-$C_6$-alkyl, and —$C_3$-$C_{10}$-cycloalkyl, wherein said residues of $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are unsubstituted or substituted one or more times independently from each other with halogen, —$OR^{11f}$, or —$NR^{11f}R^{12f}$; and wherein said residues of $R^{11f}$, $R^{12f}$ are unsubstituted or substituted one or more times independently from each other with halogen, or substituted one time with —$OR^{11f}$ or —$NR^{11f}R^{12f}$; or $R^{11c}$ and $R^{12c}$,
$R^{11e}$ and $R^{12e}$, and $R^{12f}$ and $R^{12f}$ independently from each other, together with the nitrogen atom to which they are attached in groups —$NR^{11c}R^{12c}$, —$NR^{11e}R^{12e}$, and —$NR^{11f}R^{12f}$ form a 3 to 7 membered heterocycloalkyl ring, wherein the carbon backbone of this heterocycloalkyl ring is optionally interrupted one or more times, the same way or differently, by a member of the group comprising, preferably consisting of, —$NR^{11g}$— and —O—;

$R^{13a}, R^{13e}$, and $R^{13f}$ independently from each other represent hydrogen, hydroxy or —$NR^{19}R^{20}$, or are, independently from each other, selected from a group comprising, preferably consisting of, —$C_1$-$C_6$-alkyl, and —$C_1$-$C_6$-alkoxy, wherein said residues are unsubstituted or substituted one or more times independently from each other with halogen, or phenyl;

$R^{14c}$ represents hydrogen, —$NR^{19a}R^{20a}$, or —$C_1$-$C_6$-alkyl, wherein —$C_1$-$C_6$-alkyl is unsubstituted or substituted one or more times with halogen or phenyl;

$R^{19}, R^{19a}$,
$R^{20}$, and $R^{20a}$ independently from each other represent hydrogen, —$C_1$-$C_6$-alkyl or —$(CH_2)_z$-phenyl;

p, q, and z, independently of each other, represent an integer of 0 or 1;

u, and v independently of each other, represent an integer of 0, 1, 2, 3, or 4.

In accordance with an even more particularly preferred embodiment, the present invention relates to compounds of general formula I, supra, in which:

A and E are phenylene;

G is selected from the group comprising, preferably consisting of, —C(O)$NR^9$—, —$S(O)_2$—, and —C(O)—Y—;

X is —S— or —$NR^{10}$—;

Y is $C_3$-cycloalkylene;

$R^1$ is hydrogen;

$R^2$ represents hydrogen, or —C(O)$OC_2H_5$;

$R^3$ is methyl;

$R^4$ is $C_1$-$C_6$-alkyl, which is unsubstituted or substituted one or more times independently from each other with —$C_3$-$C_{10}$-heterocycloalkyl, —$OR^{11c}$ or —$NR^{11c}R^{12c}$;

$R^5$ is hydrogen or fluoro;

$R^6$ is hydrogen;

$R^7$ is hydrogen or halogen;

$R^8$ is a substituent selected from the group comprising, preferably consisting of hydrogen, halogen, —$C_1$-$C_3$-alkyl and $C_1$-$C_3$-haloalkyl;

$R^9$ and $R^{10}$ are hydrogen;

$R^{11c}$ and $R^{12c}$ are, independently from each other, hydrogen or $C_1$-$C_6$-alkyl; or together with the nitrogen atom to which they are attached, form a 5- to 6-membered heterocycloalkyl ring, wherein the carbon backbone of this heterocycloalkyl ring is optionally interrupted one or more times, the same way or differently, by a member of the group comprising, preferably consisting of, —$NCH_3$—, or —O—;

p, q are 0.

DEFINITIONS

Within the context of the present application, the terms as mentioned herein and in the claims have preferably the following meanings:

The term "alkyl", as used in the context of the term "alkyl" or "alkylcarbonyl", for example, is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and the isomers thereof.

The term "haloalkyl" is to be understood as preferably meaning branched and unbranched alkyl, as defined supra, in which one or more of the hydrogen substituents is replaced in the same way or differently with halogen. Particularly preferably, said haloalkyl is, e.g. chloromethyl, fluoropropyl, fluoromethyl, difluoromethyl, trichloromethyl, 2,2,2-trifluoroethyl, pentafluoroethyl, bromobutyl, trifluoromethyl, iodoethyl, and isomers thereof.

The term "alkoxy" is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and the isomers thereof.

The term "alkylthio" is to be understood as preferably meaning branched and unbranched alkylthio, meaning e.g. methylthio, ethylthio, propylthio, iso-propylthio, butylthio, iso-butylthio, tert-butylthio, sec-butylthio, pentylthio, iso-pentylthio, hexylthio, heptylthio, octylthio, nonylthio, decylthio, undecylthio and dodecylthio and the isomers thereof.

The term "haloalkoxy" is to be understood as preferably meaning branched and unbranched alkoxy, as defined supra, in which one or more of the hydrogen substituents is replaced in the same way or differently with halogen, e.g. chloromethoxy, fluoromethoxy, pentafluoroethoxy, fluoropropyloxy, difluoromethyloxy, trichloromethoxy, 2,2,2-trifluoroethoxy, bromobutyloxy, trifluoromethoxy, iodoethoxy, and isomers thereof.

The term "cycloalkyl" is to be understood as preferably meaning a $C_3$-$C_{10}$ cycloalkyl group, more particularly a saturated cycloalkyl group of the indicated ring size, meaning e.g. a cyclopropyl, cyclobutyl, cyclopentyl, cyclohexyl, cycloheptyl, cyclooctyl, cyclononyl, or cyclodecyl group; and also as meaning an unsaturated cycloalkyl group containing one or more double bonds in the C-backbone, e.g. a $C_3$-$C_{10}$ cycloalkenyl group, such as, for example, a cyclopropenyl, cyclobutenyl, cyclopentenyl, cyclohexenyl, cycloheptenyl, cyclooctenyl, cyclononenyl, or cyclodecenyl group, wherein the linkage of said cyclolalkyl group to the rest of the molecule can be provided to the double or single bond.

The term "heterocycloalkyl" is to be understood as preferably meaning a $C_3$-$C_{10}$ cycloalkyl group, as defined supra, featuring the indicated number of ring atoms, wherein one or more ring atoms are heteroatoms such as $NR^{11g}$, oxygen or sulfur, or carbonyl groups, or, —otherwise stated—in a $C_n$-cycloalkyl group one or more carbon atoms are replaced by these heteroatoms to give such $C_n$ cycloheteroalkyl group. Thus such group refers e.g. to a three-membered heterocycloalkyl, expressed as —$C_3$-heterocycloalkyl such as oxyranyl. Other examples of heterocycloalkyls are oxetanyl ($C_4$), aziridinyl ($C_3$), azetidinyl ($C_4$), tetrahydrofuranyl ($C_5$), pyrrolidinyl ($C_5$), morpholinyl ($C_6$), dithianyl ($C_6$), thiomorpholinyl ($C_6$), piperazinyl ($C_6$), trithianyl ($C_6$) and chinuclidinyl ($C_8$).

The term "halogen" or "Hal" is to be understood as preferably meaning fluorine, chlorine, bromine, or iodine.

The term "alkenyl" is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group, and isomers thereof.

The term "alkynyl" is to be understood as preferably meaning branched and unbranched alkynyl, e.g. an ethynyl, prop-1-yn-1-yl, but-1-yn-1-yl, but-2-yn-1-yl, or but-3-yn-1-yl group, and isomers thereof.

As used herein, the term "aryl" is defined in each case as having 3-12 carbon atoms, i.e. having 3, 4, 5, 6, 7, 8, 9, 10, 11, or 12 carbon atoms, preferably 6-12 carbon atoms, i.e. 6, 7, 8, 9, 10, 11, or 12 carbon atoms, such as, for example, cyclopropenyl, cyclopentadienyl, phenyl, tropyl, cyclooctadienyl, indenyl, naphthyl, azulenyl, biphenyl, fluorenyl, anthracenyl etc., phenyl being preferred.

As used herein, the term "heteroaryl" is understood as meaning an aromatic ring system which comprises 3-16 ring atoms, i.e. 3, 4, 5, 6, 7, 8, 9, 10, 11, 12, 13, 14, 15, or 16 ring atoms, preferably 5 or 6 or 9 or 10 atoms, and which contains at least one heteroatom which may be identical or different, said heteroatom being such as oxygen, nitrogen or sulfur, and can be monocyclic, bicyclic, or tricyclic, and in addition in each case can be benzocondensed. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

The term "alkylene", as used herein in the context of the compounds of general formula (I) is to be understood as meaning an optionally substituted alkyl chain or "tether", having 1, 2, 3, 4, 5, or 6 carbon atoms, i.e. an optionally substituted —$CH_2$— ("methylene" or "single membered tether" or e.g. —C(Me)$_2$—), or —CH(Me)-[(R)- or (S)-isomers], —$CH_2$—$CH_2$— ("ethylene", "dimethylene", or "two-membered tether"), —$CH_2$—$CH_2$—$CH_2$— ("propylene", "trimethylene", or "three-membered tether"), —$CH_2$—$CH_2$—$CH_2$—$CH_2$— ("butylene", "tetramethylene", or "four-membered tether"), —$CH_2$—$CH_2$—$CH_2$—$CH_2$—$CH_2$— ("pentylene", "pentamethylene" or "five-membered ether"), or —$CH_2$—$CH_2$—$CH_2$—$CH_2$—$CH_2$—$CH_2$— ("hexylene", "hexamethylene", or six-membered tether") group. Preferably, said alkylene tether is 1, 2, 3, 4, or 5 carbon atoms, more preferably 1, 2 or 3 carbon atoms.

The term "cycloalkylene", as used herein in the context of the compounds of general formula (I) is to be understood as meaning an optionally substituted cycloalkyl ring, having 3, 4, 5, 6, 7, or 8, preferably 3, 4, 5, or 6, carbon atoms, i.e. an optionally substituted cyclopropyl, cyclobutyl, cyclopentyl, cyclohexyl, cycloheptyl, or cyclooctyl ring, preferably a cyclopropyl, cyclobutyl, cyclopentyl or cyclohexyl ring.

The term "arylene", as used herein in the context of the compounds of general formula (I) is to be understood as meaning an optionally substituted monocyclic or polycyclic arylene aromatic system e.g. arylene, naphthylene and biarylene, preferably an optionally substituted phenyl ring or "tether", having 6 or 10 carbon atoms. More preferably, said arylene tether is a ring having 6 carbon atoms, i.e. a "phenylene" ring. If the term "arylene" or e.g. "phenylene" is used it is to be understood that the linking residues can be arranged to each other in ortho-, para- and meta-position, e.g. an optionally substituted moiety of structure:

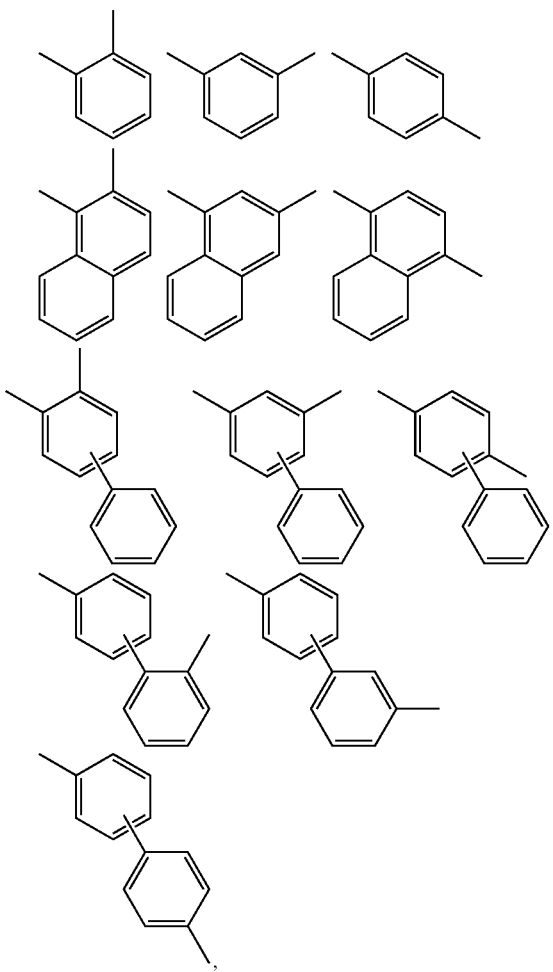

in which linking positions on the rings are shown as non-attached bonds.

The term "heteroarylene", as used herein in the context of the compounds of general formula (I) which includes the groups A and E, is to be understood as meaning an optionally substituted monocyclic or polycyclic heteroarylene aromatic system, e.g. heteroarylene, benzoheteroarylene, preferably an optionally substituted 5-membered heterocycle, such as, for example, furan, pyrrole, thiazole, oxazole, isoxazole, or thiophene or "tether", or a 6-membered heterocycle, such as, for example, pyridine, pyrimidine, pyrazine, pyridazine. More preferable, said heteroarylene tether is a ring having 6 carbon atoms, e.g. an optionally substituted structure as shown supra for the arylene moieties, but which contains at least one heteroatom which may be identical or different, said heteroatom being such as oxygen, nitrogen or sulfur. When the term "heteroarylene" is used it is to be understood that the linking residues can be arranged to each other in ortho-, para- or meta-position.

As used herein, the term "$C_1$-$C_6$", as used throughout this text, e.g. in the context of the definition of "$C_1$-$C_6$-alkyl", or "$C_1$-$C_6$-alkoxy", is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$ $C_1$-$C_6$; preferably $C_1$-$C_2$, $C_1$-$C_3$, $C_1$-$C_4$, $C_1$-$C_5$, $C_1$-$C_6$; more preferably $C_1$-$C_4$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; preferably $C_2$-$C_3$.

As used herein, the term "$C_3$-$C_{10}$", as used throughout this text, e.g. in the context of the definitions of "$C_3$-$C_{10}$-cycloalkyl", "$C_3$-$C_{10}$-heterocycloalkyl", or "$C_3$-$C_{10}$-cycloalkylene" is to be understood as meaning a cycloalkyl or heterocycloalkyl group or a cycloalkylene tether having a finite number of carbon atoms of 3 to 10, i.e. 3, 4, 5, 6, 7, 8, 9 or 10 carbon atoms, preferably 3, 4, 5 or 6 carbon atoms. It is to be understood further that said term "$C_3$-$C_{10}$" is to be interpreted as any sub-range comprised therein, e.g. $C_3$-$C_{10}$, $C_4$-$C_9$, $C_5$-$C_8$, $C_6$-$C_7$; preferably $C_3$-$C_6$.

As used herein, the term "$C_3$-$C_6$", as used throughout this text, e.g. in the context of the definitions of "$C_3$-$C_6$-cycloalkyl", "$C_3$-$C_6$-heterocycloalkyl", or "$C_3$-$C_6$-cycloalkylene" is to be understood as meaning a cycloalkyl group or a heterocycloalkyl group or a cycloalkylene tether having a finite number of carbon atoms of 3 to 6, i.e. 3, 4, 5, or 6 carbon atoms. It is to be understood further that said term "$C_3$-$C_6$" is to be interpreted as any sub-range comprised therein, e.g. $C_3$-$C_4$, $C_4$-$C_6$, $C_5$-$C_6$.

Further, as used herein, the term "$C_3$-$C_8$", as used throughout this text e.g. in the context of the definitions of "$C_3$-$C_8$-cycloalkyl", is to be understood as meaning a cycloalkyl group having a finite number of carbon atoms of 3 to 8, i.e. 3, 4, 5, 6, 7 or 8 carbon atoms. It is to be understood further that said term "$C_3$-$C_8$" is to be interpreted as any sub-range comprised therein, e.g. $C_3$-$C_8$, $C_4$-$C_7$, $C_5$-$C_6$, $C_3$-$C_4$, $C_3$-$C_5$, $C_3$-$C_6$, $C_3$-$C_7$.

As used herein, the term "$C_1$-$C_3$", as used throughout this text, e.g. in the context of the definitions of "$C_1$-$C_3$-alkylene", is to be understood as meaning an alkylene group as defined supra having a finite number of carbon atoms of 1 to 3, i.e. 1, 2, or 3. It is to be understood further that said term "$C_1$-$C_3$" is to be interpreted as any sub-range comprised therein, e.g. $C_1$-$C_2$, or $C_2$-$C_3$.

As used herein, the term "one or more times", e.g. in the definition of the substituents of the compounds of the general formulae of the present invention, is understood as meaning "one, two, three, four or five times, particularly one, two, three or four times, more particularly one, two or three times, more particularly one or two times".

The term "isomers" is to be understood as meaning chemical compounds with the same number and types of atoms as another chemical species. There are two main classes of isomers, constitutional isomers and stereoisomers.

The term "constitutional isomers" is to be understood as meaning chemical compounds with the same number and types of atoms, but they are connected in differing sequences. There are functional isomers, structural isomers, tautomers or valence isomers.

In stereoisomers, the atoms are connected sequentially in the same way, such that condensed formulae for two isomeric molecules are identical. The isomers differ, however, in the way the atoms are arranged in space. There are two major sub-classes of stereoisomers; conformational isomers, which interconvert through rotations around single bonds, and configurational isomers, which are not readily interconvertable.

Configurational isomers are, in turn, comprised of enantiomers and diastereomers. Enantiomers are stereoisomers which are related to each other as mirror images. Enantiomers can contain any number of stereogenic centers, as long as each center is the exact mirror image of the corresponding center in the other molecule. If one or more of these centers differs in configuration, the two molecules are no longer mirror images. Stereoisomers which are not enantiomers are called diastereomers. Diastereomers which still have a different constitution, are another sub-class of diastereomers, the best known of which are simple cis-trans isomers.

In order to limit different types of isomers from each other reference is made to IUPAC Rules Section E (*Pure Appl Chem* 45, 11-30, 1976).

The term "leaving group", is, as is understood by the person skilled in the art, to be understood as meaning a group which detaches from an organic molecule, e.g. by a chemical reaction, such as a substitution reaction for example. For example, said leaving group can be a halogen atom, a trifluoromethanesulphonate ("triflate") group, methanesulphonate, p-toluenesulphonate, etc. In the particular case of the their attachment to an activated position of an aromatic heterocycle, such as the 2- or 4-position of a pyrimidine group for example, also other groups such as sulphones, or sulphoxides, can act as leaving groups. Particularly cited is the leaving group —S(O)$_w$R$^4$ as defined infra.

Further Embodiments

The compound according to Formula (I) can exist in free form or in a salt form. A suitably pharmaceutically acceptable salt of the substituted sulphoximines of the present invention may be, for example, an acid-addition salt of a substituted sulphoximine of the invention which is sufficiently basic, for example, an acid-addition salt with, for example, an inorganic or organic acid, for example hydrochloric, hydrobromic, sulfuric, phosphoric, trifluoroacetic, para-toluenesulfonic, methylsulfonic, citric, tartaric, succinic or maleic acid. In addition, another suitable pharmaceutically acceptable salt of a substituted sulphoximine of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, 1,6-hexadiamine, ethanolamine, glucosamine, sarcosine, serinol, tris-hydroxymethyl-aminomethane, aminopropandiol, sovak-base, 1-amino-2,3,4-butantriol.

The compound according to Formula (I) can exist as N-oxides which are defined in that at least one nitrogen of the compounds of the general Formula (I) may be oxidized.

In accordance with an embodiment of the present invention, the compounds according to Formula (I) can exist as solvates, in particular as hydrate, wherein the compound according to Formula (I) may contain polar solvents, in particular water, as structural element of the crystal lattice of the compounds. The amount of polar solvents, in particular water, may exist in a stoichiometric or unstoichiometric ratio. In case of stoichiometric solvates, e.g. hydrate, are possible hemi-, (semi-), mono-, sesqui-, di-, tri-, tetra-, penta- etc. solvates or hydrates, respectively. Also as part of the embodiment, the compounds according to formula (I) can exist as in vivo hydrolysable esters.

The compounds of the present invention according to Formula (I) can exist as prodrugs, e.g. as in vivo hydrolysable esters. As used herein, the term "in vivo hydrolysable ester" is understood as meaning an in vivo hydrolysable ester of a compound of formula (I) containing a carboxy or hydroxyl group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of formula (I) containing a hydroxyl group includes inorganic esters such as phosphate esters and [alpha]-acyloxyalkyl ethers and related compounds which as a result of the in vivo hydrolysis of the ester breakdown to give the parent hydroxyl group. Examples of [alpha]-acyloxyalkyl ethers include acetoxymethoxy and 2,2-dimethylpropionyloxymethoxy. A selection of in vivo hydrolysable ester forming groups for hydroxyl include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention according to Formula (I) and salts, solvates, N-oxides and prodrugs thereof may contain one or more asymmetric centers. Asymmetric carbon atoms may be present in the (R) or (S) configuration or (R,S) configuration. Substituents on a ring may also be present in either cis or trans form. It is intended that all such configurations (including enantiomers and diastereomers), are included within the scope of the present invention. Preferred stereoisomers are those with the configuration which produces the more desirable biological activity. Separated, pure or partially purified configurational isomers or racemic mixtures of the compounds of this invention are also included within the scope of the present invention. The purification of said isomers and the separation of said isomeric mixtures can be accomplished by standard techniques known in the art.

Another embodiment of the present invention is an intermediate compound of general formula Ib:

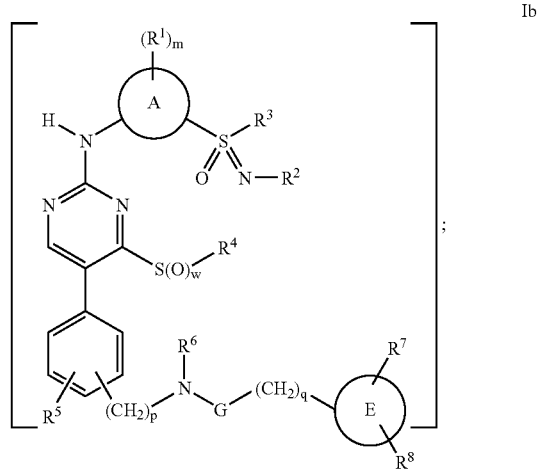

$w = 1, 2$ in which $R^1$, $R^2$, $R^3$, $R^5$, $R^6$, $R^7$, $R^8$, A, E, G, m, p, and q are as defined supra, w is an integer selected from 1 and 2, and $R^4$ is selected to form, together with the $—S(O)_w—$ to which it is attached, a leaving group, and in which $R^4$ represents $—C_1-C_6$-alkyl or $—(CH_2)_u$-aryl, as defined supra.

A further embodiment of the present invention relates to the use of the intermediate compounds of the general formulae 5, 6, I', 14a, Ib, and 7a as defined below for the preparation of a compound of general formula (I) as defined supra.

The compounds of the present invention can be used in treating diseases of dysregulated vascular growth or diseases which are accompanied with dysregulated vascular growth. Especially, the compounds effectively interfere with Tie2 signalling. The compounds of the present invention show surprisingly low levels of e.g. CDK2 inhibition. By primarily targeting an endothelial cell-specific kinase, compounds of the present invention may have an important advantage over prior art substances by reducing side effects which may result from interfering with signalling networks in non-endothelial cells. This effect can therefore allow prolonged treatment of patients with the compounds of the present invention offering good tolerability and high anti-angiogenic efficacy, where persistent angiogenesis plays a pathological role, and may indeed be used in the treatment of non-oncological diseases.

Therefore, another aspect of the present invention is a use of the compound of general formula (I) described supra for manufacturing a pharmaceutical composition for the treatment of diseases of dysregulated vascular growth or of diseases which are accompanied with dysregulated vascular growth.

Preferably, the use is in the treatment of diseases, wherein the diseases are tumours and/or metastases thereof.

Another preferred use is in the treatment of diseases, wherein the diseases are retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

A further use is in the treatment of diseases, wherein the diseases are coronary and peripheral artery disease.

Another use is in the treatment of diseases, wherein the diseases are ascites, oedema such as brain tumour associated oedema, high altitude trauma, hypoxia induced cerebral oedema, pulmonary oedema and macular oedema or oedema following burns and trauma, chronic lung disease, adult respiratory distress syndrome, bone resorption and for benign proliferating diseases such as myoma, benign prostate hyperplasia and wound healing for the reduction of scar formation, reduction of scar formation during regeneration of damaged nerves, endometriosis, pre-eclampsia, postmenopausal bleeding and ovarian hyperstimulation.

Yet another aspect of the invention is a method of treating a disease of dysregulated vascular growth or diseases which are accompanied with dysregulated vascular growth, by administering an effective amount of a compound of general formula (I) described supra.

Preferably, the diseases of said method are tumours and/or metastases thereof.

Also, the diseases of said method are retinopathy, other angiogenesis dependent diseases of the eye, in particular cornea transplant rejection or age-related macular degeneration, e.g. rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

Further, the disease of the method is coronary and peripheral artery disease.

Other diseases of the method are ascites, oedema such as brain tumour associated oedema, high altitude trauma, hypoxia induced cerebral oedema, pulmonary oedema and macular oedema or oedema following burns and trauma, chronic lung disease, adult respiratory distress syndrome, bone resorption and for benign proliferating diseases such as myoma, benign prostate hyperplasia and wound healing for the reduction of scar formation, reduction of scar formation during regeneration of damaged nerves, endometriosis, pre-eclampsia, postmenopausal bleeding and ovarian hyperstimulation.

The compounds of the present invention can thus be applied for the treatment of diseases accompanied by neoangiogenesis. This holds principally true for all solid tumours, e.g. breast, colon, renal, lung and/or brain tumours or metastases thereof and can be extended to a broad range of diseases, where pathologic angiogenesis is persistent. This applies for diseases with inflammatory association, diseases associated with oedema of various forms and diseases associated with stromal proliferation and pathologic stromal reactions broadly. Particularly suited is the treatment for gynaecological diseases where inhibition of angiogenic, inflammatory and stromal processes with pathologic character can be inhibited. The treatment is therefore an addition to the existing armament to treat diseases associated with neoangiogenesis.

The compounds of the present invention can be used in particular in therapy and prevention of tumour growth and metastases, especially in solid tumours of all indications and stages with or without pre-treatment if the tumour growth is accompanied with persistent angiogenesis. However, with regard to the low level of e.g. CDK-inhibition, their use is not restricted to tumour therapy but is also of great value for the treatment of other diseases with dysregulated vascular growth. This includes retinopathy and other angiogenesis dependent diseases of the eye (e.g. cornea transplant rejection, age-related macular degeneration), rheumatoid arthritis, and other inflammatory diseases associated with angiogenesis such as psoriasis, delayed type hypersensitivity, contact dermatitis, asthma, multiple sclerosis, restenosis, pulmonary hypertension, stroke and inflammatory diseases of the bowel, such as Crohn's disease. This includes coronary and peripheral artery disease. This can be applied for disease states such as ascites, oedema, such as brain tumour associated oedema, high altitude trauma, hypoxia induced cerebral oedema, pulmonary oedema and macular oedema or oedema following burns and trauma. Furthermore, this is useful for chronic lung disease, adult respiratory distress syndrome. Also for bone resorption and for benign proliferating diseases such as myoma, benign prostate hyperplasia and wound healing for the reduction of scar formation. This is therapeutically valuable for the treatment of diseases, where deposition of fibrin or extracellular matrix is an issue and stroma proliferation is accelerated (e.g. fibrosis, cirrhosis, carpal tunnel syndrome etc). In addition this can be used for the reduction of scar formation during regeneration of damaged nerves, permitting the reconnection of axons. Further uses are endometriosis, pre-eclampsia, postmenopausal bleeding and ovarian hyperstimulation.

Another aspect of the present invention is a pharmaceutical composition which contains a compound of Formula (I) or pharmaceutically acceptable salts thereof, N-oxides, solvates, hydrates, in admixture with one or more suitable excipients. This composition is particularly suited for the treatment of diseases of dysregulated vascular growth or of diseases which are accompanied with dysregulated vascular growth as explained above.

In order that the compounds of the present invention be used as pharmaceutical products, the compounds or mixtures thereof may be provided in a pharmaceutical composition, which, as well as the compounds of the present invention for enteral, oral or parenteral application contain suitably pharmaceutically acceptable organic or inorganic inert base material, e.g. purified water, gelatin, gum Arabic, lactate, starch, magnesium stearate, talcum, vegetable oils, polyalkylenglycol, etc.

The pharmaceutical compositions of the present invention may be provided in a solid form, e.g. as tablets, dragées, suppositories, capsules or in liquid form, e.g. as a solution, suspension or emulsion. The pharmaceutical composition may additionally contain auxiliary substances, e.g. preservatives, stabilisers, wetting agents or emulsifiers, salts for adjusting the osmotic pressure or buffers.

For parenteral applications, (including intravenous, subcutaneous, intramuscular, intravascular or infusion), sterile injection solutions or suspensions are preferred, especially aqueous solutions of the compounds in polyhydroxyethoxy containing castor oil.

The pharmaceutical compositions of the present invention may further contain surface active agents, e.g. salts of gallenic acid, phosphorlipids of animal or vegetable origin, mixtures thereof and liposomes and parts thereof.

For oral application tablets, dragées or capsules with talcum and/or hydrocarbon-containing carriers and binders, e.g. lactose, maize and potato starch, are preferred. Further application in liquid form is possible, for example as juice, which contains sweetener if necessary.

The dosage will necessarily be varied depending upon the route of administration, age, weight of the patient, the kind and severity of the illness being treated and similar factors. The daily dose is in the range of 0.5 to 1,500 mg. A dose can be administered as unit dose or in part thereof and distributed over the day. Accordingly the optimum dosage may be determined by the practitioner who is treating any particular patient.

It is possible for compounds of general formula (I) of the present invention to be used alone or, indeed in combination with one or more further drugs, particularly anti-cancer drugs or compositions thereof. Particularly, it is possible for said combination to be a single pharmaceutical composition entity, e.g. a single pharmaceutical formulation containing one or more compounds according to general formula (I) together with one or more further drugs, particularly anticancer drugs, or in a form, e.g. a "kit of parts", which comprises, for example, a first distinct part which contains one or more compounds according to general formula I, and one or more further distinct parts each containing one or more further drugs, particularly anti-cancer drugs. More particularly, said first distinct part may be used concomitantly with said one or more further distinct parts, or sequentially.

Another aspect of the present invention is a method which may be used for preparing the compounds according to the present invention.

General Processes and Experimental Details

The following Table lists the abbreviations used in the following paragraphs and in the Examples section as far as they are not explained within the text body.

| Abbreviation | Meaning |
|---|---|
| Boc | tert-butyloxycarbonyl |
| br | Broad |
| c- | cyclo- |
| CI | chemical ionisation |
| d | Doublet |
| dd | doublet of doublet |
| DCM | Dichloromethane |
| DIPEA | N,N-diisopropylethyl amine |
| DMAP | N,N-dimethylaminopyridine |
| DMF | N,N-dimethylformamide |
| DMSO | dimethyl sulfoxide |
| eq. | Equivalent |
| ESI | electrospray ionisation |
| GP | general procedure |
| HPLC | high performance liquid chromatography |
| LC-MS | liquid chromatography mass spectrometry |
| m | Multiplet |
| mc | centered multiplet |
| MS | mass spectrometry |
| MTBE | methyl-tert-butyl ether |
| NMR | nuclear magnetic resonance spectroscopy: chemical shifts (δ) are given in ppm. |
| Oxone ® | Potassium peroxomonosulfate (2KHSO$_5$•KHSO$_4$•K$_2$SO$_4$, e.g.from Aldrich) |
| Pd$_2$(dba)$_3$ | Tris-(dibenzylideneacetone)-dipalladium (0) |
| q | Quartet |
| rf | at reflux |
| r.t. or rt | room temperature |
| s | Singlet |
| t | Triplet |
| T3P | 1-propanephosphonic acid cyclic anhydride |
| TEA | Triethylamine |
| TFA | trifluoroacetic acid |
| THF | Tetrahydrofuran |
| TLC | thin-layer chromatography |

NMR peak forms are stated as they appear in the spectra, possible higher order effects have not been considered. In case diastereomeric mixtures have been analysed, the signal integrations refer to the cumulated signal of both diastereomers unless otherwise stated.

Where use of a microwave oven is mentioned, this refers to the use of a Discover microwave oven, CEM Inc., or the use of a Biotage Initiator microwave oven.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by trituration in a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with a Flashmaster II autopurifier (Argonaut/Biotage) and eluants such as gradients of hexane/EtOAc or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluants such as gradients of water and acetonitrile which may contain additives such as trifluoroacetic acid or aqueous ammonia. As well known to the person skilled in the art, purification of compounds by HPLC may thus give rise to their isolation as salts, such as, for example, as TFA salts or ammonium salts.

The following schemes and general procedures illustrate general synthetic routes to the compounds of general formula I of the invention and are not intended to be limiting. Specific examples are described in the subsequent paragraphs.

If the production of the compounds of general Formula I according to the invention is not described, the latter is carried out analogously to methods well known to the person skilled in the art. Such methods are available from suitable monographies, such as B. M. Trost, I. Fleming, Comprehensive Organic Synthesis, Perqamon Press 1991, and Heterocyclic compounds, Wiley, 1951-current, or from database systems such as SciFinder®, Beilstein CrossFire, or Science of Synthesis—Houben-Weyl Methods of Molecular Transformations (Thieme Chemistry).

As regards structure and configuration, sulfoximines as a rule are highly stable (C. Bolm, J. P. Hildebrand, *J. Org. Chem.* 2000, 65, 169). These properties of the functional group often allow even drastic reaction conditions and enable the simple derivatization of the sulfoximines on the imine nitrogen and the α-carbon. Enantiomerically pure sulfoximines are also used as auxiliaries in diastereoselective synthesis ((a) S. G. Pyne, *Sulphur Reports* 1992, 12, 57; (b) C. R. Johnson, *Aldrichchimica Acta* 1985, 18, 3). The preparation of enantiomerically pure sulfoximines can be accomplished for example via racemate separation with enantiomerically pure camphor-10-sulfonic acid ((a) C. R. Johnson, C. W. Schroeck, *J. Am. Chem. Soc.* 1973, 95, 7418, or via racemate separation by preparative chiral HPLC; (b) C. S. Shiner, A. H. Berks, *J. Org. Chem.* 1988, 53, 5543). A further method for the preparation of optically active sulfoximines consists in the stereoselective imination of optically active sulfoxides ((a) C. Bolm, P. Müller, K. Harms, *Acta Chem. Scand.* 1996, 50, 305; (b) Y. Tamura, J. Minamikawa, K. Sumoto, S. Fujii, M. Ikeda, *J. Org. Chem.* 1973, 38, 1239; (c) (H. Okamura, C. Bolm, *Organic Letters* 2004, 6, 1305).

Scheme 1: Preparation of compounds of the formula I, in which $R^1$, $R^2$, $R^3$, $R^4$, $R^5$, $R^6$, $R^7$, $R^8$, A, G, E, X, m, p and q are as defined in the description and claims of this invention, from commercially available 5-halouracils. The group -B(OR)$_2$ either represents a boronic acid or an ester thereof (wherein the two OR groups together with the boron atom may form a cyclic ester, e.g. a pinacolate ester).

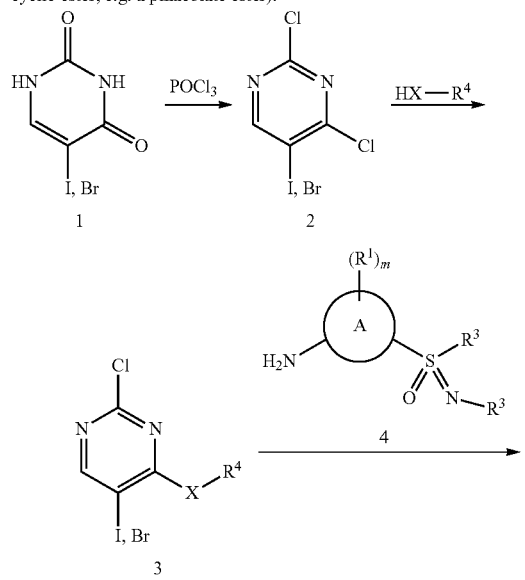

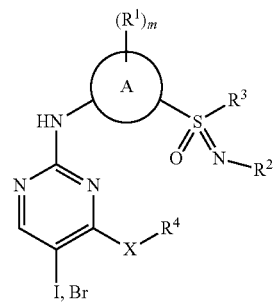

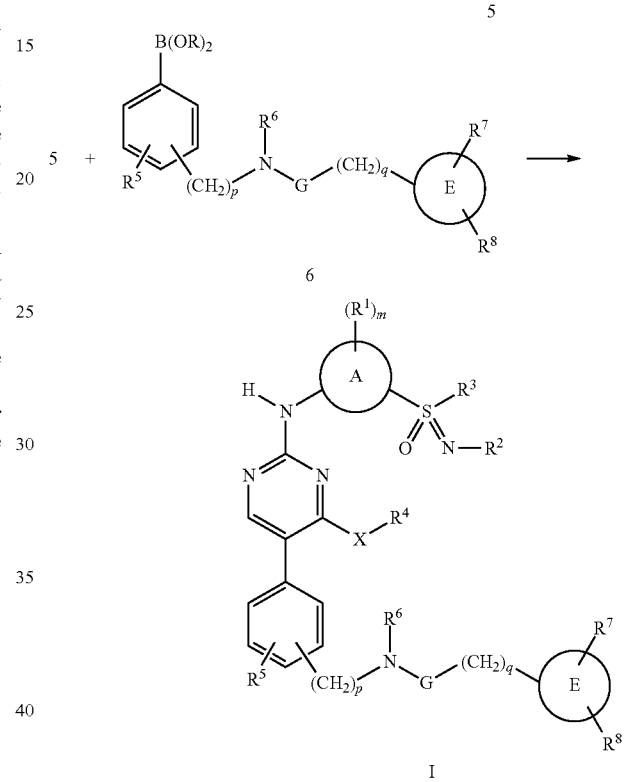

The synthesis of the compounds of the general formula I can, for example, commence with the chlorination of commercially available 5-halouracils 1, leading to 2,4-dichloro-5-halopyrimidines 2. This chlorination may be accomplished for example by reaction with POCl$_3$. Regioselective nucleophilic displacement of the chlorine attached to C-4 of the pyrimidine then leads to intermediates 3. Such displacements are well known to the person skilled in the art, see e.g. WO 2002096888. Compounds of the general formula 3 can subsequently be reacted with aromatic or heteroaromatic amines 4 featuring a sulfoximino moiety to give 2-aminopyrimidines 5. These, in turn, can then be subjected to transition metal mediated or catalysed coupling reactions, such as for example Suzuki-, Negishi-, Kumada-, Stille- or Genet-Molander-couplings, with suitable organometallic compounds or for example suitable organoboron or organostannane compounds. Preferably, compounds of general formula I are prepared by Pd-catalyzed Suzuki couplings of 2-aminopyrimidines of general formula 5 with organoboron compounds of the formula 6 (Scheme 1).

Scheme 2: Preparation amines of general formula 4, wherein $R^1$, $R^2$, $R^3$, A, and m are as defined in the description and claims of this invention.

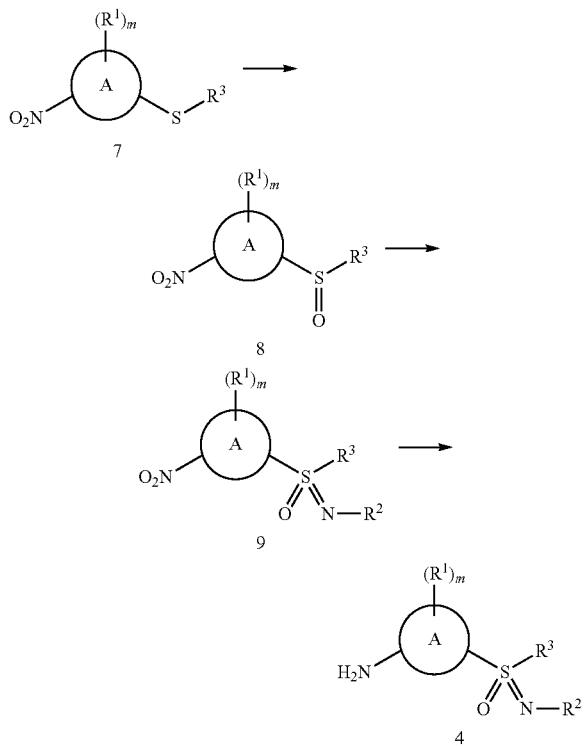

The aromatic or heteroaromatic amines 4 can be prepared e.g. starting from the corresponding thioethers 7 featuring a suitable precursor of the amino group in 4, e.g. a nitro group as shown in formula 7. Compounds of formula 7 are either commercially available or their syntheses are known to the person skilled in the art. Compounds of formula 7 can be readily oxidised to give sulfoxides of general formula 8, followed by further conversion into the respective sulfoximines of general formula 9. Nitro-reduction by a suitable reducing agent, such as activated iron, titanium (III) chloride, tin (II) chloride, or catalytic hydrogenation, then yields amines of general formula 4. More specifically, the synthesis of a variety of amines 4 is described in WO 2005037800.

The sulfoximino group (—S(=O)(=$NR^2$)—) as present e.g. in 9 and the corresponding amine 4, can be generated, e.g. from the corresponding sulfoxide 8 either in free ($R^2$=hydrogen) or substituted form (in which $R^2$ has the same meaning as defined in the description and claims of this invention but is different from hydrogen). Alternatively, the sulfoximine can be substituted on the NH group in a separate subsequent step resulting in a substituted sulfoximino group (—S(=O)(=$NR^2$)—) in which $R^2$ is different from hydrogen. For a general review article on sulfoximines see e.g. M. Reggelin, C. Zur, *Synthesis* 2000, 1.

Methods for the preparation of N-unsubstituted sulfoximines have been reported in the scientific literature, see e.g. C. R. Johnson, *J. Am. Chem. Soc.* 1970, 92, 6594; C. R. Johnson et al., *J. Org. Chem,* 1974, 39, 2458; R. Tanaka, K. Yamabe *Chem. Commun.* 1983, 329; H. Okamura, C. Bolm, *Org. Lett.* 2004, 6, 1305; the latter two methods also allow to convert non-racemic sulfoxides, which are e.g. available by asymmetric oxidation of thioethers (see, for example, H. Kagan et al., *J. Org. Chem.* 1995, 60, 8086) into the corresponding sulfoximines without loss of stereochemical information. Two very recent publications describe the preparation of N-Nosyl sulfoximines which can conveniently be further transformed into their N-unsubstituted analogues, see G. Y. Cho, C. Bolm, *Tetrahedron Lett.* 2005, 46, 8807, and G. Y. Cho, C. Bolm, *Org. Lett.* 2005, 7, 4983.

It is apparent to the person skilled in the art that the sulphur atom in non-symmetrically substituted sulfoximines is stereogenic. Enantiomerically pure sulfoximines can be prepared for example from enantiomerically pure sulfoxides (see above) or by separation (e.g. by HPLC) of a racemic sulfoximine mixture into its enantiomeric components. In cases where compounds of the present invention of formula I contain one or more additional stereocenters, diastereomeric mixtures may be separated into diastereomerically and enantiomerically pure compounds of the present invention by e.g. preparative HPLC.

It is furthermore made reference to the point that, as is clear to the person skilled in the art, compounds referred to as "sulphoximine", in this invention, may also be designated as "-sulfoximide" or, indeed, by the prefix "-sulfonimidoyl-", in accordance with the IUPAC Rules on chemical naming within the experimental section.

As a further illustration not limiting the present invention, examples for the syntheses of sulfoximine intermediates with $R^2$=—C(O)OC$_2$H$_5$ from sulfoximine intermediates with $R^2$=H are described in the experimental section (see e.g. Intermediate 4 and 6).

Alternatively, there are also methods known which directly lead to N-substituted sulfoximines —S(=O)(=$NR^2$)—, in which $R^2$ is different from hydrogen, see e.g. S. Cren et al., *Tetrahedron Lett.* 2002, 43, 2749, J. F. K. Mueller, P. Vogt, *Tetrahedron Lett.* 1998, 39, 4805, T. Bach, C. Korber, *Tetrahedron Lett.* 1998, 39, 5015.

It is evident to the person skilled in the art that the introduction and the removal of $R^2$ groups different from hydrogen may be performed either during the synthesis of compounds of the formula I as well as after the synthesis of these has been completed.

Scheme 3: Preparation of boronic acid derivatives of general formula 6a, 6b;
or 6c, wherein $R^5$, $R^6$, $R^7$, $R^8$, E, Y, p and q are as defined in the description and claims of this invention and wherein $R^9$ is hydrogen. The group -B(OR)$_2$ either represents a boronic acid or an ester thereof (wherein the two OR groups together with the boron atom may form a cyclic ester, e.g. a pinacolate ester).

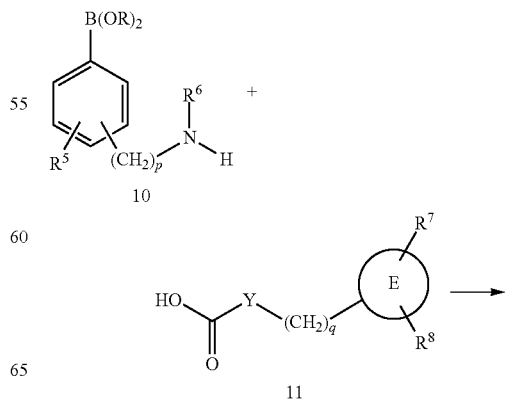

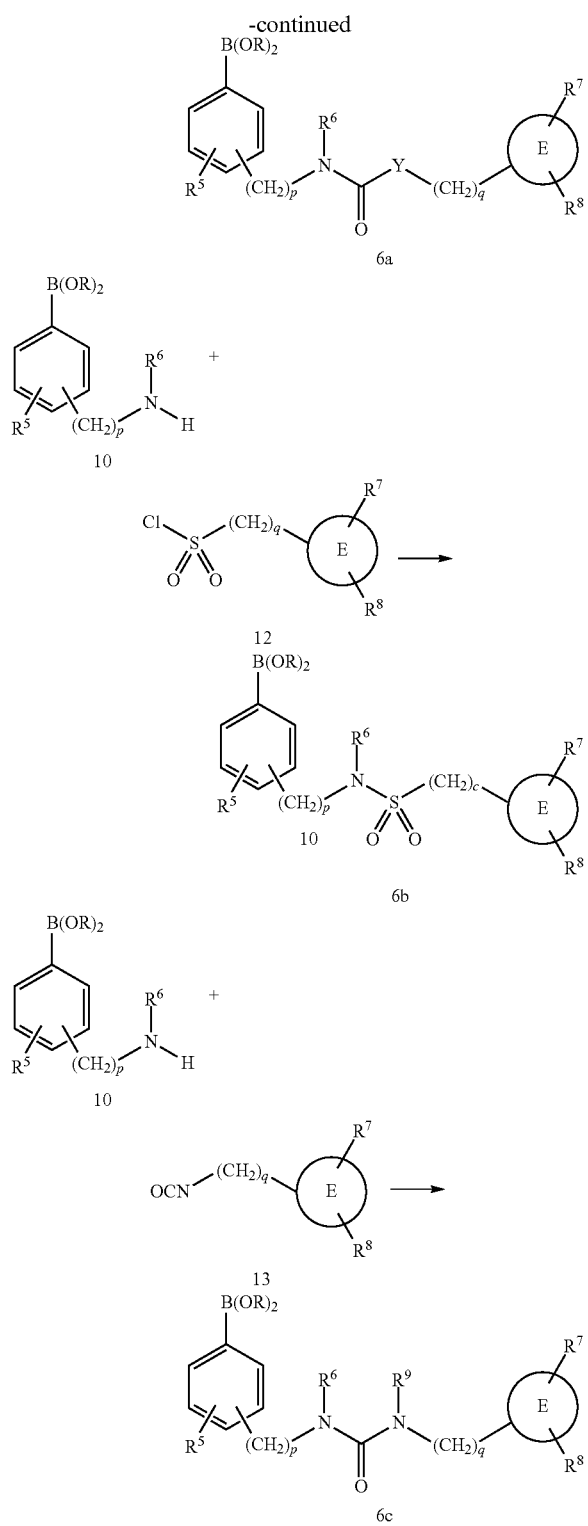

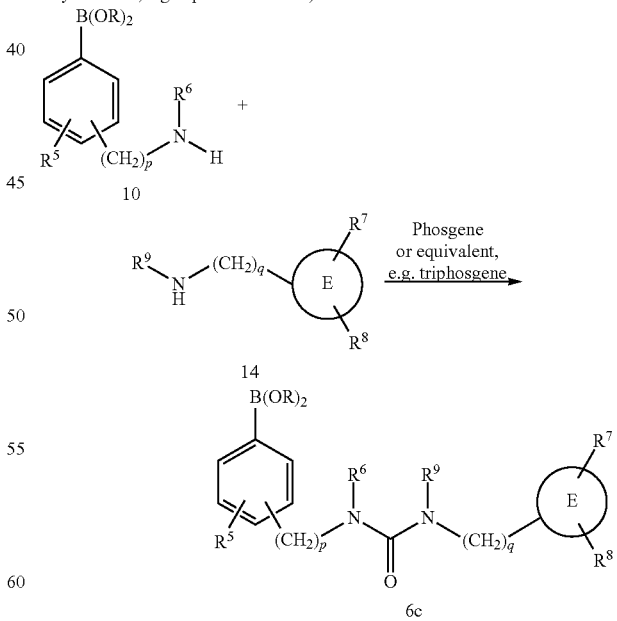

In particular, amides of general formula 6a are accessible by reaction of said amines of general formula 10 with carboxylic acids of the formula 11. Many methods for such amide formations are extractable from the scientific literature available to the person skilled in the art including, but not limited to, pre-formation of the more reactive carboxylic acid chloride (by reaction of carboxylic acids with e.g. thionyl chloride or sulfuryl chloride or oxalyl chloride), or in situ activation of the carboxylic acid in the presence of the amine by reaction with coupling reagents e.g. dicyclohexylcarbodiimide (DCC)/dimethylaminopyridine (DMAP), ethyldimethylaminopropylcarbodiimide (EDC)/DMAP, N,N'-carbonyldiimidazole (CDI), or T3P and others known to the person skilled in the art. Peptide coupling conditions may be amenable as well. Sulfonamides of general formula 6b can be prepared by reaction of amines of general formula 10 with sulfonyl chlorides of general formula 12. Finally, ureas of the general formula 6c are accessible by reacting amines of general formula 10 with isocyanates of the general formula 13. The respective isocyanates are either commercially available or can be prepared from the respective amines by standard chemistry known to the person skilled in the art, particularly by reaction with phosgene equivalents.

The person skilled in the art is well aware of alternative methods of forming ureas, which may be of special importance in cases where the respective isocyanates are not readily available, or where $R^9$ is different from hydrogen.

Scheme 4: Urea formation by in situ activation of one of two amines with triphosgene and subsequent reaction with a second amine, wherein $R^5$, $R^6$, $R^7$, $R^8$, $R^9$, E, p and q are as defined in the description and claims of this invention. The group -B(OR)$_2$ either represents a boronic acid or an ester thereof (wherein the two OR groups together with the boron atom may form a cyclic ester, e.g. a pinacolate ester).

The appropriately substituted boronic acid derivatives of general formula 6, more specifically their exemplary three sub-classes of general formula 6a, 6b and 6c, as needed for the conversion of 5-halopyrimidines 5 into the compounds of the general formula I (see Scheme 1) can be prepared starting from the respective amines of general formula 10 by standard transformations known to the person skilled in the art (Scheme 3).

An alternative process of generating ureas of general formula 6c is depicted in Scheme 4. Urea formation starting from amines of general formula 10 may be achieved by coupling with a second functionalized amine 14 via in situ transformation of one of the reacting amines into the respective carbamoyl chloride, aryl- or alkenylcarbamate (see for example *J. Org. Chem.* 2005, 70, 6960 and references cited therein). This process may provide an alternative to the formation and isolation of the respective isocyanate derived from one of the starting amines (see for example *Tetrahedron Lett.* 2004, 45, 4769). More particularly, ureas of formula 6c may be formed from amines and a suitable phosgene equivalent, preferably triphosgene, in an inert solvent, preferably acetonitrile, at temperatures ranging from −20° C. to room temperature, wherein room temperature is preferred (see also: *J. Org. Chem.* 1994, 59, 1937).

Processes for the preparation of functionalized (hetero)aryl amines are well known to the person skilled in the art. Starting from commercially available (hetero)aryl amines or nitro(hetero)arylenes well known transformations, including, but not limited to, e.g. alkylations, nucleophilic or electrophilic substitutions, acylations, halogenations, nitrations, sulfonylations, (transition) metal catalyzed couplings, metallations, rearrangements, reductions, and/or oxidations may be applied to prepare functionalized amines to be used in the urea formation step. In addition to specific procedures given in the following experimental section, detailed procedures may be found in the scientific and patent literature (see for example WO2005051366, WO2005110410, WO2005113494, and WO2006044823).

The carboxylic acids 11 required for the above described amide coupling reactions (Scheme 3) are either commercially available or are accessible from commercially available carboxylic esters or nitriles. Alternatively, (hetero)aryls bearing a methylenenitrile substituent are easily accessible from the respective halides via nucleophilic substitution reactions (e.g. employing KCN and a catalytic amount of KI in EtOH/$H_2O$). Incorporation of additional functionality into commercially available starting materials can be accomplished by a multitude of aromatic transformation reactions known to the person skilled in the art, including, but not limited to, e.g. electrophilic halogenations, electrophilic nitrations, Friedel-Crafts acylations, nucleophilic displacement of fluorine by oxygen nucleophiles and transformation of (hetero)aryl carboxylic acids into amides and subsequent reduction into benzylic amines, wherein the latter two methods are of particular relevance for the introduction of ether and/or aminomethylene side chains as $R^7$ and/or $R^8$ groups, respectively.

Benzylic nitriles and esters (and heteroaryl analogs thereof) can be efficiently alkylated at the benzylic position under basic conditions and subsequently hydrolyzed to the corresponding alkylated acids. Conditions for α-alkylations of nitriles and esters include, but are not limited to, the use of alkyl bromides or alkyl iodides as electrophiles under basic conditions in the presence or absence of a phase-transfer catalyst in a mono- or biphasic solvent system. Particularly, by using excess alkyl iodides as electrophilic species α,α-dialkylated nitriles are accessible. More particularly, by using 1,ω-dihaloalkyls as electrophiles cycloalkyl moieties can be installed at the benzylic position of nitriles and esters (*J. Med. Chem.* 1975, 18, 144; WO2003022852). The hydrolysis of nitriles to yield carboxylic acids can be accomplished, as known to the person skilled in the art, under acid or base-mediated conditions.

Scheme 5: Preparation of substituted 1-(hetero)aryl-cyclopropylcarboxylic acids 11a as an exemplification of the general route toward α-alkylated carboxylic acids as substrates for amide formations as described in Scheme 3, wherein E, $R^7$, and $R^8$ are as defined in the description and claims of this invention.

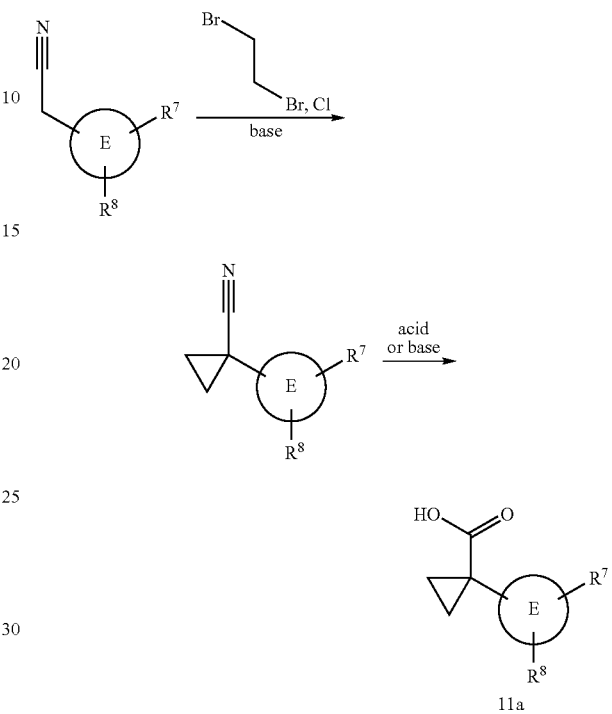

As an exemplification of the described general synthetic route toward functionalized carboxylic acids the more particular synthesis of substituted 1-(hetero)aryl-cyclopropyl-carboxylic acids is described in Scheme 5. This general route to (hetero)aryl-cyclopropyl carboxylic acids given herein is also applicable for the synthesis of the analogous higher homologs of (hetero)aryl-cycloalkyl carboxylic acids.

Scheme 6: Alternative preparation of compounds of the formula I from aminopyrimidines 5 via intermediates I', wherein $R^1$, $R^2$, $R^3$, $R^4$, $R^5$, $R^6$, $R^7$, $R^8$, A, G, E, X, m, p and q are as defined in the description and claims of this invention. The group -B(OR)$_2$ either represents a boronic acid or an ester thereof (wherein the two OR groups together with the boron atom may form a cyclic ester, e.g. a pinacolate ester). Elph- refers to an electrophilic group suitable to act as a precursor of G, such as HOC(O)-Y-, ClS(O)$_2$-, or OCN-, wherein Y has the meaning as defined in the description and claims of this invention.

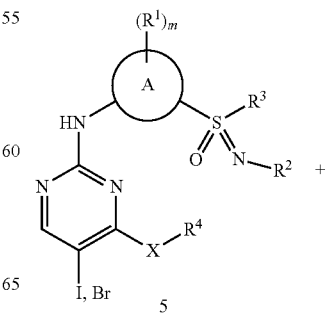

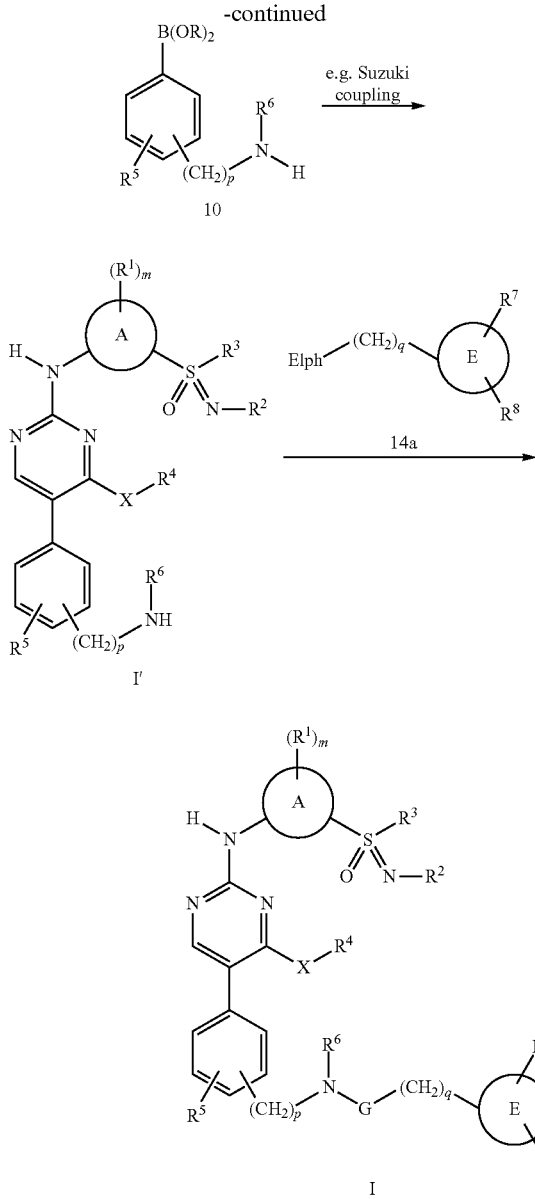

The person skilled in the art will readily recognise the possibility to modify the order of steps according to the synthetic requirements of the target molecule. As an illustrating but not limiting example, it is e.g. possible to react aminopyrimidines of the formula 5 with boronic acid derivatives of the general formula 10 in a transition metal mediated or catalysed coupling reaction, such as a Suzuki coupling, followed by reaction with a suitable electrophile, e.g. of the general formula 14a to give the compounds of the general formula I. Optionally, intermittent protection of the amine group in compounds of formula 10 may precede coupling to halopyrimidines of formula 5, followed by deprotection to give compounds of formula I'.

Furthermore, the person skilled in the art will readily recognise the possibility of diverse interconversions of various residues in the course of the synthesis of compounds as outlined in the preceding schemes 1 to 6, and also within the compounds of the general formula I. Such interconversions may require the use of protective groups in order to deactivate reactive moieties such as hydroxyl, amino, or carboxy groups. Such protective groups are well known to the person skilled in the art (see for example T. W. Greene and P. G. M. Wuts in *Protective Groups in Organic Synthesis*, 3$^{rd}$ edition, Wiley 1999).

Said interconversions can be furthermore exemplified by, but are not limited to, standard functional group interconversions such as (i) the reduction of a nitro or cyano group to an amine, followed by acylation, sulfonylation, or urea/carbamate formation, (ii) oxidations of alcohols to aldehydes, ketones and carboxylic acids as well as the complementary reductions, or (iii) nucleophilic displacement of a halide or a nitro group, e.g. by an alkoxide, a phenolate, or a thiolate.

Scheme 7: Interconversion of compounds of the formula Ia via intermediate sulfoxides and/or sulfones of the general formula Ib, wherein $R^4$ is selected to form, together with the -S(O)$_w$- to which it is attached in Ib, a leaving group, for example, $R^4$ represents -C$_1$-C$_6$-alkyl or -(CH$_2$)$_u$-aryl, and in which $R^1$, $R^2$, $R^3$, $R^5$, $R^6$, $R^7$, $R^8$, A, G, E, X, m, p and q are as defined in the description and claims of this invention, into the corresponding derivatives of the formula Ic, in which -XR$^4$ may represent e.g. a group -NR$^4$R$^{10}$, wherein $R^4$ and $R^{10}$ are as defined in the description and claims of this invention.

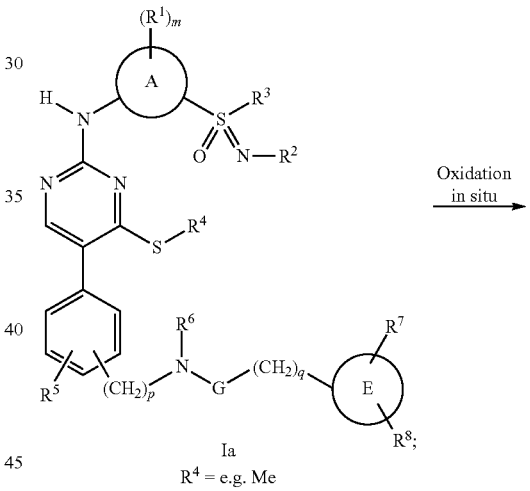

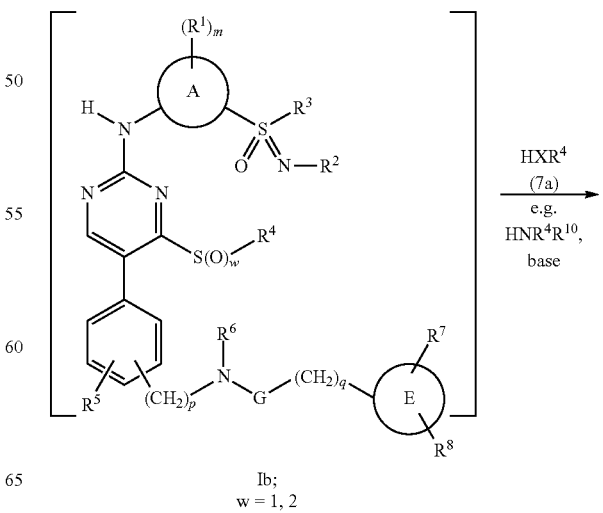

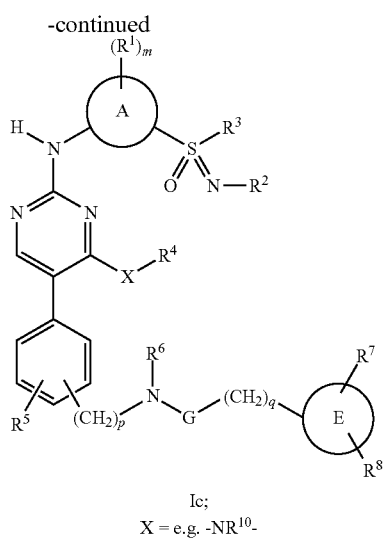

Ic;
X = e.g. -NR$^{10}$-

More specifically, compounds of the formula I in which —X—R$^4$ represents a thioether, e.g. —S—C$_1$-C$_6$-alkyl or —S—(CH$_2$)$_u$-aryl, as in formula Ia, may be oxidised by an appropriate agent, such as meta-chloroperbenzoic acid or Oxone®, to form the corresponding sulfoxide and/or sulfone of general formula Ib, which is then readily displaced by a suitable nucleophile NHR$^4$ (7a), which may be exemplified but is not limited to a primary or secondary amine of the formula HNR$^4$R$^{10}$, to give compounds of the formula Ic.

Experimental Section

In the subsequent paragraphs general procedures for the synthesis of the below mentioned intermediates and specific example compounds are summarised.

General Procedure 1 (GP1): Reduction of Nitroarenes or Nitroheteroarenes with Activated Iron The respective nitro compound (1.0 eq) was added to a stirred mixture of powdered iron (12 eq) in 85% ethanol (5 mL per mmol nitro compound) and concentrated hydrochloric acid (10 µL per mmol nitro compound) at room temperature. Subsequently, the mixture was stirred at 60° C. until all starting material was consumed (typically after about 3 h). After cooling to room temperature, the mixture was filtered, and the filter cake was repeatedly washed with hot ethanol. The filtrate was evaporated and purified by column chromatography to give the desired amine.

General Procedure 2 (GP2): Coupling of Anilines to 2-chloropyrimidines

The respective 2-chloropyrimidine (1 eq.) and the respective aniline (1.05 eq.) were dissolved in wet (10%) acetonitrile (~0.3 M), treated with 5N HCl/dioxane solution (~0.2 mL per mmol 2-chloropyrimidine), heated to 50° C. and stirred at this temperature until TLC indicated complete turnover. Then the reaction mixture was poured into aq. NaHCO$_3$ solution (with 0.5 g Na$_2$SO$_3$ added per 1 L NaHCO$_3$ solution). The mixture was extracted with EtOAc or CHCl$_3$, the combined organic layers were dried and evaporated to dryness. The analytically pure coupling products were isolated either by crystallization from acetonitrile or preparative HPLC purification.

General Procedure 3 (GP3): Urea Formation

A solution of the respective amino-substituted phenylboronic acid pinacolate ester in DCM (5 mL per mmol boronic ester) was treated with the respective isocyanate (1.05 eq.), followed by TEA (1.1 eq.) at room temperature under an atmosphere of nitrogen. The resulting mixture was stirred overnight and then analysed by TLC. If the reaction did not reach completion after 20 h, additional reagents (isocyanate, 0.26 eq.; and TEA, 0.28 eq.) were supplemented and stirring was continued until the reaction was complete according to TLC. After evaporation to dryness, the target compounds were purified either by trituration or by flash column chromatography.

General Procedure 4 (GP4): Sulfonamide Formation

A solution of the respective amino-substituted phenylboronic acid pinacolate ester in DCM (5 mL per mmol boronic ester) was treated with the respective sulfonyl chloride (1.05 eq.), followed by pyridine (1.1 eq.) at room temperature under an atmosphere of nitrogen and stirred overnight. After evaporation to dryness, the target compounds were purified either by trituration or by flash column chromatography.

General Procedure 5 (GP5): Amide Formation

The respective amino-substituted phenylboronic acid pinacolate ester (1.0 eq.) and the respective carboxylic acid chloride (1.5 eq.; prepared from the respective carboxylic acid by treatment with thionyl chloride followed by concentration in vacuo) were stirred in pyridine (0.2 M) at room temperature for 2 days. The volatiles were removed in vacuo, the residue was taken up in dichloromethane and the desired amides were crystallized by addition of hexane or purified by flash column chromatography.

General Procedure 6 (GP6): Suzuki Coupling (Conditions A)

The respective 5-iodopyrimidine (for example Intermediates 8 or 9; 1 eq.) and the respective phenyl boronic acid pinacolate ester (for example Intermediates 12-13 or 15-19; 1.4 eq.) together with Pd(PPh$_3$)$_4$ (6 mol %) were placed into a CEM microwave vial. After addition of toluene (8-10 mL per mmol halopyrimidine), EtOH (8-10 mL per mmol halopyrimidine) and aq. Na$_2$CO$_3$ solution (1M; 1.8-2.0 eq.) the vial was purged with argon and sealed. The resulting mixture was heated to 120° C. for 15 min in a CEM Explorer microwave reactor. The reaction mixture was diluted with DCM, quenched with water. The aqueous layer was extracted with DCM, the combined organic layers were washed with brine, dried and concentrated in vacuo. Flash column chromatography optionally followed by trituration e.g. with diisopropylether or preparative HPLC purification provided the analytically pure example compounds.

General Procedure 7 (GP7): Suzuki Coupling (Conditions B)

The respective 5-halopyrimidine (1 eq.) and the respective phenyl boronic acid pinacolate ester (1.1-1.5 eq.) together with tris-(2-furyl)-phosphine (0.36 eq.) were dissolved in dry DME and the resulting solution was degassed with argon several times. 1M aq. Na$_2$CO$_3$ solution (1.5 eq.) was added and the resulting solution was again degassed with argon. After addition of Pd(PPh$_3$)$_4$ (4.5 mol %) the mixture was refluxed until TLC indicated complete consumption of the starting 5-halopyrimidine (in cases of incomplete conversion after 24 h, additional amounts of catalyst, pinacolate ester and base were added and refluxing was continued). The reaction mixture was cooled to rt, poured into aq. NaHCO$_3$ solution and extracted with DCM. The combined organic extracts were washed with water and brine, dried and concentrated in vacuo. The residue was treated with boiling hexane and crystallized from EtOH.

General Procedure 8 (GP8): In Situ Sulfide Oxidation—Amine Displacement

To a solution of the respective pyrimidin-4-yl thioether (1 eq.) in N-methylpyrrolidin-2-one (0.1 M) was added meta-chloroperbenzoic acid (1.5 eq.) and the mixture was stirred for 1 h at room temperature. Subsequently, triethylamine (2.5 eq.) and the respective nucleophile, e.g. an amine was added and the mixture was stirred at 90° C. The reaction was monitored by TLC and was typically completed within 3 to 6 hours. After cooling to room temperature, water was added and the mixture was extracted with ethyl acetate. The combined organic layers were washed with brine, dried, and concentrated in vacuo. The crude products were purified by flash column chromatography, optionally followed by recrystallisation from a suitable solvent, e.g. diethyl ether.

General Procedure 9 (GP9): Cleavage of Ethoxycarbonyl Group

The respective N-ethoxycarbonyl sulfoximine (1 eq.) was dissolved in EtOH (8-16 mL per mmol sulfoximine) and treated with 3-4 eq. of NaOEt solution (20% in EtOH). The resulting mixture was stirred at reflux until TLC indicated complete turnover (usually after 4-6 hours). The reaction mixture was concentrated, the residue dissolved in DCM and quenched with water. The aqueous layer was extracted with DCM, the combined organic layers were washed with brine, dried and concentrated in vacuo. Flash column chromatography optionally followed by trituration or preparative HPLC purification yielded the analytically pure target compounds.

Alternatively to heating e.g. in an oil bath, the reaction can also be accomplished in a microwave oven at a temperature of 100° C., the reaction is then typically complete after 15 to 30 minutes.

Preparation of Intermediates

Intermediate 1: Preparation of 2,4-dichloro-5-iodopyrimdine

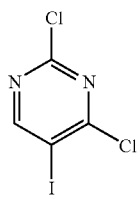

To a suspension of 5-iodouracil (10.0 g; 42 mmol) in N,N-dimethylaniline (11.0 mL) was added POCl$_3$ (64.4 g, 39.2 mL, 420 mmol). The resulting mixture was heated to 90° C. and was stirred at this temperature for 90 min. After cooling to room temperature, excess POCl$_3$ was evaporated and the residue was poured into a mixture of water and ice. After 2 h, the crystalline precipitate was isolated by filtration and washed with water. The crude product was then dissolved in ethyl acetate and the resulting solution was extracted with aqueous sodium bicarbonate and aqueous sodium sulfite. After drying over sodium sulfate, the solvent was evaporated and the residue was purified by column chromatography to give the title compound (10.6 g, 92% yield).

$^1$H-NMR (400 MHz, CDCl$_3$): 8.90 (s, 1H).

Intermediate 2: Preparation of (R)-2-(2-chloro-5-iodopyrimdin-4-ylamino)propan-1-ol

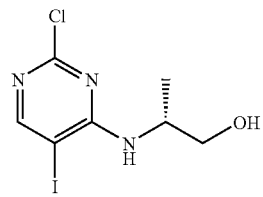

To a solution of 2,4-dichloro-5-iodopyrimidine (3.0 g; 10.9 mol) in acetonitrile (35 mL) was added triethylamine (1.32 g, 1.82 mL, 13.1 mmol), followed by (R)-2-aminopropanol (0.88 g, 11.8 mmol). The mixture was stirred at room temperature for 24 h and was then diluted with ethyl acetate, followed by extraction with brine, 10% aqueous citric acid, and aqueous sodium bicarbonate. After drying over sodium sulfate, the solvent was evaporated and the residue was purified by column chromatography to give the title compound (3.0 g, 88% yield).

$^1$H-NMR (300 MHz, DMSO): 8.30 (s, 1H); 6.56 (d, 1H); 4.86 (t, 1H); 4.50-4.15 (m, 1H); 3.35-3.45 (m, 2H); 1.10 (d, 3H).

Intermediate 3: Preparation of (RS)-S-(3-nitrophenyl)-S-methyl sulfoxide

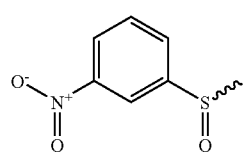

A solution of 3-nitro thioanisol (96 g, 568 mmol) in DCM (100 mL) was added dropwise to a cooled solution of sulfuryl chloride (96 g, 711 mmol) in DCM (600 mL) at −60° C. The mixture was stirred for 4 h at −20° C., then cooled to −60° C., and 350 mL of EtOH were carefully added. The reaction was then allowed to warm up to rt, subsequently, most of the solvent was evaporated, the residue was poured in sat. aq. NaHCO$_3$, and the solid product was filtered off and carefully washed with hexane on the filter, then air-dried to give the desired sulfoxide (95 g, 90% yield).

$^1$H-NMR (300 MHz, CDCl$_3$): 8.51 (s, 1H); 8.38 (d, 1H); 8.03 (d, 1H); 7.78 (t, 1H); 2.62 (s, 3H).

Intermediate 4: Preparation of (RS)-S-(3-nitrophenyl)-N-(ethoxycarbonyl)-S-methyl sulfoximide

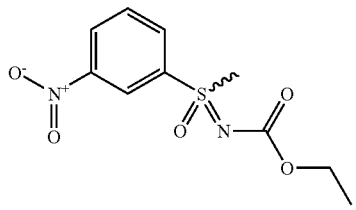

Step 1

In a 1000-mL three-necked flask equipped with reflux condenser, dropping funnel and mechanical stirrer, a mixture of (RS)-S-(3-nitrophenyl)-S-methyl sulfoxide (95 g, 513 mmol), sodium azide (36 g, 553 mmol) and DCM (600 mL) was cooled to 0° C. Subsequently, conc. $H_2SO_4$ (130 mL) was slowly added. The mixture then was carefully warmed to 45° C. and stirred at this temperature for 24 h. After cooling to room temperature, the mixture was poured on ice and then basified to pH 11 by NaOH. The DCM layer was separated, and the aqueous solution was extracted three more times with DCM. The organic layers were combined, dried over sodium sulfate and evaporated. TLC indicated ~30% unreacted sulfoxide, LCMS analysis showed ~50% conversion to the target product at this point in time. Further acylation was set up without purification.

Step 2

The crude product mixture from the previous stage (crude weight ~90 g) was dissolved in 300 mL of dry pyridine and treated with ethyl choroformiate (25 mL, 261 mmol) at room temperature. After 10 min, TLC indicated completion of the reaction. The mixture was poured into 1000 mL of water, acidified with aqueous hydrogen chloride to pH 3, extracted with ethyl acetate, dried over sodium sulfate and evaporated. The crude product was purified by column chromatography, followed by crystallisation from ethyl acetate and washing with hexane to give the desired product (72 g, 52% overall yield) and unreacted sulfoxide (23 g).

$^1$H-NMR (300 MHz, $CDCl_3$): 8.84 (s, 1H); 8.56 (d, 1H); 8.34 (d, 1H); 7.85 (t, 1H); 4.02-4.18 (m, 2H); 3.36 (s, 3H); 1.24 (t, 3H).

Intermediate 5: Preparation of (RS)-S-(3-aminophenyl)-N-(ethoxycarbonyl)-S-methyl sulfoximide

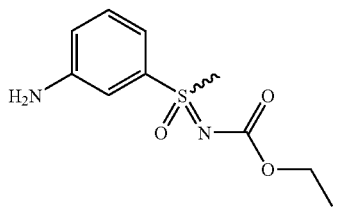

Intermediate 5 was prepared according to GP1 from (RS)-S-(3-nitrophenyl)-N-(ethoxycarbonyl)-S-methyl sulfoximide (4.8 g, 17.6 mmol) to give 4.2 g of the desired amine (98% yield).

$^1$H-NMR (300 MHz, $CDCl_3$): 7.24 (t, 1H); 7.03-7.08 (m, 1H); 6.95 (d, 1H); 6.81 (dd, 1H); 5.60-5.80 (m, 2H); 3.80-3.96 (m, 2H); 3.31 (s, 3H); 1.06 (t, 3H).

Intermediate 6: Preparation of (RS)-S-(4-nitrophenyl)-N-(ethoxycarbonyl)-S-methyl sulfoximide

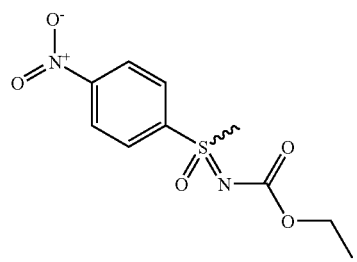

Step 1

In a 1000-mL three-necked flask equipped with reflux condenser, dropping funnel and mechanical stirrer, a mixture of (RS)-S-(4-nitrophenyl)-S-methyl sulfoxide (60 g, 324 mmol), sodium azide (23 g, 356 mmol) and DCM (600 mL) was cooled to 0° C. Subsequently, conc. $H_2SO_4$ (70 mL) was slowly added. The mixture then was carefully warmed to 45° C. and stirred at this temperature for 20 h. After cooling to room temperature, the mixture was poured on ice and then basified to pH 11 by NaOH. The DCM layer was separated, and the aqueous solution was extracted three more times with DCM. The organic layers were combined, dried over sodium sulfate and evaporated.

Step 2

The crude product mixture from the previous stage was dissolved in 400 mL of dry pyridine and treated with ethyl choroformiate (20 mL, 209 mmol) at room temperature. After 10 min, TLC indicated completion of the reaction. The mixture was poured into 1000 mL of water, acidified with aqueous hydrogen chloride to pH 3, extracted with ethyl acetate, dried over sodium sulfate and evaporated. The crude product was purified by column chromatography, followed by crystallisation from ethyl acetate and washing with hexane to give the desired product (20 g, 23% overall yield) and unreacted sulfoxide (25 g).

$^1$H-NMR (300 MHz, $CDCl_3$): 8.49 (d, 2H); 8.23 (d, 2H); 4.01-4.18 (m, 2H); 3.37 (s, 3H); 1.26 (t, 3H).

Intermediate 7: Preparation of (RS)-S-(4-aminophenyl)-N-(ethoxycarbonyl)-S-methyl sulfoximide

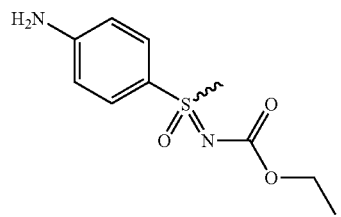

Intermediate 7 was prepared according to GP1 from (RS)-S-(4-nitrophenyl)-N-(ethoxycarbonyl)-S-methyl sulfoximide (20 g, 62 mmol) to give the desired amine in 90% yield.

¹H-NMR (300 MHz, CDCl₃): 7.58-7.80 (m, 2H); 6.55-6.73 (m, 2H); 4.43 (s br, 2H); 3.98-4.18 (m, 2H); 3.23 (s, 3H); 1.15-1.29 (m, 3H).

Intermediate 8: Preparation of (RS)-N-(Ethoxycarbonyl)-S-(3-{[4-{[(R)-2-(hydroxy-1-methylethyl]amino}-5-iodopyrimidin-2-yl]amino}phenyl)-S-methylsulfoximide

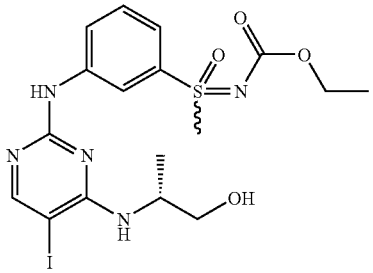

Intermediate 8 was prepared in analogy to GP 2 by reaction of 25 g of Intermediate 2 and 20 g of Intermediate 5 to yield (after preparative HPLC purification) 12 g of Intermediate 8 (29% yield).

¹H-NMR (300 MHz, DMSO): 9.75 (s, 1H); 8.62 (s, 1H); 8.20 (s, 1H); 7.87 (d, 1H); 7.54 (t, 1H); 7.43 (d, 1H); 6.03 (d, 1H); 4.90-4.95 (m, 1H); 4.25-4.35 (m, 1H); 3.85-3.95 (m, 2H); 3.45-3.55 (m, 2H); 3.30 (s, 3H); 1.15 (d, 3H); 1.08 (t, 3H).

Intermediate 9: Preparation of (RS)-S-(3-{[4-{[(R)-2-(Hydroxy-1-methylethyl]amino}-5-iodopyrimidin-2-yl]amino}phenyl)-S-methylsulfoximide

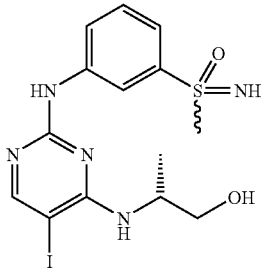

Intermediate 9 was prepared in analogy to GP 9 from intermediate 8 (1.0 eq.) and sodium ethoxide (3.0 eq.) in 62% yield.

¹H-NMR (300 MHz, DMSO): 9.56 (s br, 1H); 8.59 (d, 1H); 8.14 (s, 1H); 7.66-7.74 (m, 1H); 7.37-7.44 (m, 2H); 5.93 (mc, 1H); 4.90-4.98 (m, 1H); 4.29 (mc, 1H); 4.07-4.14 (m, 1H); 3.39-3.54 (m, 2H); 2.99 (s, 3H); 1.16 (d br, 3H).

MS (ESI): [M+H]⁺=448.

Intermediate 10: Preparation of (RS)-N-(Ethoxycarbonyl)-S-(4-{[4-{[(R)-2-(hydroxy-1-methylethyl]amino}-5-iodopyrimidin-2-yl]amino}phenyl)-S-methylsulfoximide

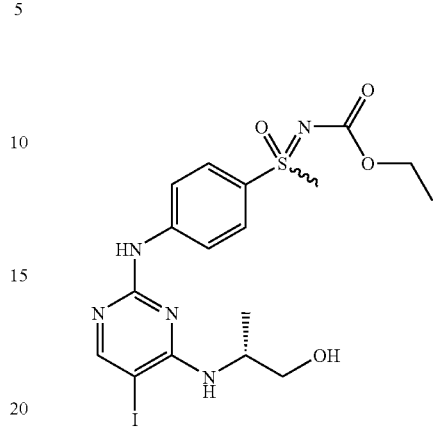

Intermediate 10 was prepared in analogy to GP 2 by reaction of 25 g of Intermediate 2 and 20 g of Intermediate 7 to yield (after preparative HPLC purification) 15 g of Intermediate 10 (45% yield).

¹H-NMR (300 MHz, DMSO): 9.84 (s, 1H); 8.31 (s, 1H); 8.22 (s, 1H); 7.98 (d, 2H); 7.80 (d, 2H); 6.05 (d, 1H); 4.95 (s br, 1H); 4.20-4.25 (m, 1H); 3.90 (q, 2H); 3.50-3.55 (m, 2H); 3.40 (s, 3H); 1.20 (d, 3H); 1.10 (t, 3H).

Intermediate 11: Preparation of (RS)-S-(4-{[4-{[(R)-2-(Hydroxy-1-methylethyl]amino}-5-iodopyrimidin-2-yl]amino}phenyl)-S-methylsulfoximide

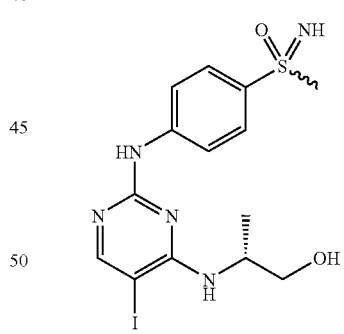

Intermediate 11 was prepared in analogy to GP 9 by treating 3.00 g (5.78 mmol) of Intermediate 10 with 6.4 mL NaOEt solution (21%; 17.4 mmol, 3 eq.) in 96 mL EtOH and heating to 100° C. for 15 min under microwave irradiation yielding 2.73 g of the desired product (quantitative yield).

¹H-NMR (300 MHz, DMSO): 9.66 (s, 1H); 8.17 (s, 1H); 7.88 (d, 2H); 7.74 (d, 2H); 5.99 (d, 1H); 4.93 (br. s, 1H); 4.18 (mc, 1H); 3.94 (s, 1H); 3.46-3.52 (m, 2H); 2.97 (s, 3H); 1.17 (d, 3H).

MS (ESI): [M+H]⁺=448.

Intermediate 12: Preparation of 5-Bromo-2-chloro-4-methylsulfanyl-pyrimidine

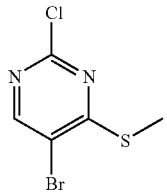

2 g of MeSNa (28.5 mmol; 1 eq.) and 6.5 g of 5-bromo-2,4-dichloropyrimidine (28.5 mmol, 1 eq.) were stirred in 50 mL dry acetonitrile at rt for 24 h. Then the mixture was poured into water, extracted with DCM, dried (Na$_2$SO$_4$) and evaporated to dryness. The product was recrystallized from hexane to yield 4 g of Intermediate 12 (70% yield).
$^1$H-NMR (400 MHz, CDCl$_3$): 8.31 (s, 1H); 2.59 (s, 3H).

Intermediate 13: Preparation of (RS)-N-(Ethoxycarbonyl)-S-(3-{[5-bromo-4-(methylsulfanyl)pyrimidin-2-yl]amino}phenyl)-S-methylsulfoximide

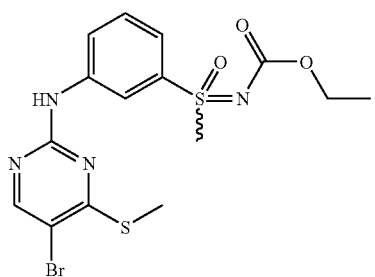

Intermediate 13 was prepared in analogy to GP 2 by reaction of 2.15 g of Intermediate 12 (4.5 mmol, 1 eq.) and 1.09 g of Intermediate 5 (4.5 mmol, 1 eq.) to yield (after crystallization from acetonitrile) 1.2 g of Intermediate 13 (60% yield).
$^1$H-NMR (300 MHz, DMSO): 10.25 (s, 1H); 8.60 (s, 1H); 8.40 (s, 1H); 7.90 (d, 1H); 7.58 (t, 1H); 7.50 (d, 1H); 3.84-3.96 (m, 2H); 3.40 (s, 3H); 2.55 (s, 3H); 1.10 (t, 3H).

Intermediate 14: Preparation of (RS)-N-(Ethoxycarbonyl)-S-(3-{[5-bromo-4-(methoxy)pyrimidin-2-yl]amino}phenyl)-S-methylsulfoximide

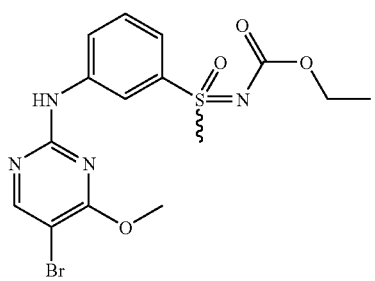

Intermediate 14 was prepared in analogy to GP 2 by reaction of Intermediate 5 (1.73 g, 7.16 mmol) with commercial 5-bromo-2-chloro-4-methoxypyrimidine (2.00 g, 8.95 mmol, 1.25 eq) to give 1.33 g (43% yield) of the title compound (after crystallization from acetonitrile and column chromatography of the mother liquor residue).
$^1$H-NMR (DMSO, 300 MHz): 10.21 (s, 1H); 8.67 (s br, 1H); 8.42 (s, 1H); 7.82 (d, 1H); 7.56 (t, 1H); 7.48 (d, 1H); 4.02 (s, 3H); 3.88 (mc, 2H); 3.38 (s, 3H); 1.04 (t, 3H).
MS (ESI): [M+H]$^+$=429 ($^{79}$Br).

Intermediate 14a: Preparation of (RS)-S-(3-{[5-bromo-4-(methoxy)pyrimidin-2-yl]amino}phenyl)-S-methylsulfoximide

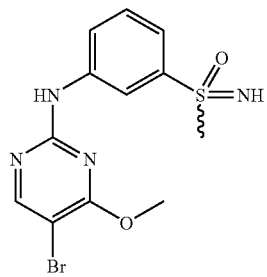

Intermediate 14a was prepared in analogy to GP 9 by reaction of Intermediate 14 (500 mg (1.16 mmol) to give, aside a larger quantity of the corresponding 4-ethoxypyrimidine, 14 mg (3%) of the desired product.
$^1$H-NMR (DMSO, 300 MHz): 10.13 (s, 1H); 8.62 (s br, 1H); 8.40 (s, 1H); 7.74-7.81 (m, 1H); 7.50 (d, 2H); 4.02 (s, 3H); 3.09 (s, 3H); =NH not displayed.
MS (ESI): [M+H]$^+$=357 ($^{79}$Br).

Intermediate 15: Preparation of (RS)-N-(Ethoxycarbonyl)-S-(3-{[5-(4-amino-3-fluorophenyl)-4-(methoxy)-pyrimidin-2-yl]amino}phenyl)-S-methylsulfoximide

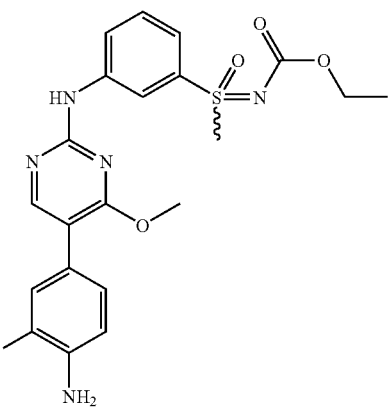

To a degassed suspension of Intermediate 14 (687 mg, 1.60 mmol), Intermediate 21 (vide infra, 474 mg, 2.00 mmol, 1.25 eq.), and tris-(2-furyl)-phosphine (149 mg, 0.64 mmol, 0.40 eq) in a mixture of dimethoxyethane (22 mL) and 1 M aq. sodium carbonate (2.56 mL) was added Pd$_2$(dba)$_3$ (73 mg, 0.08 mmol, 0.05 eq). The resulting mixture was immersed into an oil bath pre-heated to 100° C. and then stirred at said temperature for 6 h. After cooling to room temperature, water was added (20 mL), followed by extraction with ethyl acetate (3×50 mL). The combined organic layers were dried over MgSO₄ and evaporated. The crude residue was purified by column chromatography to give 280 mg (38% yield) of the title compound.

¹H-NMR (DMSO, 400 MHz): 10.07 (s, 1H); 8.76 (s, 1H); 8.39 (s, 1H); 7.83 (d, 1H); 7.54 (t, 1H); 7.44 (d, 1H); 7.21 (dd, 1H); 7.08 (mc, 1H); 6.76 (mc, 1H); 5.22 (s br, 2H); 4.00 (s, 3H); 3.88 (mc, 2H); 3.38 (s, 3H); 1.05 (t, 3H).

MS (ESI): [M+H]⁺=460.

Intermediate 16: Preparation of (RS)-S-(3-nitrophenyl)-N-(isopropylcarbamoyl)-S-methylsulfoximide

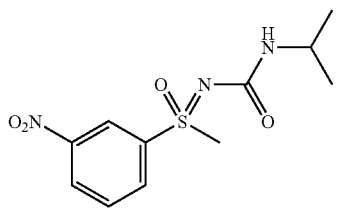

8.24 g (41.2 mmol) (RS)-S-(3-nitrophenyl)-S-methylsulfoximide (Intermediate 4, step 1) in 370 ml toluene were treated with 13.6 mL (138.3 mmol) isopropyl isocyanate. The mixture was stirred under argon at 104° C. for 5 hours and at room temperature for 60 hours. 4.5 mL (46 mmol) isopropyl isocyanate were added and the mixture was stirred under argon at 104° C. for 6 hours and at room temperature for 16 hours. 4.5 ml (46 mmol) isopropyl isocyanate were added and the mixture was stirred under argon at 104° C. for 7 hours and at room temperature for 17 hours. The mixture was cooled with ice for 40 minutes.

The suspension was filtered to give 9.2 g (78% yield) of the product.

¹H-NMR (300 MHz, DMSO): 8.63 (s, 1H); 8.54 (d, 1H); 8.35 (d, 1H), 7.96 (t, 1H); 7.01 (d, 1H); 3.57 (m, 1H); 3.46 (s, 3H); 1.00 (m, 6H).

Intermediate 17: Preparation of (RS)-S-(3-aminophenyl)-N-(isopropylcarbamoyl)-S-methylsulfoximide

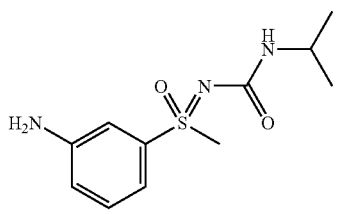

18.6 g iron powder in 198 mL ethanol and 1.93 mL conc. aq. hydrochloric acid were stirred for 30 minutes at room temperature. 7.8 g (27.3 mmol) (RS)-S-(3-nitrophenyl)-N-(isopropylcarbamoyl)-S-methylsulfoximide in 20 mL methanol were added. The mixture was stirred at 60° C. for 2 hours and filtered over a bed of silica gel. The residue was washed with hot ethanol. The combined filtrates were evaporated. The crude residue was purified by column chromatography (silica gel, dichloromethane:dichloromethane/ethanol 1:1) to give 4.53 g (65% yield) of the title compound.

¹H-NMR (300 MHz, DMSO): 7.23 (t, 1H); 7.07 (s, 1H); 6.97 (d, 1H); 6.80 (d, 1H); 6.75 (d, 1H); 5.65 (s br, 2H); 3.60 (m, 1H); 3.27 (s, 3H); 1.00 (m, 6H)

Intermediate 18: Preparation of (RS)-S-(3-[4-((R)-2-Hydroxy-1-methyl-ethylamino)-5-iodo-pyrimidin-2-ylaminophenyl])-N-(isopropylcarbamoyl)-S-methylsulfoximide

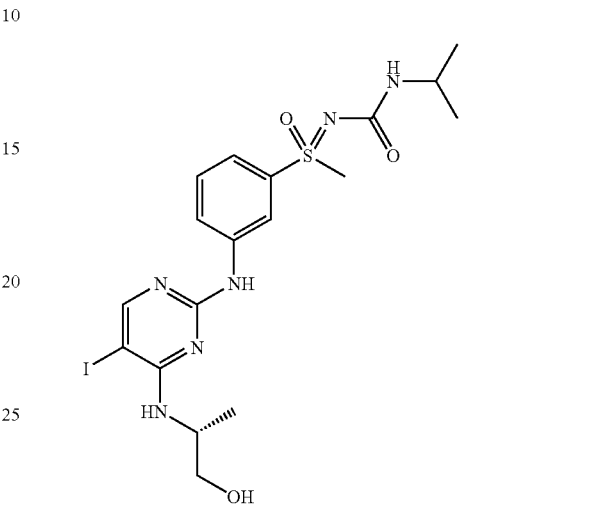

1.62 g (5.17 mmol) (R)-2-(2-Chloro-5-iodo-pyrimidin-4-ylamino)-propan-1-ol and 1.2 g (4.7 mmol) (RS)-S-(3-aminophenyl)-N-(isopropylcarbamoyl)-S-methylsulfoximide in 14.8 mL acetonitrile were treated with 1.17 mL 4 N hydrochloric acid (4.7 mmol) and stirred in a pressure tube at 52° C. for 20 hours. 10 mL 2 N ammonia in methanol were added and the mixture was stirred for 20 minutes. The mixture was concentrated and purified by column chromatography to give 2.11 g (84% yield) of the title compound.

¹H-NMR (300 MHz, DMSO): 9.66 (s, 1H); 8.57 (s, 1H); 8.19 (s, 1H); 7.81 (d, 1H); 7.49 (t, 1H); 7.41 (d, 1H); 6.79 (m, 1H); 5.99 (m, 1H); 4.93 (m, 1H); 4.28 (m, 1H); 3.59 (m, 1H); 3.52 (m, 2H); 3.32 (d, 3H); 1.19 (d, 3H); 1.00 (m, 6H).

Intermediate 19: Preparation of N-[4-(4,4,5,5-tetramethyl-1,3,2-dioxaborolan-2-yl)phenyl]-N'-[3-(trifluoromethyl)-phenyl]urea

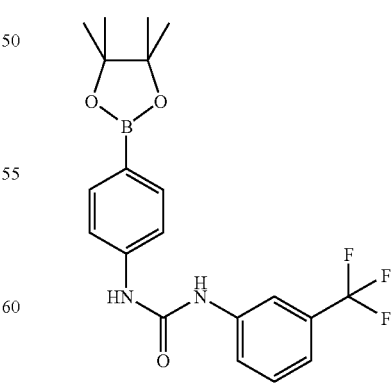

Intermediate 19 was prepared in analogy to GP 3 by reaction of 4-(4,4,5,5-tetramethyl-[1,3,2]dioxaborolan-2-yl)-phenylamine with 1-isocyanato-3-trifluoromethylbenzene.

$^1$H-NMR (CDCl$_3$, 300 MHz): 7.74 (d, 2H); 7.58-7.68 (m, 1H): 7.16-7.55 (m, 7H); 1.32 (s, 12H).

MS (ESI): [M+H]$^+$=407.

The following boronic acid pinacolate ester was prepared according to general procedure GP 3 in analogy to Intermediate 19 from 4-(4,4,5,5-tetramethyl-[1,3,2]dioxaborolan-2-yl)-phenylamine and the appropriate phenyl isocyanate.

| Intermediate No | Structure | Name | Analytical data |
|---|---|---|---|
| 20 | 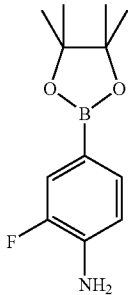 | N-phenyl-N'-[4-(4,4,5,5-tetramethyl-1,3,2-dioxaborolan-2-yl)phenyl]urea | MS (ESI): [M + H]$^+$ = 339. |

Intermediate 21: Preparation of 2-Fluoro-4-(4,4,5,5-tetramethyl-[1,3,2]dioxaborolan-2-yl)-phenylamine Route A (Metallation)

Step 1

50 g of 4-bromo-2-fluoroaniline (263 mmol) and 70 g of Boc$_2$O (321 mmol) were dissolved in tert-BuOH (140 mL) and stirred at 50° C. overnight. TLC indicated completeness of reaction. The solvent was mainly (~⅔) evaporated, then 150 mL of 50% MeOH was added and subsequently 15 mL of conc. NH$_3$. After 30 min stirring the oily lower layer was separated, washed with 50% MeOH, concentrated in vacuo and the product crystallized upon cooling. Then the product was filtered off, the filtrate was dissolved in benzene, extracted with 3% HCl, then evaporated and an additional portion of BOC-aniline crystallized by dilution with 75% EtOH (total yield: 55 g, 190 mmol, 72%).

$^1$H-NMR (DMSO, 300 MHz): 9.10 (s, 1H); 7.58 (t, 1H); 7.51 (dd, 1H); 7.33 (dd, 1H); 1.45 (s, 9H).

Step 2

The solution of the product from step 1 (25 g, 86 mmol) in THF (400 mL), was cooled to −85° C., and then treated dropwise with 83 mL of 2.5 M n-BuLi (208 mmol). The mixture was stirred for 1 h, and quenched with trimethylborate (27 g, 260 mmol) at −90° C. The viscous mixture was gradually warmed to rt, poured into 1 L of water, extracted with benzene (50 mL) and evaporated. The aqueous layer was neutralized with acetic acid, upon which the precipitated oil slowly started to crystallize. The precipitate was filtered off, washed with water and air-dried yielding 15 g of the boronic acid. The aqueous filtrate was extracted with EtOAc, the organic layers were combined, dried and evaporated to dryness. Flash column chromatography (PhH-PhH:EtOH 3:1) yielded another batch of the boronic acid (1.2 g) improving the combined yield to 74% (64 mmol).

$^1$H-NMR (DMSO, 300 MHz): 9.00 (s, 1H); 8.20 (br. s, 2H); 7.62 (t, 1H); 7.48-7.54 (m, 2H); 1.50 (s, 9H).

Step 3

15 g of the boronic acid from step 2 (59 mmol) and 14 g pinacol (118 mmol) were stirred in MeOH at rt for 1 h. TLC indicated complete conversion, water (45 mL) was added to the reaction mixture, and the precipitated oil started crystallizing after trituration. The precipitate was filtered, washed with 70% MeOH, and dried (16 g, 48 mmol, yield: 81%).

$^1$H-NMR (DMSO, 300 MHz): 9.11 (s, 1H); 7.73 (t, 1H); 7.38 (d, 1H); 7.28 (d, 1H); 1.43 (s, 9H); 1.25 (s, 12H).

Step 4

A solution of the BOC-derivative from step 3 (3.6 g, 10.6 mmol) in 35 mL DCM and 10 mL of 5N HCl in dioxane was stirred at 30° C. for 1.5 h. TLC indicated 80% conversion. Additional 5 mL of HCl/dioxane were added, and stirring was continued for 1 h. The solvent was evaporated, the residue was treated with water, neutralized with NaHCO$_3$, and extracted with benzene. The combined organic layers were washed with water, evaporated to dryness, and the resulting oil was triturated with hexane to yield 1.29 g (5.4 mmol) of the boronic acid pinacolate ester (51%).

$^1$H-NMR (DMSO, 300 MHz): 7.12 (dd, 1H); 7.11 (dd, 1H); 6.68 (t, 1H); 5.53 (s br, 2H); 1.21 (s, 12H).

Route B (Pd-Catalyzed Borylation)

Step 1

570 mg 4-bromo-2-fluoroaniline (3 mmol, 1 eq.), 1.14 g bis(pinacolato)diboron (4.5 mmol, 1.5 eq.), 883 mg KOAc (9 mmol, 3 eq.) and 245 mg PdCl$_2$(dppf).CH$_2$Cl$_2$ (0.3 mmol, 0.1 eq.) were weighed into a dry (Schlenk) flask and set under an atmosphere of argon. 10.4 mL DMSO were added and the resulting reddish-purple solution was heated to 80° C. for 6.5 h. The mixture was diluted with EtOAc, quenched with water, and filtered through Celite. The layers were separated and the watery layer was extracted with EtOAc. The combined organic layers were washed with brine (2×), dried and concentrated in vacuo. The residue was purified by flash column chromatography to yield 661 mg of the desired product (90%), which contained pinacol as a slight impurity.

$^1$H-NMR (DMSO, 300 MHz): 7.12 (dd, 1H); 7.11 (dd, 1H); 6.68 (t, 1H); 5.53 (s br, 2H); 1.21 (s, 12H).

Intermediate 22: Preparation of 1-[2-Fluoro-4-(4,4,5,5-tetramethyl-[1,3,2]dioxaborolan-2-yl)-phenyl]-3-(2-fluoro-5-trifluoromethyl-phenyl)-urea

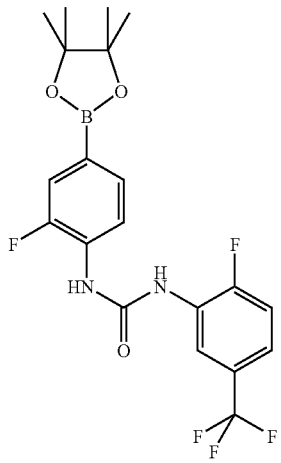

8.55 g (48 mmol) of 2-fluoro-5-trifluoromethylaniline and 4.8 g (48 mmol) of triethylamine were dissolved in 30 mL of dry DCM and added dropwise to a solution of 4.7 g (16 mmol) of triphosgene in 30 mL of DCM at 5-10° C. Within 20 min TLC indicated full consumption of the starting amine. This mixture was treated dropwise with a solution of 11.3 g (48 mmol) of 2-fluoro-4-(4,4,5,5-tetramethyl-[1,3,2]dioxaborolan-2-yl)-phenylamine and 4.8 g of triethylamine in 35 mL of DCM at room temperature. Then the reaction mixture was stirred for 2 h, poured into water, the organic layer was separated and evaporated. The residue was crystallized from 90% EtOH yielding 4.5 g of the target product. Flash column chromatography of the residue obtained from evaporation of the mother liquid yielded 2.7 g of the target material (combined yield 7.2 g; 34%).

$^1$H-NMR (DMSO, 300 MHz): 9.28 (br. s, 2H); 8.58 (dd, 1H); 8.12 (t, 1H); 7.56 (dd, 1H); 7.47 (dd, 1H); 7.31-7.40 (m, 2H).

Intermediate 23: Preparation of N-[4-(4,4,5,5-Tetramethyl-[1,3,2]dioxaborolan-2-yl)-phenyl]-benzenesulfonamide

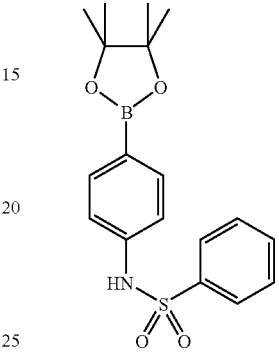

Intermediate 23 was prepared in analogy to GP 4 by reaction of 4-(4,4,5,5-tetramethyl-[1,3,2]dioxaborolan-2-yl)-phenylamine with benzenesulfonyl chloride.

$^1$H-NMR (CDCl$_3$, 400 MHz): 7.77-7.82 (m, 2H); 7.68 (d, 2H); 7.49-7.65 (m, 1H); 7.38-7.47 (m, 2H); 7.08 (d, 2H); 6.82 (s br, 1H); 1.32 (s, 12H).

MS (ESI): [M+H]$^+$=360; [2M+H]$^+$=719.

The following boronic acid pinacolate ester was prepared according to general procedure GP 4 from 4-(4,4,5,5-tetramethyl-[1,3,2]dioxaborolan-2-yl)-phenylamine and the appropriate phenyl sulfonyl chloride.

| Intermediate No | Structure | Name | Analytical data |
|---|---|---|---|
| 24 | ![structure] | 2,3-Dichloro-N-[4-(4,4,5,5-tetramethyl-1,3,2-dioxaborolan-2-yl)phenyl]-benzenesulfonamide | $^1$H-NMR (CDCl$_3$, 300 MHz): 7.87-7.93 (m, 2 H); 7.61 (d, 2 H); 7.51-7.57 (m, 2 H); 7.29 (t, 1 H); 6.98-7.07 (m, 3 H); 1.24 (s, 12 H). MS (ESI): [M + H]$^+$ = 428 |

Intermediate 25: Preparation of 2,3-Dichloro-N-[2-fluoro-4-(4,4,5,5-tetramethyl-[1,3,2]dioxaborolan-2-yl)-phenyl]-benzenesulfonamide

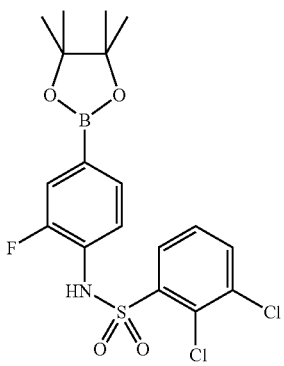

Intermediate 25 was prepared in analogy to GP 4 from 1.78 g 2-fluoro-4-(4,4,5,5-tetramethyl-[1,3,2]dioxaborolan-2-yl)-phenylamine (7.5 mmol) and 2.03 g 2,3-dichloro-benzenesulfonyl chloride (8.25 mmol, 1.1 eq.) in 20 mL DCM and in the presence of 0.66 mL pyridine (8.25 mmol, 1.1. eq.) yielding after trituration 2.42 g of the target compound (72% yield).

$^1$H-NMR (DMSO; 400 MHz): 10.81 (s, 1H); 7.90 (dd, 1H); 7.87 (dd, 1H); 7.48 (t, 1H); 7.36 (dd, 1H); 7.26-7.30 (m, 2H); 1.22 (s, 12H).

Intermediate 26: Preparation of 1-Phenyl-cyclopropanecarboxylic acid [4-(4,4,5,5-tetramethyl-[1,3,2]dioxaborolan-2-yl)-phenyl]-amide

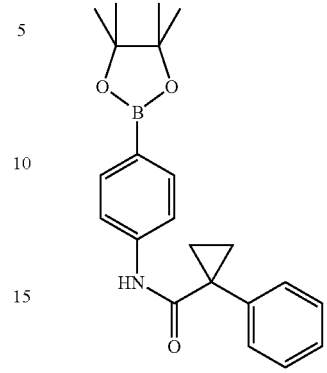

Intermediate 26 was prepared in analogy to GP 5 by reaction of 4-(4,4,5,5-tetramethyl-[1,3,2]dioxaborolan-2-yl)-phenylamine with 1-phenyl-cyclopropanecarboxylic acid.

$^1$H-NMR (DMSO, 300 MHz): 9.09 (s, 1H); 7.52 (br. s 4H); 7.22-7.38 (m, 5H); 1.39-1.43 (m, 2H); 1.23 (s, 12H); 1.06-1.10 (m, 2H).

MS (ESI): [M+H]$^+$=364.

The following boronic acid pinacolate esters were prepared in analogy to general procedure GP 5 from the respective borylated aniline and the appropriate carboxylic acid.

| Intermediate No | Structure | Name | Analytical data |
|---|---|---|---|
| 27 | 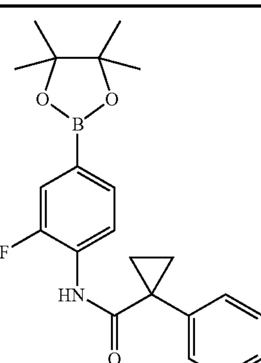 | N-[2-fluoro-4-(4,4,5,5-tetramethyl-1,3,2-dioxaborolan-2-yl)phenyl]-1-phenylcyclopropanecarboxamide | $^1$H-NMR (DMSO, 300 MHz): 8.13 (mc, 1 H); 7.98 (t, 1 H); 7.35-7.57 (m, 6 H); 7.31 (d, 1 H); 1.54 (mc, 2 H); 1.30 (s, 12 H); 1.18 (mc, 2 H). |
| 28 | 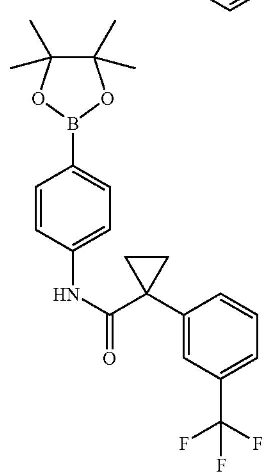 | N-[4-(4,4,5,5-tetramethyl-1,3,2-dioxaborolan-2-yl)phenyl]-1-[3-(trifluoromethyl)phenyl]-cyclopropane-carboxamide | $^1$H-NMR (CDCl$_3$): 7.56-7.80 (m, 7 H); 7.30-7.36 (d, 1 H); 6.92 (s, 1 H); 1.75-1.85 (mc, 2 H); 1.35 (s, 12 H); 1.15-1.25 (mc, 2 H). |

PREPARATION OF EXAMPLE COMPOUNDS

Example Compound 1

Preparation of N-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]phenyl}-1-phenylcyclopropanecarboxamide

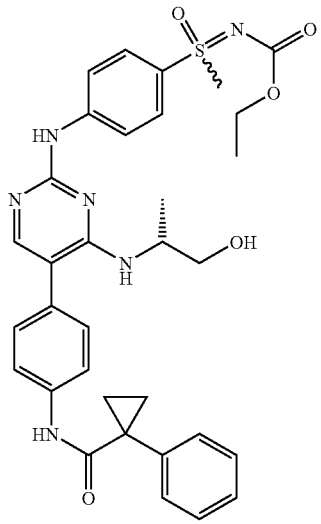

Example Compound 1 was prepared in analogy to GP 6 by reaction of 260 mg of Intermediate 10 (0.5 mmol, 1 eq.) with 258 mg of Intermediate 26 (0.71 mmol, 1.4 eq.) in the presence of 35 mg Pd(PPh$_3$)$_4$ (0.03 mmol; 6 mol %) and 0.96 mL 1M aq. Na$_2$CO$_3$ solution (1.9 eq.) in 8.2 mL toluene/EtOH (1:1). Microwave-heating to 120° C. for 15 min followed by work-up as described in GP 6 and flash column chromatography followed by trituration with diisopropyl ether provided 150 mg (0.24 mmol; 48% yield) of the target compound as a slightly yellowish solid.

$^1$H-NMR (DMSO, 400 MHz): 9.73 (s, 1H); 9.21 (s, 1H); 8.03 (d, 2H); 7.77 (s, 1H); 7.76 (d, 2H); 7.64 (d, 2H); 7.23-7.38 (m, 7H); 5.87 (d, 1H); 4.77 (t, 1H); 4.19-4.27 (m, 1H); 3.85-3.93 (m, 2H); 3.42 (t, 2H); 3.38 (s, 3H); 1.42 (m, 2H); 1.10-1.14 (m, 5H); 1.07 (t, 3H).

MS (ESI): [M+H]$^+$=629.

Example Compound 2

Preparation of 2,3-Dichloro-N-{4-[2-({3-[(RS)-N-(ethoxycarbonyl)-S-methylsulfonimidoyl]phenyl}amino)-4-{[(R)-2-hydroxy-1-methylethyl]amino}pyrimidin-5-yl]-phenyl}benzenesulfonamide

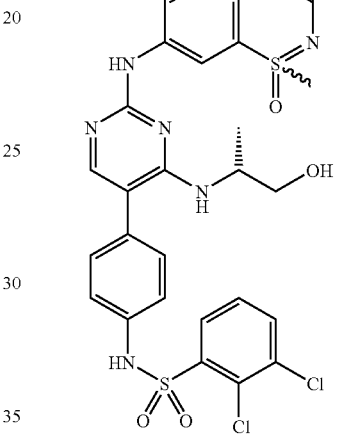

Example Compound 2 was prepared in analogy to GP 6 by reaction of 208 mg of Intermediate 8 (0.4 mmol, 1 eq.) with 243 mg of Intermediate 24 (0.57 mmol, 1.4 eq.) in the presence of 28 mg Pd(PPh$_3$)$_4$ (0.024 mmol; 6 mol %) and 0.77 mL 1M aq. Na$_2$CO$_3$ solution (1.9 eq.) in 6.6 mL toluene/EtOH (1:1). Microwave-heating to 120° C. for 15 min followed by work-up as described in GP 6 and flash column chromatography followed by trituration with diisopropyl ether provided 167 mg (0.24 mmol; 60% yield) of the target compound.

$^1$H-NMR (DMSO, 400 MHz): 10.96 (s, 1H); 9.60 (s, 1H); 8.60-8.67 (m, 1H); 8.09 (dd, 1H); 7.82-7.95 (m, 2H); 7.69 (s, 1H); 7.56 (t, 1H); 7.49 (t, 1H); 7.30-7.42 (m, 1H); 7.27 (d, 2H); 7.14 (d, 2H); 5.84 (d, 1H); 4.63-4.72 (m, 1H); 4.26 (mc, 1H); 3.80-3.93 (m, 2H); 3.32-3.47 (m, 5H); 1.00-1.11 (m, 6H).

MS (ESI): [M+H]$^+$=693 ($^{35}$Cl).

The following example compounds were prepared according to general procedure GP 6 from Intermediates 8, 10 18 and the respective phenyl boronic acid pinacolate ester:

| Example | Structure | Name | Analytical data |
|---|---|---|---|
| 3 | 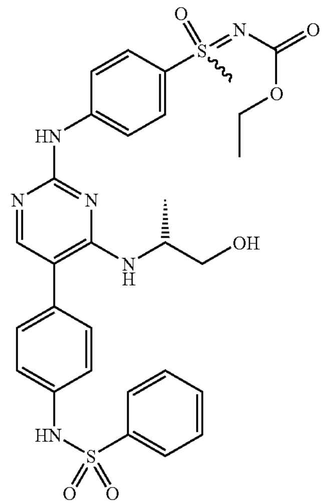 | N-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}benzene-sulfonamide | ¹H-NMR (DMSO, 300 MHz): 10.49 (s, 1 H); 9.73 (s, 1 H); 8.01 (d, 2 H); 7.81 (d, 2 H); 7.75 (d, 2 H); 7.72 (s, 1 H); 7.53-7.63 (m, 3 H); 7.26 (d, 2 H); 7.14 (d, 2 H); 5.89 (d, 1 H); 4.76 (t, 1 H); 4.17-4.26 (m, 1 H); 3.84-3.92 (m, 2 H); 3.39-3.46 (m, 2 H); 3.37 (s, 3 H); 1.10 (d, 3 H); 1.07 (t, 3 H). MS (ESI): [M + H]⁺ = 625. |
| 4 | 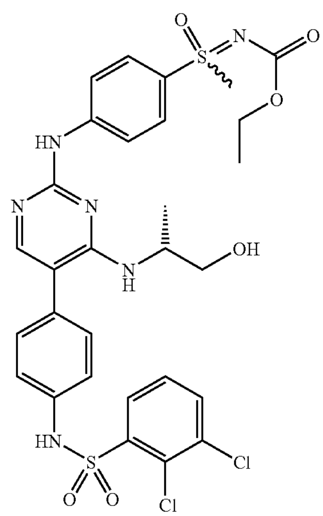 | 2,3-Dichloro-N-{4-[2-({4-[(RS)-N-(ethoxycarbonyl)-S-methylsulfonimidoyl]phenyl}amino)-4-{[(R)-2-hydroxy-1-methylethyl]amino}-pyrimidin-5-yl]-phenyl}benzene-sulfonamide | ¹H-NMR (DMSO, 300 MHz): 10.98 (s, 1 H); 9.72 (s, 1 H); 8.00 (d, 2 H); 7.91 (dd, 1 H); 7.75 (d, 2 H); 7.71 (s, 1 H); 7.56 (t, 1 H); 7.51 (d, 1 H); 7.27 (d, 2 H); 7.13 (d, 2 H); 5.93 (d, 1H); 4.74 (t, 1 H); 4.17-4.26 (m, 1 H); 3.83-3.93 (m, 2 H); 3.36-3.46 (m, 2 H); 3.37 (s, 3 H); 1.10 (d, 3 H); 1.06 (t, 3 H). MS (ESI): [M + H]⁺ = 693/695. |
| 5 | 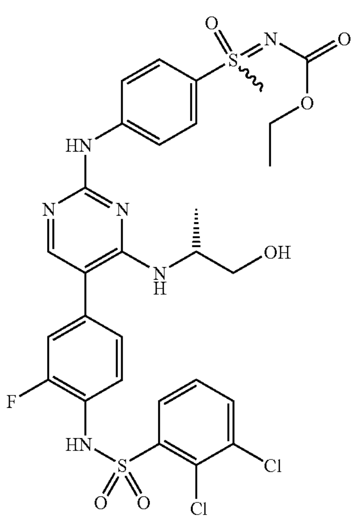 | 2,3-Dichloro-N-{4-[2-({4-[(RS)-N-(ethoxycarbonyl)-S-methylsulfonimidoyl]phenyl}amino)-4-{[(R)-2-hydroxy-1-methylethyl]amino}-pyrimidin-5-yl]-2-fluorophenyl}-benzenesulfonamide | ¹H-NMR (DMSO, 300 MHz): 10.69 (s, 1 H); 9.76 (s, 1 H); 8.01 (d, 2 H); 7.92 (dd, 1 H); 7.90 (d, 1 H); 7.77 (s, 1 H); 7.76 (d, 2 H); 7.50 (t, 1 H); 7.19-7.26 (m, 2 H); 7.11 (d, 1 H); 6.09 (d, 1 H); 4.74 (t, 1 H); 4.19-4.30 (m, 1 H); 3.83-3.94 (m, 2 H); 3.39-3.47 (m, 2 H); 3.37 (s, 3 H); 1.11 (d, 3 H); 1.07 (t, 3 H). MS (ESI): [M + H]⁺ = 711/713. |

| Example | Structure | Name | Analytical data |
|---|---|---|---|
| 6 | 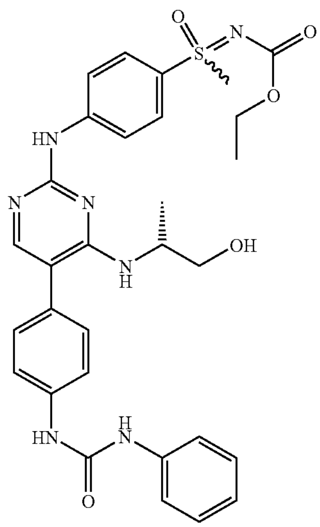 | 1-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[phenyl]urea | ¹H-NMR (DMSO, 300 MHz): 9.73 (s, 1 H); 8.79 (s, 1 H); 8.70 (s, 1 H); 8.04 (d, 2 H); 7.79 (s, 1 H); 7.77 (d, 2 H); 7.53 (d, 2 H); 7.44 (d, 2 H); 7.30 (d, 2 H); 7.25 (t, 2 H); 6.94 (t, 1 H); 5.92 (d, 1 H); 4.80 (t, 1 H); 4.19-4.31 (m, 1 H); 3.84-3.94 (m, 2 H); 3.45 (t, 2 H); 3.38 (s, 3 H); 1.15 (d, 3 H); 1.07 (t, 2 H). MS (ESI): [M + H]⁺ = 604. |
| 7 | 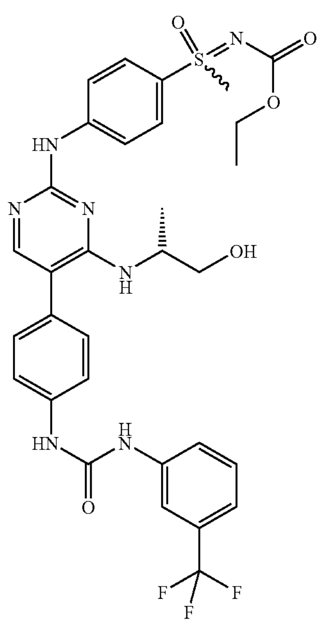 | 1-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[3-(trifluoromethyl)-phenyl]urea | ¹H-NMR (DMSO, 400 MHz): 9.74 (s, 1 H); 9.09 (s, 1 H); 8.93 (s, 1 H); 8.04 (d, 2 H); 8.00 (br. s, 1 H); 7.79 (s, 1 H); 7.77 (d, 2 H); 7.54-7.58 (m, 3 H); 7.49 (t, 1 H); 7.32 (d, 2 H); 7.28 (d, 1 H); 5.92 (d, 1 H); 4.81 (t, 1 H); 4.20-4.30 (m, 1 H); 3.85-3.93 (m, 2 H); 3.45 (t, 2 H); 3.38 (s, 3 H); 1.15 (d, 3 H); 1.07 (t, 3 H). MS (ESI): [M + H]⁺ = 672. |

-continued

| Example | Structure | Name | Analytical data |
|---|---|---|---|
| 8 | 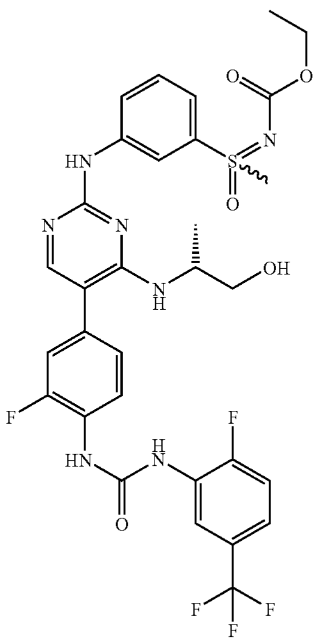 | 1-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]-2-fluorophenyl}-3-[2-fluoro-5-(trifluoromethyl)-phenyl]urea | $^1$H-NMR (DMSO, 400 MHz): 9.64 (s, 1 H); 9.35-9.41 (m, 1 H); 9.22-9.27 (m, 1 H); 8.60-8.71 (m, 2 H); 8.24 (t, 1 H); 7.91 (t br, 1 H); 7.81 (s, 1 H); 7.26-7.55 (m, 5 H); 7.18 (d, 1 H); 6.04 (d, 1 H); 4.73 (mc, 1 H); 4.32 (mc, 1 H); 3.80-3.94 (m, 2 H); 3.40-3.48 (m, 2 H); 3.35-3.40 (m, 3 H); 1.12 (d br, 3 H); 1.05 (t, 3 H). MS (ESI): [M + H]$^+$ = 707. |
| 9 | 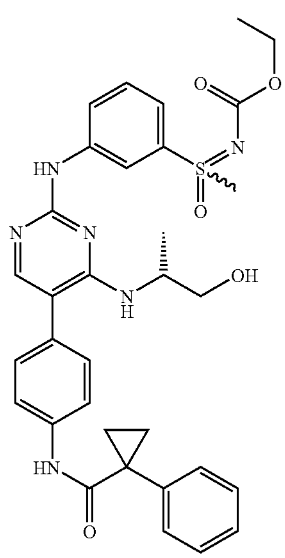 | N-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]phenyl}-1-phenylcyclopropane-carboxamide | $^1$H-NMR (DMSO, 400 MHz): 9.63 (s, 1 H); 9.21 (s, 1 H); 8.67 (s br, 1 H); 7.85-7.94 (m, 2 H); 7.74 (s, 1H), 7.62 (d, 2 H); 7.42-7.53 (m, 2 H); 7.22-7.41 (m, 6 H); 5.76-5.85 (m, 1 H); 4.68-4.75 (m, 1 H); 4.28 (mc, 1 H); 3.82-3.94 (m, 2 H); 3.32-3.49 (m, 5 H); 1.38-1.45 (m, 2 H); 1.11-1.17 (m, 5 H); 1.06 (t, 3 H). MS (ESI): [M + H]$^+$ = 629. |

| Example | Structure | Name | Analytical data |
|---|---|---|---|
| 10 | 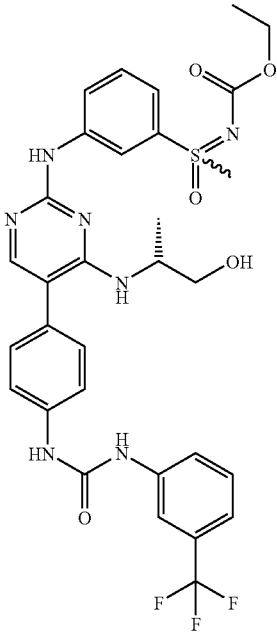 | 1-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[3-(trifluoromethyl)-phenyl]urea | $^1$H-NMR (DMSO, 400 MHz): 9.62 (s, 1 H); 9.07 (s, 1 H); 8.90 (s, 1 H); 8.66 (s br, 1 H); 8.00 (s br, 1 H); 7.85-7.94 (m, 1 H); 7.76 (s, 1 H); 7.24-7.61 (m, 9 H); 5.82-5.92 (m, 1 H); 4.70-478 (m, 1 H); 4.29 (mc, 1 H); 3.81-3.97 (m, 2 H); 3.32-3.48 (m, 5 H); 1.14 (d br, 3 H); 1.05 (t, 3 H). MS (ESI): [M + H]$^+$ = 672. |
| 11 | 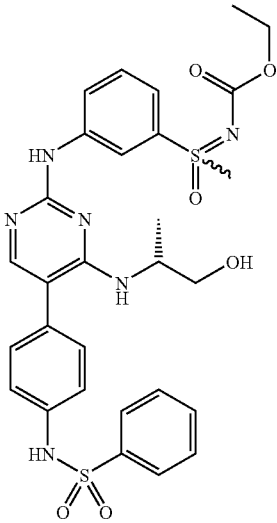 | N-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}benzene-sulfonamide | $^1$H-NMR (DMSO, 400 MHz): δ 10.46 (s, 1 H); 9.59 (s, 1 H); 8.63 (s br, 1 H); 7.84-7.93 (m, 1 H); 7.81 (d, 2 H); 7.71 (s, 1 H); 7.28-7.64 (m, 5 H); 7.26 (d, 2 H); 7.14 (d, 2 H); 5.77-5.85 (m, 1 H); 4.66-4.73 (m, 2 H); 4.26 (mc, 1 H); 3.80-3.95 (m, 2 H); 3.32-3.49 (m, 5 H); 1.02-1.11 (m, 6 H). MS (ESI): [M + H]$^+$ = 625. |

| Example | Structure | Name | Analytical data |
|---|---|---|---|
| 12 | 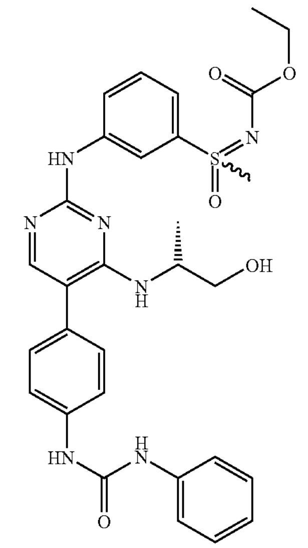 | 1-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[phenyl]urea | $^1$H-NMR (DMSO, 400 MHz): δ 9.60 (s, 1 H); 8.75 (s, 1 H); 8.67 (s, 2 H); 7.83-7.95 (m, 2 H); 7.76 (s, 1 H); 7.16-7.63 (m, 9 H); 6.93 (t, 1 H); 5.80-5.91 (m, 1 H); 4.70-481 (m, 1 H); 4.29 (mc, 1 H); 3.82-3.98 (m, 2 H); 3.32-3.51 (m, 5 H); 1.14 (d br, 3 H); 1.06 (t, 3 H). MS (ESI): [M + H]$^+$ = 603. |
| 13 | 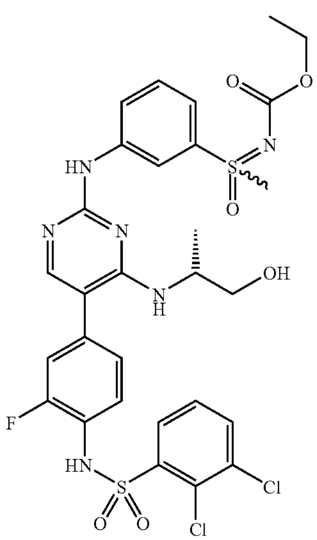 | 2,3-Dichloro-N-{4-[2-({3-[(RS)-N-(ethoxycarbonyl)-S-methylsulfonimidoyl]phenyl}amino)-4-{[(R)-2-hydroxy-1-methylethyl]amino}-pyrimidin-5-yl]-2-fluorophenyl}-benzenesulfonamide | $^1$H-NMR (DMSO, 400 MHz): δ 10.69 (s br, 1 H); 9.65 (s, 1 H); 8.57-8.66 (m, 1 H); 7.82-7.97 (m, 3 H); 7.78 (s, 1 H); 7.12-7.55 (m, 6 H); 6.03 (d, 1 H); 4.64-4.72 (m, 1 H); 4.29 (mc, 1 H); 3.80-3.96 (m, 2 H); 3.32-3.47 (m, 5 H); 1.00-1.12 (m, 6 H). MS (ESI): [M + H]$^+$ = 711 ($^{35}$Cl). |

| Example | Structure | Name | Analytical data |
|---|---|---|---|
| 14 | 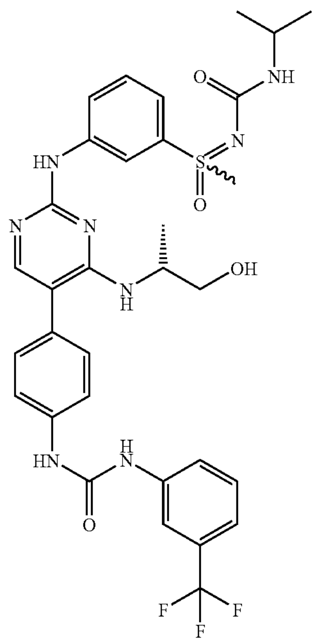 | 1-{4-[4-{[(R)-2-hydroxy-1-methylethyl]amino}-2-({3-[(RS)-N-(isopropylcarbamoyl)-S-methylsulfonimidoyl]phenyl}amino)-pyrimidin-5-yl]phenyl}-3-[3-(trifluoromethyl)-phenyl]urea | $^1$H-NMR (DMSO, 300 MHz): 10.42 (s br, 1 H); (s, 1 H); 9.22 (s, 1 H); 8.49 (d, 1 H); 8.05 (s, 1 H); 7.81 (s, 2 H); 7.63 (m, 5 H); 7.53 (t, 1 H); 7.37 (d, 2 H); 7.32 (d, 1 H); 6.86 (m, 1 H); 4.39 (m, 1 H); 3.59 (m, 1 H); 3.47 (m, 2 H); 3.37 (d, 3 H); 1.15 (d, 3 H); 1.00 (m, 6 H) |
| 15 | 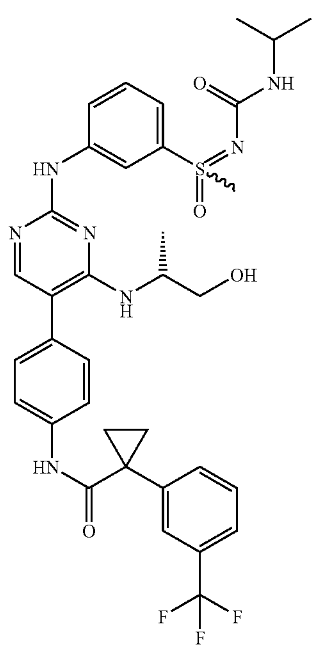 | N-{4-[4-{[(R)-2-hydroxy-1-methylethyl]amino}-2-({3-[(RS)-N-(isopropylcarbamoyl)-S-methylsulfonimidoyl]phenyl}amino)-pyrimidin-5-yl]phenyl}-1-[3-(trifluoromethyl)-phenyl]cyclopropane carboxamide | $^1$H-NMR (DMSO, 300 MHz): 9.59 (s, 1 H); 9.47 (s, 1 H); 8.67 (s, 1 H); 7.87 (d, 1 H); 7.78 (s, 1 H); 7.65 (m, 6 H); 7.49 (t, 1 H); 7.39 (d, 1 H); 7.32 (d, 2 H); 6.79 (m, 1 H); 5.85 (m, 1 H); 4.78 (m, 1 H); 4.32 (m, 1 H); 3.59 (m, 1 H); 3.45 (m, 2 H); 3.33 (d, 3 H); 1.52 (m, 2 H); 1.23 (m, 2 H); 1.14 (d, 3 H); 1.00 (m, 6 H) |

| Example | Structure | Name | Analytical data |
|---|---|---|---|
| 16 | 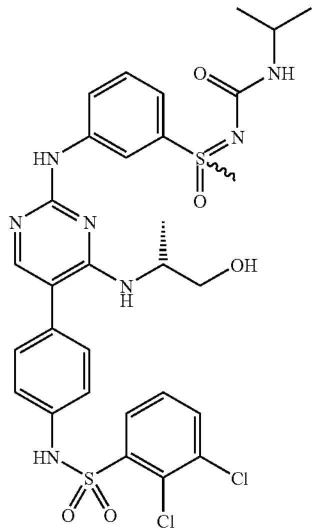 | 2,3-dichloro-N-{4-[4-{[(1R)-2-hydroxy-1-methylethyl]amino}-2-({3-[(RS)-N-(isopropylcarbamoyl)-S-methylsulfonimidoyl]phenyl}amino)-pyrimidin-5-yl]phenyl}benzene-sulfonamide | $^1$H-NMR (DMSO, 300 MHz): 10.99 (s, 1 H); 9.58 (s, 1 H); 8.63 (s, 1 H); 8.13 (d, 1 H); 7.96 (d, 1 H); 7.86 (m, 1 H); 7.72 (s, 1 H); 7.60 (t, 1 H); 7.48 (t, 1 H); 7.39 (d, 1 H); 7.30 (d, 2 H); 7.18 (d, 2 H); 6.78 (m, 1 H); 5.90 (m, 1 H); 4.74 (m, 1 H); 4.32 (m, 1 H); 3.59 (m, 1 H); 3.43 (m, 2 H); 3.32 (d, 3 H); 1.12 (d, 3 H); 0.99 (m, 6 H) |

Example Compound 17

Preparation of 1-{4-[2-({3-[(RS)-N-(Ethoxycarbonyl)-S-methylsulfonimidoyl]phenyl}amino)-4-(methylsulfanyl)pyrimidin-5-yl]-2-fluorophenyl}-3-[2-fluoro-5-(trifluoromethyl)phenyl]urea Example Compound 17 was prepared in analogy to GP 7 by reaction of 4.9 g of Intermediate 13 (11 mmol) with 5.3 g of Intermediate 19 (12 mmol; 1.09 eq.) in the presence of 1 g tris-(2-furyl)-phosphine (4 mmol; 0.36 eq.), 17 mL aq. Na$_2$CO$_3$ solution (1M, 1.55 eq.) and 500 mg Pd(PPh$_3$)$_4$ (0.5 mmol; 4.5 mol %) in 100 mL dry DME yielding 4.5 g of the target compound (60% yield).

$^1$H-NMR (DMSO, 300 MHz): 9.40 (br. s, 1H); 8.63-8.73 (m, 2H); 8.30 (t, 1H); 8.20 (s, 1H); 7.95 (d, 1H); 7.58 (t, 1H); 7.38-7.52 (m, 4H); 7.28 (d, 1H); 3.83-3.95 (m, 2H); 3.40 (s, 3H); 2.60 (s, 3H); 1.08 (t, 3H).

MS (ESI): [M+H]$^+$=681.

Example Compound 18

Preparation of 2,3-Dichloro-N-{4-[2-({3-[(RS)-N-(ethoxycarbonyl)-S-methylsulfonimidoyl]phenyl}amino)-4-(methoxy)-pyrimidin-5-yl]-2-fluorophenyl}-benzenesulfonamide Example compound 18 was prepared by reacting Intermediate 15 (275 mg, 0.60 mmol) with 2,3-dichlorobenzene sulfonyl chloride (206 mg, 0.84 mmol, 1.4 eq) in neat pyridine (3.7 mL) at room temperature for 5 h. All volatiles were removed in vacuo and the crude residue was purified by prep. HPLC to give 191 mg (48% yield) of the pure target compound.

$^1$H-NMR (DMSO, 300 MHz): 10.62 (s, 1H); 10.19 (s, 1H); 8.74 (s br, 1H); 8.37 (s, 1H); 7.79-7.97 (m, 3H); 7.30-7.60 (m, 5H); 7.24 (t, 1H); 3.98 (s, 3H); 3.88 (mc, 2H); 3.38 (s, 3H); 1.05 (t, 3H).

MS (ESI): [M+H]$^+$=668 ($^{35}$Cl).

Example Compound 19

Preparation of N-{4-[4-{[(R)-2-Hydroxy-1-methyl-ethyl]amino}-2-({3-[(RS)-S-methylsulfonimidoyl]-phenyl}amino)pyrimidin-5-yl]-2-fluorophenyl}-3-[2-fluoro-5-(trifluoromethyl)phenyl]urea

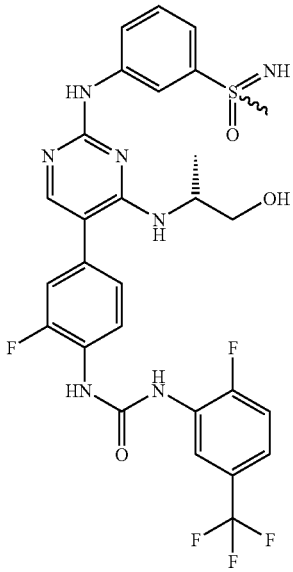

Example Compound 19 was prepared in analogy to GP 6 by reaction of 138 mg of Intermediate 9 (0.31 mmol) with 194 mg of Intermediate 19 (0.44 mmol; 1.42 eq.) in the presence of 21 mg Pd(PPh$_3$)$_4$ (6 mol %) and 0.60 mL aq. Na$_2$CO$_3$ solution (1M, 1.93 eq.) in a mixture of toluene and ethanol (2.53 mL each) yielding 45 mg of the target compound (23% yield).

$^1$H-NMR (DMSO, 400 MHz): 9.53 (s br, 1H); 9.39 (s br, 1H); 9.24 (s br, 1H); 8.70 (d, 1H); 8.58-8.66 (m, 1H); 8.23 (t, 1H); 7.71-7.83 (m, 2H); 7.34-7.55 (m, 4H); 7.31 (d, 1H); 7.18 (d, 1H); 6.03 (t br, 1H); 4.76-4.88 (m, 1H); 4.37 (mc, 1H); 4.10-4.16 (m, 1H); 3.32-3.55 (m, 2H); 3.00 (s, 3H); 1.14 (d, 3H).

MS (ESI):[M+H]$^+$=636.

The following example compounds were prepared according to general procedure GP 6 from Intermediates 11 or 14a, and the respective phenyl boronic acid pinacolate ester:

| Example | Structure | Name | Analytical data |
|---|---|---|---|
| 20 | 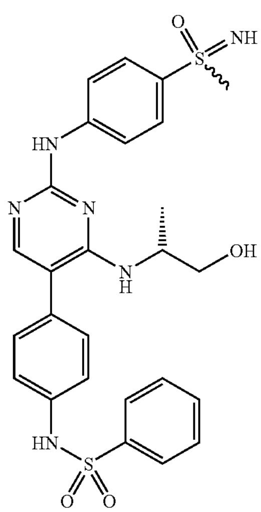 | N-[4-(4-{[(R)-2-hydroxy-1-methylethyl]amino}-2-{[4-(RS)-(S-methylsulfonimidoyl)phenyl]amino}-pyrimidin-5-yl)phenyl]benzenesulfonamide | $^1$H-NMR (DMSO, 400 MHz): 10.48 (s br, 1 H); 9.58 (s, 1 H); 7.94 (d, 2 H); 7.80 (d, 2 H); 7.73 (d, 2 H); 7.70 (s, 1 H); 7.52-7.62 (m, 3 H); 7.25 (d, 2 H); 7.14 (d, 2 H); 5.84 (d, 1 H); 4.75 (t, 1 H); 4.31 (mc, 1 H); 3.91 (s, 1 H); 3.37-3.46 (m, 2 H); 2.97 (s, 3 H); 1.10 (d, 3 H). MS (ESI): [M + H]$^+$ = 553. |

-continued

| Example | Structure | Name | Analytical data |
|---|---|---|---|
| 21 | 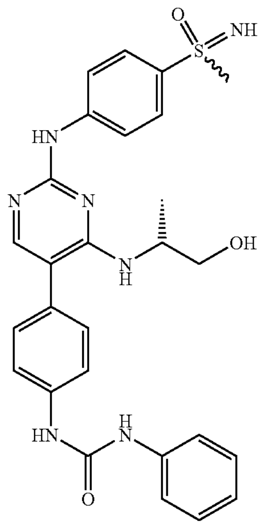 | 1-[4-(4-{[(R)-2-hydroxy-1-methylethyl]amino}-2-{[4-(RS)-(S-methylsulfonimidoyl)phenyl]amino}-pyrimidin-5-yl)phenyl]-3-phenylurea | ¹H-NMR (DMSO, 300 MHz): 9.74 (s, 1 H); 8.83 (s, 1 H); 8.74 (s, 1 H); 8.04 (d, 2 H); 7.84 (d, 2 H); 7.83 (s, 1 H; 7.58 (d, 2 H); 7.48 (d, 2 H); 7.35 (d, 2 H); 7.30 (t, 2 H); 6.99 (tt, 1 H); 6.04 (d, 1 H); 4.84 (s br, 1 H); 4.30 (mc, 1 H); 3.46-3.50 (m, 2 H); 3.18 (s, 3 H); 1.19 (d, 3 H). MS (ESI): [M + H]⁺ = 532. |
| 22 | 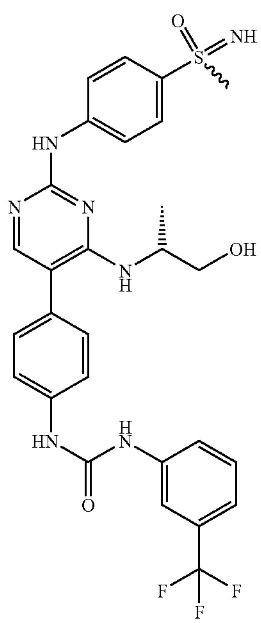 | 1-[4-(4-{[(R)-2-hydroxy-1-methylethyl]amino}-2-{[4-(RS)-(S-methylsulfonimidoyl)phenyl]amino}-pyrimidin-5-yl)phenyl]-3-[3-(trifluoromethyl)-phenyl]urea | ¹H-NMR (DMSO, 300 MHz): 9.59 (s, 1 H); 9.14 (s, 1 H); 8.97 (s, 1 H); 7.99 (s, 1 H); 7.97 (d, 2 H); 7.78 (s, 1 H); 7.74 (d, 2 H); 7.56 (d, 1 H); 7.55 (d, 2 H); 7.48 (t, 1 H); 7.31 (d, 2 H); 7.28 (d, 1 H); 5.88 (d, 1 H); 4.80 (t, 1 H); 4.25 (mc, 1 H); 3.92 (s, 1 H); 3.45 (t, 2 H); 2.98 (s, 3 H); 1.14 (d, 3 H). MS (ESI): [M + H]⁺ = 600. |

| Example | Structure | Name | Analytical data |
|---|---|---|---|
| 23 | 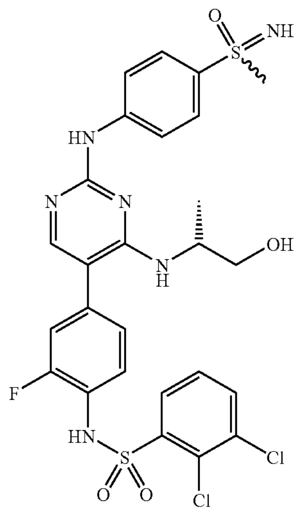 | 2,3-dichloro-N-[2-fluoro-4-(4-{[(R)-2-hydroxy-1-methylethyl]amino}-2-{[4-(RS)-(S-methylsulfonimidoyl)phenyl]amino}-pyrimidin-5-yl)phenyl]benzene-sulfonamide | $^1$H-NMR (DMSO, 300 MHz): 9.67 (s, 1 H); 7.96-8.00 (m, 4 7.77-7.82 (m, 3 H); 7.56 (t, 1 H); 7.26-7.32 (m, 2 H); 7.19 (dd, 1 H); 6.11 (d, 1 H); 4.78 (t, 1 H); 4.29 (mc, 1 H); 3.41-3.52 (m, 2 H); 3.03 (s, 3 H); 1.16 (d, 3 H). MS (ESI): [M]$^+$ = 639/641/643 (Cl$_2$ isotope pattern). |
| 24 | 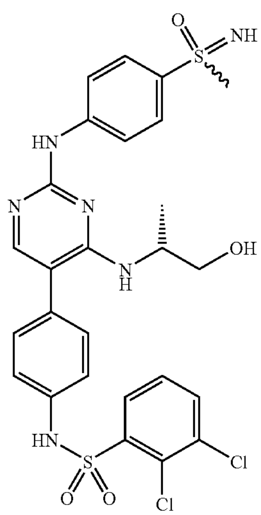 | 2,3-dichloro-N-[4-(4-{[(R)-2-hydroxy-1-methylethyl]amino}-2-{[4-(RS)-(S-methylsulfonimidoyl)phenyl]amino}-pyrimidin-5-phenyl]benzene-sulfonamide | $^1$H-NMR (DMSO, 300 MHz): 11.03 (s, 1 H); 9.81 (s, 1 H); 8.15 (dd, 1 H); 8.03 (d, 2 H); 7.98 (dd, 1 H); 7.85 (d, 2 H); 7.76 (s, 1 H); 7.61 (t, 1 H); 7.32 (d, 2 H); 7.19 (d, 2 H); 6.10 (d, 1 H), 4.79 (s br, 1 H), 4.27 (mc, 1 H); 3.43-3.51 (m, 2 H); 3.26 (s, 3 H); 1.15 (d, 2 H). MS (ESI): [M]$^+$ = 621/623/625 (Cl$_2$ isotope pattern). |
| 25 | 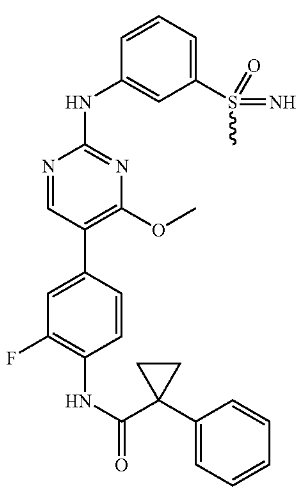 | N-[2-fluoro-4-(4-methoxy-2-{[3-(RS)-thylsulfonimidoyl)-phenyl]amino}-pyrimidin-5-yl)phenyl]-1-phenylcyclopropane-carboxamide | $^1$HNMR (DMSO, 300 MHz): 10.10 (s, 1 H); 8.74 (s br, 1 H); 8.41 (s, 1 H); 8.25 (s br, 1 H); 7.76-7.89 (m, 2 H); 7.32-7.57 (m, 9 H); 4.12 (s, 1 H); 4.03 (s, 3 H); 3.05 (s, 3 H); 1.52 (mc, 2 H); 1.18 (mc, 2 H). MS (ESI): [M + H]$^+$ = 532. |

Example Compound 26

Preparation of 1-{4-[2-({3-[(RS)-N-(ethoxycarbonyl)-S-methylsulfonimidoyl]phenyl}amino)-4-{[2-(pyrrolidin-1-yl)ethyl]amino}pyrimidin-5-yl]-2-fluorophenyl}-3-[2-fluoro-5-(trifluoromethyl)phenyl]urea

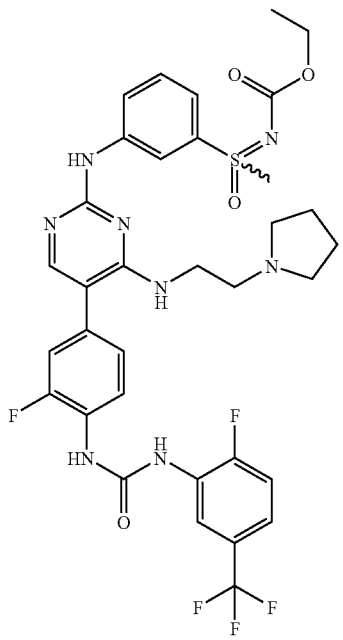

Example Compound 26 was prepared in analogy to GP 8 by reaction of 238 mg of Example Compound 17 (0.35 mmol) with 118 mg of meta-chloroperbenzoic acid (0.52 mmol; 1.5 eq.) in N-methylpyrrolidinone (3.4 mL), followed by treatment with 0.089 mL 1-pyrrolidineethaneamine (0.70 mmol, 2.0 eq.) and 0.12 mL triethylamine (0.88 mmol, 2.5 eq.) yielding 64 mg of the target compound (24% yield).

$^1$H-NMR (DMSO, 400 MHz): 9.66 (s, 1H); 9.38 (d, 1H); 9.23 (s br, 1H); 8.58-8.70 (m, 2H); 8.22 (t, 1H); 7.97 (d br, 1H); 7.80 (s, 1H); 7.25-7.56 (m, 5H); 7.16 (d, 1H); 6.46 (t br, 1H); 3.81-3.96 (m, 2H); 3.45-3.58 (m, 2H); 3.35 (s, 3H); 2.35-2.69 (m, 6H; partly covered by DMSO peak), 1.58-1.73 (m, 4H); 1.06 (t, 3H).

MS (ESI):[M+H]$^+$=747.

The following example compounds were prepared by in situ oxidation of the thiomethyl group in example compound 17, followed by nucleophilic displacement by the respective nucleophile according to GP 8.

| Example | Structure | Name | Analytical data |
|---|---|---|---|
| 27 | 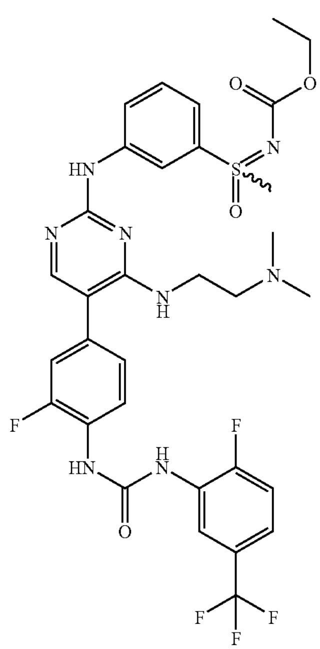 | 1-{4-[4-{[2-N,N-(Dimethylamino)ethyl]amino}2-({3-[(RS)-N-(ethoxycarbonyl)-S-methylsulfonimidoyl]phenyl}amino)pyrimidin-5-yl]-2-fluorophenyl}-3-[2-fluoro-5-(trifluoromethyl)-phenyl]urea | $^1$H-NMR (DMSO, 300 MHz): 9.68 (s, 1 H); 9.42 (s br, 1 H); 9.28 (s br, 1 H); 8.63-8.71 (m, 2 H); 8.29 (t, 1 H); 7.99-8.08 (m, 1 H); 7.85 (s, 1 H); 7.48-7.59 (m, 2 H); 7.39-7.46 (m, 2 H); 7.34 (dd, 1 H); 7.22 (d br, 1 H); 6.49 (t br, 1 H); 3.85-4.01 (m, 2 H); 3.50-3.61 (m, 2 H); 3.43 (s, 3 H); 2.45-2.58 (m, 2 H); 2.18 (s, 6 H); 1.12 (t, 3 H). MS (ESI): [M + H]$^+$ = 721. |

-continued

| Example | Structure | Name | Analytical data |
|---|---|---|---|
| 28 | 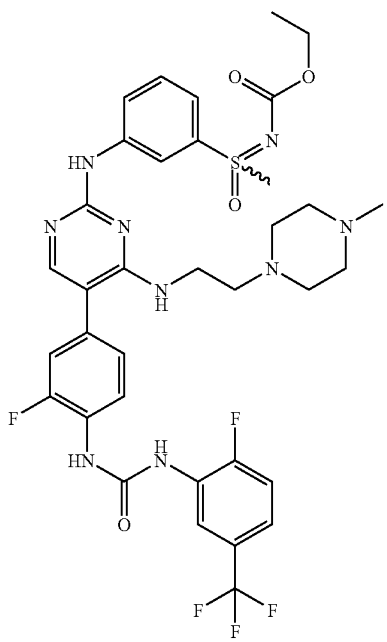 | 1-{4-[2-({3-[(RS)-N-(Ethoxycarbonyl)-S-methylsulfonimidoyl]phenyl}amino)-4-{[2-(N-methyl-piperazin-4-yl)ethyl]amino}pyrimidin-5-yl]-2-fluorophenyl}-3-[2-fluoro-5-(trifluoromethyl)-phenyl]urea | $^1$H-NMR (DMSO, 400 MHz): 9.67 (s, 1 H); 9.38 (d, 1 H); 9.24 (s br, 1 H); 8.71 (s br, 1 H); 8.63 (d br, 1 H); 8.27 (t, 1 H); 7.92 (d br, 1 H); 7.83 (s, 1 H); 7.44-7.52 (m, 2 H); 7.30-7.41 (m, 3 H); 7.18 (d br, 1 H); 6.48 (t br, 1 H); 3.83-3.94 (m, 2 H); 3.45-3.52 (m, 2 H); 3.38 (s, 3 H); 2.05-2.64 (m, 10 H); 2.12 (s, 3 H); 1.07 (t, 3 H). MS (ESI): [M + H]$^+$ = 776. |
| 29 | 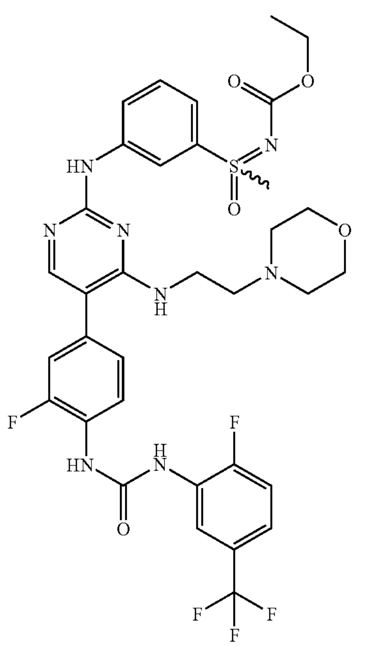 | 1-{4-[2-({3-[(RS)-N-(Ethoxycarbonyl)-S-methylsulfonimidoyl]phenyl}amino)-4-{[2-(morpholin-4-yl)ethyl]amino}pyrimidin-5-yl]-2-fluorophenyl}-3-[2-fluoro-5-(trifluoromethyl)-phenyl]urea | $^1$H-NMR (DMSO, 400 MHz): 9.66 (s, 1 H); 9.36 (d, 1 H); 9.25 (s br, 1 H); 8.68 (s br, 1 H); 8.63 (dd, 1 H); 8.25 (t, 1 H); 7.92 (d br, 1 H); 7.83 (s, 1 H); 7.42-7.53 (m, 2 H); 7.30-7.40 (m, 3 H); 7.20 (d br, 1 H); 6.51 (t br, 1 H); 3.82-3.96 (m, 2 H); 3.48-3.60 (m, 6 H); 3.37 (s, 3 H); 2.28-2.55 (m, 6 H, partly covered by DMSO signal); 1.07 (t, 3 H). MS (ESI): [M + H]$^+$ = 763. |

US 8,003,655 B2

-continued

| Example | Structure | Name | Analytical data |
|---|---|---|---|
| 30 | 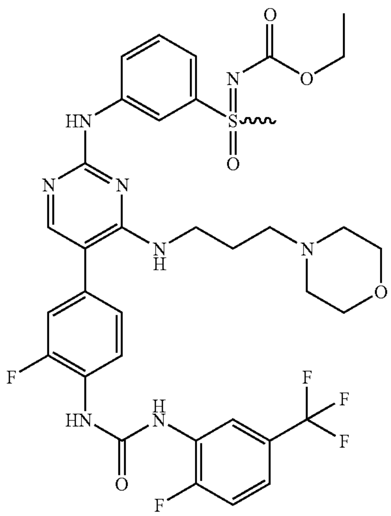 | 1-{4-[2-({3-[(RS)-N-(Ethoxycarbonyl)-S-methylsulfonimidoyl]phenyl}amino)-4-{[3-(morpholin-4-yl)propyl]amino}pyrimidin-5-yl]-2-fluorophenyl}-3-[2-fluoro-5-(trifluoromethyl)-phenyl]urea | $^1$H-NMR (CDCl$_3$, 300 MHz): 8.86 (s, 1 H); 8.59 (dd, 1 H); 8.18 (t, 1 H); 7.87-8.01 (m, 2 H); 7.63 (s, 1 H); 7.34-7.52 (m, 3 H); 7.18-7.31 (m, 2 H); 7.13 (mc, 1 H); 6.90-7.03 (m, 2 H); 6.03 (t br, 1 H); 4.14 (mc, 2 H); 3.54-3.67 (m, 2 H); 3.42-3.54 (m, 4 H); 3.28 (s, 3 H); 2.30-2.53 (m, 6 H); 1.80 (m, 2 H; covered by water peak), 1.24 (t, 3 H). MS (ESI): [M + H]$^+$ = 777. |

Example Compound 31

Preparation of 1-{4-[2-({3-[(RS)-N-(Ethoxycarbonyl)-S-methylsulfonimidoyl]phenyl}amino)-4-(methoxy)-pyrimidin-5-yl]-2-fluorophenyl}-3-[2-fluoro-5-(trifluoromethyl)-phenyl]urea

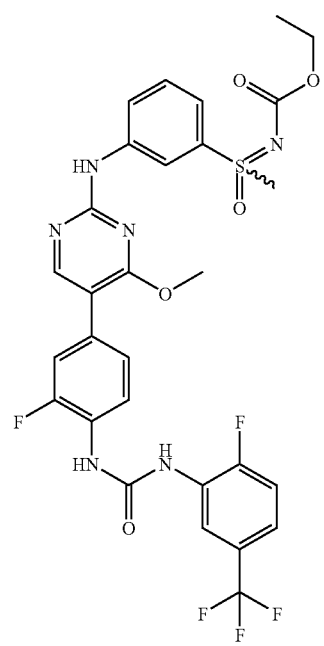

A solution of Example compound 17 (170 mg, 0.25 mmol) in NMP (2.4 mL) was treated with mCPBA (1.5 eq) and then stirred for 2 h at room temperature. The mixture was then diluted with water and extracted with ethyl acetate, dried and evaporated. The residue was roughly purified over a short plug of silica to isolate a mixture of the sulfoxide and sulfone corresponding to Example compound 17. Said mixture was dissolved in dry DMF (0.5 mL) and then added to a solution of sodium methoxide in DMF (5 mL) freshly prepared from sodium hydride (22 mg, 0.5 mmol) and methanol (20 µL, 0.5 mmol). The mixture was then stirred at room temperature overnight and subsequently evaporated. Purification of the crude residue by column chromatography, followed by prep HPLC gave 19 mg (11% yield) of the desired target compound.

$^1$H-NMR (DMSO, 400 MHz): 10.18 (s, 1H); 9.36 (s br, 1H); 9.20 (s br, 1H); 8.76 (s, 1H); 8.62 (dd, 1H); 8.41 (s, 1H); 8.18 (t, 1H); 7.86 (d br, 1H); 7.43-7.61 (m, 4H); 7.33-7.41 (m, 2H); 4.03 (s, 3H); 3.89 (mc, 2H); 3.39 (s, 3H); 1.07 (t, 3H).

MS (ESI):[M+H]$^+$=665.

Example Compound 32

Preparation of N-{4-[4-{[(R)-2-Hydroxy-1-methyl-ethyl]amino}-2-({4-[(RS)-S-methylsulfonimidoyl]phenyl}amino)pyrimidin-5-yl]phenyl}-1-phenylcyclopropanecarboxamide

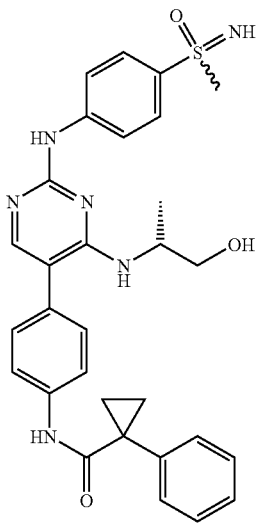

Example Compound 32 was prepared in analogy to GP 9 by reaction of 110 mg of Example Compound 1 (0.17 mmol, 1 eq.) with 0.23 mL NaOEt solution (20% in EtOH; 0.63 mmol; 3.6 eq.) in 1.4 mL EtOH yielding 49 mg (0.088 mmol; 50% yield) of the target compound of ~90% purity which was further purified by preparative HPLC purification.

$^1$H-NMR (DMSO, 400 MHz): 9.59 (s, 1H); 9.23 (s, 1H); 7.95 (d, 2H); 7.75 (s, 1H); 7.74 (d, 2H); 7.63 (d, 2H); 7.23-7.38 (m, 7H); 5.84 (d, 1H); 4.78 (t, 1H); 4.18-4.26 (m, 1H); 3.92 (s, 1H); 3.42 (t, 2H); 2.98 (s, 3H); 1.40-1.44 (m, 2H); 1.09-1.13 (m, 5H).

MS (ESI): [M+H]$^+$=557.

Example Compound 33

Preparation of N-{4-[4-{[(R)-2-Hydroxy-1-methyl-ethyl]amino}-2-({3-[(RS)-S-methylsulfonimidoyl]phenyl}amino)pyrimidin-5-yl]phenyl}-1-phenylcyclopropanecarboxamide

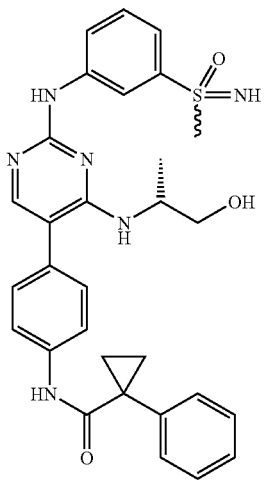

Example Compound 33 was prepared in analogy to GP 9 by reaction of 108 mg of Example Compound 9 (0.17 mmol, 1 eq.) with 0.19 mL NaOEt solution (20% in EtOH; 0.52 mmol; 3.0 eq.) in 2.8 mL EtOH yielding 52 mg (0.093 mmol; 54% yield) of the target compound.

$^1$H-NMR (DMSO, 400 MHz): 9.50 (s br, 1H); 9.21 (s, 1H); 8.64-8.72 (m, 1H); 7.70-7.81 (m, 2H); 7.62 (d, 2H); 7.20-7.45 (m, 9H); 5.78 (mc, 1H); 4.75-4.88 (m, 1H); 4.25-4.39 (m, 1H); 4.10 (s br, 1H); 3.33-3.48 (m, 2H); 2.99 (s, 3H); 1.38-1.46 (m, 2H); 1.05-1.15 (m, 5H).

MS (ESI): [M+H]$^+$=557.

The following example compounds were prepared according to general procedure GP 9 from the respective N-ethoxycarbonyl-substituted sulfoximine by sodium ethoxide mediated alcoholysis.

| Example | Structure | Name | Analytical data |
|---|---|---|---|
| 34 | 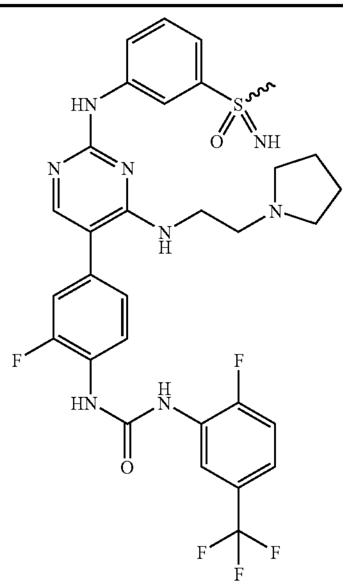 | 1-{4-[2-({3-[(RS)-S-Methylsulfonimidoyl]phenyl}amino)-4-{[2-(pyrrolidin-1-yl)ethyl]amino}pyrimidin-5-yl]-2-fluorophenyl}-3-[2-fluoro-5-(trifluoromethyl)phenyl]urea | $^1$H-NMR (DMSO, 300 MHz): 9.52 (s, 1 H); 9.36 (d, 1 H); 9.22 (s br, 1 H); 8.56-8.66 (m, 2 H); 8.22 (t, 1 H); 7.82-7.92 (m, 1 H); 7.79 (s, 1 H); 7.24-7.53 (m, 5 H); 7.18 (d br, 1 H); t br, 6.53 (t br, 1 H); 4.17 (s br, 1 H); 3.52 (mc, 2 H); 2.99 (s, 3 H); 2.33-2.72 (m, 6 H; covered partly by DMSO peak), 1.57-1.72 (m, 4 H). MS (ESI): [M + H]$^+$ = 675. |

| Example | Name | Analytical data |
|---------|------|-----------------|
| 35 | 1-[4-(4-{[2-(Dimethylamino)ethyl]amino}-2-{[3-(RS)-(S-methylsulfonimidoyl)phenyl]amino}-pyrimidin-5-yl)-2-fluorophenyl]-3-[2-fluoro-5-(trifluoromethyl)-phenyl]urea | $^1$H-NMR (DMSO, 400 MHz): 9.51 (s, 1 H); 9.37 (s br, 1 H); 9.23 (s br, 1 H); 8.63 (dd, 1 H); 8.57 (s, 1 H); 8.23 (t, 1 H); 7.86-7.92 (m, 1 H); 7.79 (s, 1 H); 7.33-7.53 (m, 4 H); 7.30 (dd, 1 H); 7.18 (d, 1 H); 6.44 (t, 1 H); 4.11 (s br, 1 H); 3.50 (mc, 2 H); 2.98 (s, 3 H); 2.33-2.50 (m, 2 H; partly covered by DMSO peak); 2.11 (s, 6 H). MS (ESI): [M + H]$^+$ = 649. |
| 36 | 1-[2-Fluoro-4-(4-{[2-(4-methylpiperazin-1-yl)ethyl]amino}-2-{[3-(RS)-(S-methylsulfonimidoyl)phenyl]amino}-pyrimidin-5-yl)phenyl]-3-[2-fluoro-5-(trifluoromethyl)-phenyl]urea | $^1$H-NMR (DMSO, 300 MHz): 9.52 (s, 1 H); 9.36 (s br, 1 H); 9.24 (s br, 1 H); 8.58-8.67 (m, 2 H); 8.26 (t, 1 H); 7.78-7.90 (m, 2 H); 7.28-7.55 (m, 5 H); 7.15 (d, 1 H); 6.46 (t br, 1 H); 4.08 (s, 1 H); 3.42-3.57 (m, 2 H); 2.99 (s, 3 H); 2.05-2.58 (m, 10 H, partly covered by DMSO peak); 2.11 (s, 3 H). MS (ESI): [M + H]$^+$ = 704. |
| 37 | 1-[2-Fluoro-4-(2-{[3-(RS)-(S-methylsulfonimidoyl)phenyl]amino}-4-[(2-morpholin-4-ylethyl)amino]-pyrimidin-5-yl)phenyl]-3-[2-fluoro-5-(trifluoromethyl)-phenyl]urea | $^1$H-NMR (DMSO, 400 MHz): 9.53 (s, 1 H); 9.36 (s br, 1 H); 9.25 (S br, 1 H); 8.59-8.64 (m, 2 H); 8.24 (t, 1 H); 7.72-7.78 (m, 1 H); 7.71 (s, 1 H); 7.33-7.52 (m, 5 H); 7.18 (d, 1 H); 6.50 (t, 1 H); 4.10 (s, 1 H); 3.45-3.58 (s, 6 H); 3.00 (s, 3 H); 2.45-2.54 (m, 2 H); partly covered by DMSO peak); 2.37 (s br, 4 H). MS (ESI): [M + H]$^+$ = 691. |

| Example | Name | Analytical data |
|---|---|---|
| 38 | 2,3-Dichloro-N-[4-(4-{[(R)-2-hydroxy-1-methylethyl]amino}-2-{[3-(RS)-(S-methylsulfonimidoyl)phenyl]amino}-pyrimidin-5-yl)phenyl]benzene-sulfonamide | $^1$H-NMR (DMSO, 300 MHz): 10.98 (s, 1 H); 9.68 (s, 1 H); 8.63 (d, 1 H); 8.10 (dd, 1 H); 7.93 (dd, 1 H); 7.70-7.79 (m, 1 H); 7.68 (s, 1 H); 7.56 (t, 1 H); 7.43 (mc, 2 H); 7.28 (d, 2 H); 7.14 (d, 2 H); 6.13 (s br, 1 H); 4.32 (mc, 1 H); 3.28-3.53 (m, 3 H; overlap with water peak); 3.02 (s, 3 H); 1.08 (d, 3 H). MS (ESI): [M + H]$^+$ = 621 ($^{35}$Cl). |
| 39 | 1-[4-(4-{[(R)-2-Hydroxy-1-methylethyl]amino}-2-{[3-(RS)-(S-methylsulfonimidoyl)phenyl]amino}-pyrimidin-5-yl)phenyl]-3-[3-(trifluoromethyl)-phenyl]urea | $^1$H-NMR (DMSO, 300 MHz): 9.54 (s, 1 H); 9.12 (s, 1 H); 8.92 (s, 1 H); 8.68 (d, 1 H); 8.00 (s, 1 H); 7.74-7.82 (m, 2 H); 7.38-7.60 (m, 6 H); 7.22-7.34 (m, 3 H); 5.92 (mc, 1 H); 4.82 (s br, 1 H); 4.35 (mc, 1 H); 3.35-3.52 (m, 3 H); 3.02 (s, 3 H); 1.14 (d, 3 H). MS (ESI): [M + H]$^+$ = 600. |
| 40 | N-[4-(4-{[(R)-2-Hydroxy-1-methylethyl]amino}-2-{[3-(RS)-(S-methylsulfonimidoyl)phenyl]amino}-pyrimidin-5-yl)phenyl]benzene-sulfonamide | $^1$H-NMR (DMSO, 300 MHz): 10.47 (s, 1 H); 9.55 (s, 1 H); 8.67 (d, 1 H); 7.71-7.85 (m, 3 H); 7.68 (s, 1 H); 7.50-7.65 (m, 3 H); 7.36-7.47 (m, 2 H); 7.25 (d, 2 H); 7.14 (d, 2 H); 5.89 (mc, 1 H); 4.80 (s br, 1 H); 4.33 (mc, 1 H); 3.31-3.48 (m, 3 H; overlap with water peak); 3.01 (s, 3 H); 1.08 (d, 3 H). MS (ESI): [M + H]$^+$ = 553. |

| Example | Structure | Name | Analytical data |
|---|---|---|---|
| 41 | 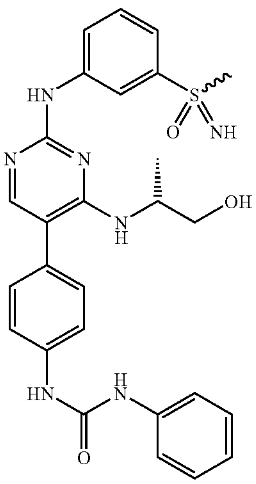 | 1-[4-(4-{[(R)-2-Hydroxy-1-methylethyl]amino}-2-{[3-(RS)-(S-methylsulfonimidoyl)phenyl]amino}-pyrimidin-5-yl)phenyl]-3-phenylurea | $^1$H-NMR (DMSO, 300 MHz): 9.95 (s, 1 H); 8.92 (s, 1 H); 8.80 (s, 1 H); 8.58-8.68 (m, 1 H); 7.72-7.81 (m, 2 H); 4.49-7.62 (m, 4 H); 7.44 (d, 2 H); 7.20-7.36 (m, 4 H); 6.94 (t, 1 H); 6.54 (s br, 1 H); 4.37 (mc, 1 H); 3.35-3.52 (m, 3 H); overlap with water peak); 3.11 (s, 3 H); 1.12 (d, 3 H). (sulfoximine = NH not detected) MS (ESI): [M + H]$^+$ = 532. |
| 42 | 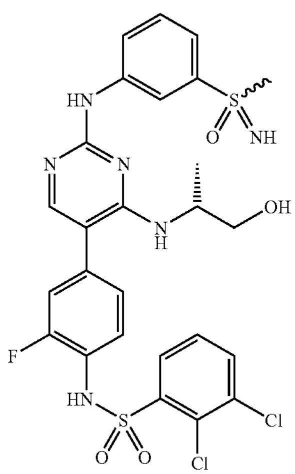 | 2,3-Dichloro-N-[2-fluoro-4-(4-{[(R)-2-hydroxy-1-methylethyl]amino}-2-{[3-(RS)-(S-methylsulfonimidoyl)phenyl]amino}-pyrimidin-5-yl)phenyl]benzenesulfonamide | $^1$H-NMR (DMSO, 300 MHz): 10.70 (s br, 1 H); 9.61 (s, 1 H); 8.66 (d br, 1 H); 7.93 (mc, 2 H); 7.69-7.81 (m, 2 H); 7.54 (t, 1 H); 7.36-7.47 (m, 2 H); 7.20-7.30 (m, 2 H); 7.15 (d, 1 H); 6.13 (t br, 1 H); 4.82 (s br, 1 H); 4.34 (mc, 1 H); 3.26-3.49 (m, 3 H; overlap with water peak); 3.02 (s, 3 H); 1.08 (d, 3 H). MS (ESI): [M + H]$^+$ = 639 ($^{35}$Cl). |
| 43 | 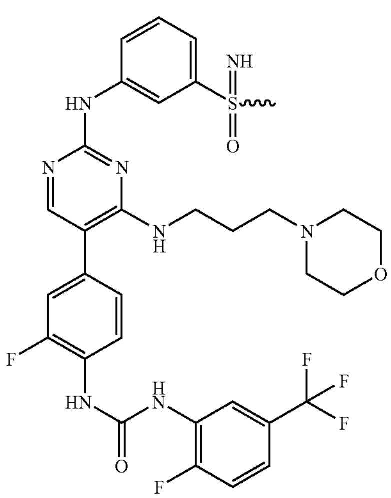 | 1-[2-Fluoro-4-(2-{[3-(RS)-(S-methylsulfonimidoyl)phenyl]amino}-4-[(3-morpholin-4-ylpropyl)amino]-pyrimidin-5-yl)phenyl]-3-[2-fluoro-5-(trifluoromethyl)-phenyl]urea | $^1$H-NMR (DMSO, 300 MHz): 9.50 (s, 1 H); 9.37 (s br, 1 H); 9.23 (s br, 1 H); 8.58-8.67 (m, 2 H); 8.23 (t, 1 H); 7.86 (mc, 1 H); 7.76 (s, 1 H); 7.33-7.53 (m, 4 H); 7.29 (dd, 1 H); 7.17 (d, 1 H); 6.68 (t br, 1 H); 4.05 (s, 1 H); 3.33-3.52 (m, 6 H); 2.97 (s, 3 H); 2.12-2.36 (m, 6 H); 1.78 (quint, 2 H). MS (ESI): [M + H]$^+$ = 705. |

| Example | Structure | Name | Analytical data |
|---|---|---|---|
| 44 | 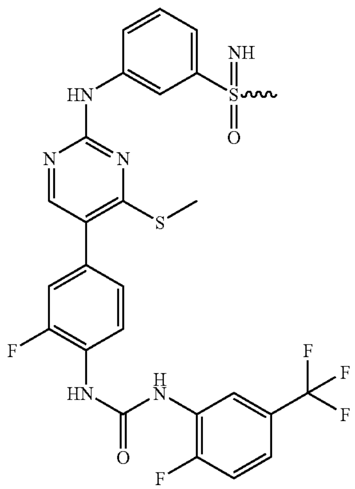 | 1-{2-Fluoro-4-[2-{[3-(RS)-(S-methylsulfonimidoyl)phenyl]amino}-4-(methylthio)-pyrimidin-5-yl]phenyl}-3-[2-fluoro-5-(trifluoromethyl)-phenyl]urea | $^1$H-NMR (DMSO, 400 MHz): 10.06 (s, 1 H); 9.41 (s br, 1 H); 9.27 (s br, 1 H); 8.57-8.65 (m, 2 H); 8.24 (t, 1 H); 8.13 (s, 1 H); 7.78-7.86 (m, 1 H); 7.44-7.54 (m, 3 H); 7.38 (mc, 2 H); 7.24 (d, 1 H); 4.12 (s, 1 H); 3.01 (s, 3 H); 2.56 (s, 3 H). MS (ESI): [M + H]$^+$ = 609. |
| 45 | 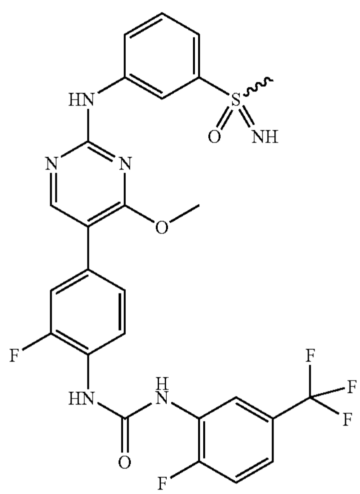 | 1-[2-Fluoro-4-(4-methoxy-2-{[3-(RS)-(S-methylsulfonimidoyl)phenyl]-amino}pyrimidin-5-yl)phenyl]-3-[2-fluoro-5-(trifluoromethyl)phenyl]urea | $^1$H-NMR (DMSO, 400 MHz): 10.08 (s, 1 H); 9.37 (s, 1 H); 9.21 (s, 1 H): 8.73 (s, 1 H); 8.62 (d, 1 H); 8.40 (s, 1 H); 8.18 (t, 1 H); 7.77-7.86 (m, 1 H); 7.44-7.56 (m, 4 H); 7.33-7.41 (m, 2 H); 4.03 (s, 3 H); 3.08 (s, 3 H). (sulfoximine = NH not detected) MS (ESI): [M + H]$^+$ = 593. |
| 46 | 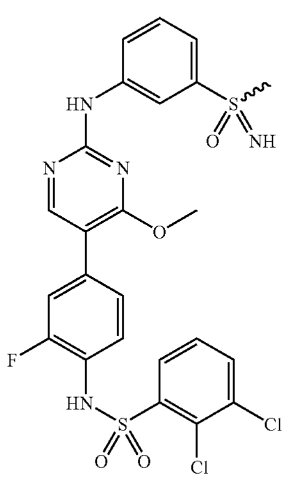 | 2,3-Dichloro-N-[2-fluoro-4-(4-methoxy-2-{[3-(RS)-(S-methylsulfonimidoyl)phenyl]amino}pyrimidin-5-yl)phenyl]benzenesulfonamide | $^1$H-NMR (DMSO, 300 MHz): 10.65 (s br, 1 H); 10.08 (s, 1 H); 8.72 (s br, 1 H); 8.37 (s, 1 H); 7.92 (d br, 2 H); 7.79-7.86 (m, 1 H); 7.46-7.54 (m, 3 H); 7.18-7.43 (m, 3 H); 4.11 (s, 1 H); 4.01 (s, 3 H); 3.03 (s, 3 H). MS (ESI): [M + H]$^+$ = 596 ($^{35}$Cl). |

The following example compounds were prepared by in situ oxidation of the thiomethyl group in Example compound 44, followed by nucleophilic displacement by the respective nucleophile according to GP 8.

| Example | Structure | Name | Analytical data |
|---|---|---|---|
| 47 | 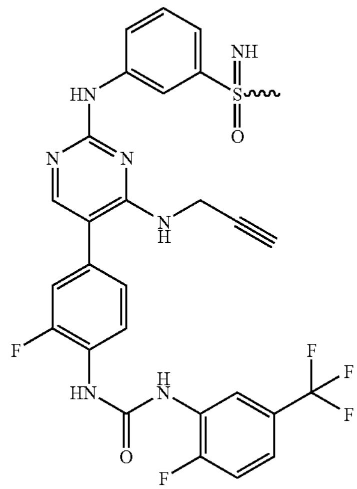 | 1-{2-Fluoro-4-[2-{[3-(RS)-(S-methylsulfonimidoyl)phenyl]amino}-4-(prop-2-yn-1-ylamino)pyrimidin-5-yl]phenyl}-3-[2-fluoro-5-(trifluoromethyl)-phenyl]urea | ¹H-NMR (DMSO, 300 MHz): 9.66 (s, 1 H); 9.41 (s br, 1 H); 9.28 (s, 1 H); 8.61-8.71 (m, 2 H); 8.28 (t, 1 H); 7.99-8.08 (m, 1 H); 7.91 (s, 1 H); 7.37-7.58 (m, 4 H); 7.30 (dd, 1 H); 7.19 (d, 1 H); 7.09 (t br, 1 H); 4.14-4.25 (m, 2 H); 4.07 (s, 1 H); 3.08 (s, 3 H); 3.01 (t, 1 H). MS (ESI): [M + H]⁺ = 616. |
| 48 | 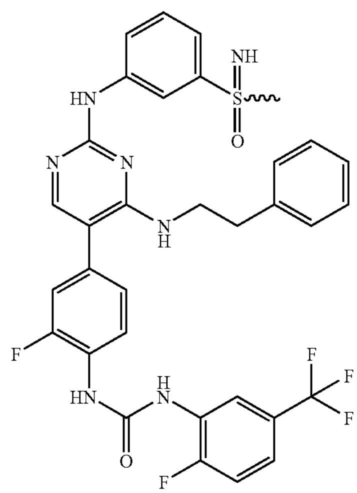 | 1-[2-Fluoro-4-(2-{[3-(RS)-(S-methylsulfonimidoyl)phenyl]amino}-4-[(2-phenylethyl)amino]-pyrimidin-5-yl)phenyl]-3-[2-fluoro-5-(trifluoromethyl)-phenyl]urea | ¹H-NMR (DMSO, 400 MHz): 9.53 (s, 1 H); 9.36 (s, 1 H); 9.22 (s, 1 H); 8.63 (d, 1 H); 8.51 (s, 1 H); 8.18 (t, 1 H); 7.98 (mc, 1 H); 7.77 (s, 1 H); 7.44-7.52 (m, 1 H); 7.33-7.42 (m, 3 H); 7.13-7.30 (m, 6 H); 7.04 (d, 1 H); 6.56 (t br, 1 H); 4.12 (s br, 1 H); 3.63 (q, 2 H); 2.97 (s, 3 H); 2.86 (t, 2 H). MS (ESI): [M + H]⁺ = 682. |
| 49 | 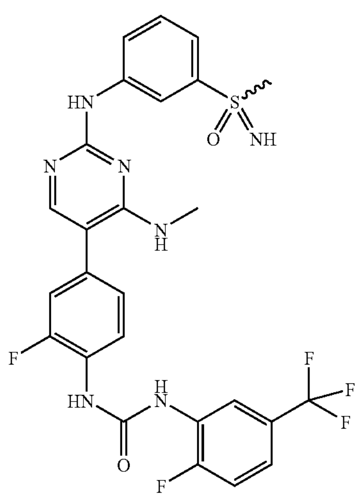 | 1-{2-Fluoro-4-[4-(methylamino)-2-{[3-(RS)-(S-methylsulfonimidoyl)phenyl]amino}-pyrimidin-5-yl]phenyl}-3-[2-fluoro-5-(trifluoromethyl)-phenyl]urea | ¹H-NMR (DMSO, 400 MHz): 10.27 (s br, 1 H); 9.40 (s, 1 H); 9.30 (s, 1 H); 8.70 (s, 1 H); 8.62 (d, 1 H); 8.27 (t, 1 H); 7.75-7.84 (m, 2 H); 7.53-7.65 (m, 3 H); 7.50 (mc, 1 H); 7.35-7.43 (m, 1 H); 7.32 (d, 1 H); 7.18 (d, 1 H); 3.22 (s, 3 H), 2.90 (d, 3 H). Sulfoximine NH not displayed. MS (ESI): [M + H]⁺ = 592. |

-continued

| Example | Name | Analytical data |
|---|---|---|
| 50 | 1-{4-[4-(Dimethylamino)-2-{[3-(RS)-(S-methylsulfonimidoyl)phenyl]amino}-pyrimidin-5-yl]-2-fluorophenyl}-3-[2-fluoro-5-(trifluoromethyl)-phenyl]urea | $^1$H-NMR (DMSO, 300 MHz): 9.82 (s, 1 H); 9.37 (s br, 1 H); 9.22 (s br, 1 H); 8.73 (s, 1 H); 8.62 (dd, 1 H); 8.20 (t, 1 H); 7.92 (s, 1 H); 7.76-7.84 (m, 1 H); 7.43-7.55 (m, 3 H); 7.32-7.42 (m, 1 H); 7.26 (dd, 1 H); 7.11 (d, 1 H); 3.16 (s, 3 H); 2.83 (s, 6 H). Sulfoximine NH not displayed. MS (ESI): [M + H]$^+$ = 606. |
| 51 | 1-{4-[4-(Ethylamino)-2-{[3-(RS)-(S-methylsulfonimidoyl)phenyl]amino}-pyrimidin-5-yl]-2-fluorophenyl}-3-[2-fluoro-5-(trifluoromethyl)-phenyl]urea | $^1$H-NMR (DMSO, 400 MHz): 10.07 (s br, 1 H); 9.39 (s, 1 H), 9.27 (s, 1 H); 8.60-8.66 (m, 2 H); 8.25 (t, 1 H); 7.75-7.83 (m, 2 H); 7.43-7.59 (m, 3 H); 7.33-7.41 (m, 1 H); 7.28 (dd, 1 H); 7.16 (d, 1 H); 3.46 (quint, 2 H); 3.14 (s, 3 H): 1.11 (t, 3 H). Sulfoximine and 4-pyrimidinyl NH groups not displayed. MS (ESI): [M + H]$^+$ =606. |
| 52 | 1-[4-(4-[(Cyanomethyl)-amino]-2-{[3-(RS)-(S-methylsulfonimidoyl)phenyl]amino}-pyrimidin-5-yl)-2-fluorophenyl]-3-[2-fluoro-5-(trifluoromethyl)-phenyl]urea | $^1$H-NMR (DMSO, 300 MHz): 9.82 (s, 1 H); 9.41 (s, 1 H); 9.28 (s, 1 H); 8.81 (s, 1 H); 8.67 (dd, 1 H); 8.28 (t, 3 H); 8.00 (s, 1 H); 7.84-7.92 (m, 1 H); 7.28-7.56 (m, 5 H); 7.22 (d, 1 H); 6.53 (s br, 1 H); 4.40 (mc, 2 H); 4.12 (s, 1 H); 3.06 (s, 3 H). |

-continued

| Example | Structure | Name | Analytical data |
|---|---|---|---|
| 53 | 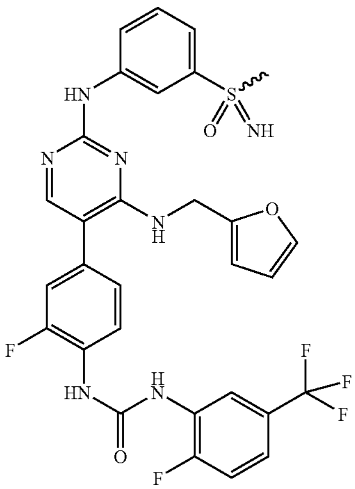 | 1-[2-Fluoro-4-(4-[(2-furylmethyl)amino]-2-{[3-(RS)-(S-methylsulfonimidoyl)phenyl]amino}-pyrimidin-5-yl)phenyl]-3-[2-fluoro-5-(trifluoromethyl)-phenyl]urea | MS (ESI): [M + H]⁺ = 658. |

The following Example compounds may be obtained using the methods described hereinbefore and/or by standard procedures known to the person skilled in the art:

Example 2.1

-continued

Example 2.2

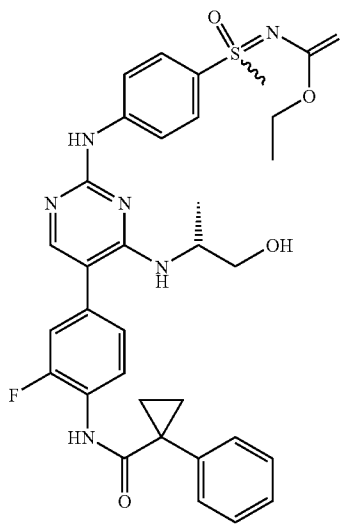
Example 2.3
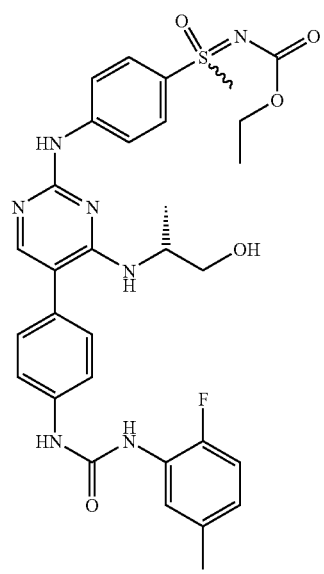
Example 2.4
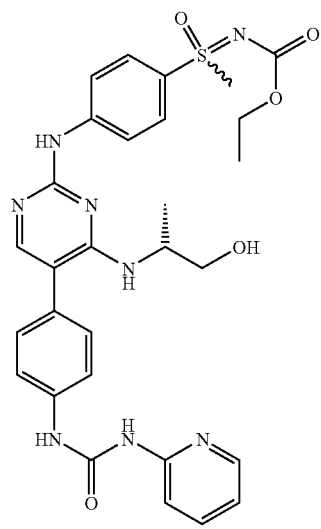
Example 2.5
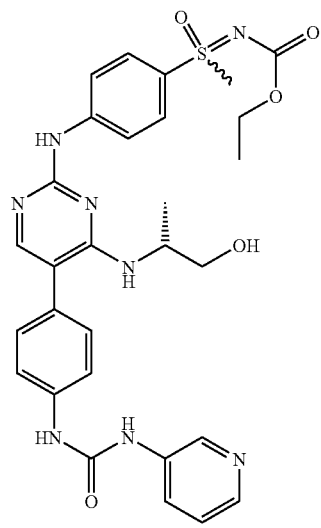
Example 2.6
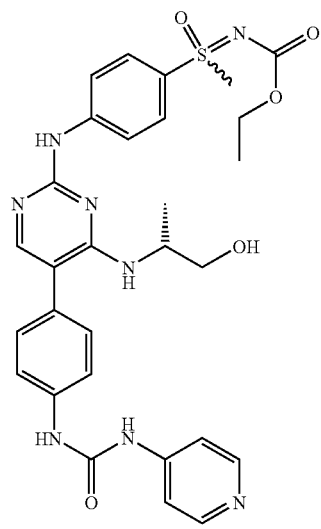
Example 2.7

| 101 -continued | 102 -continued |
|---|---|
| 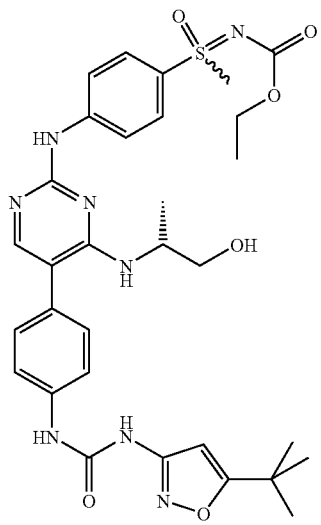<br>Example 2.8 | Example 2.10 |
| 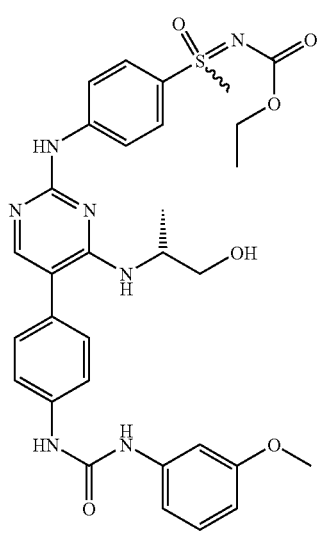<br>Example 2.9 | 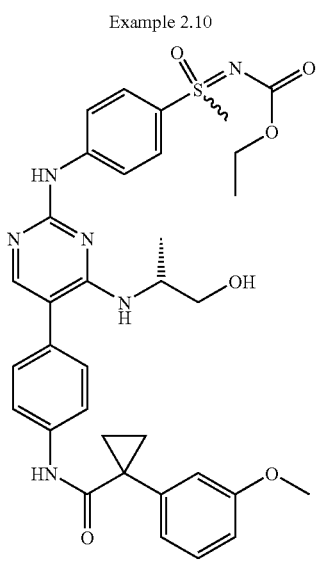<br>Example 2.11 |
| 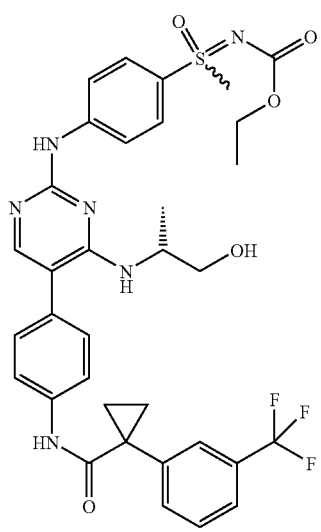 | 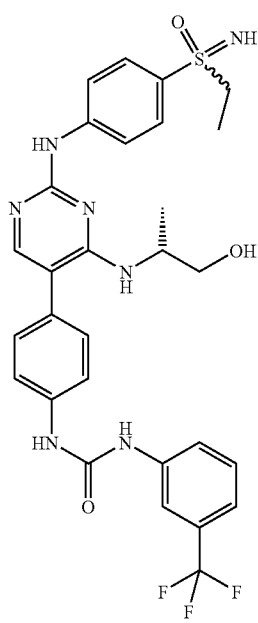<br>Example 2.12 |

-continued
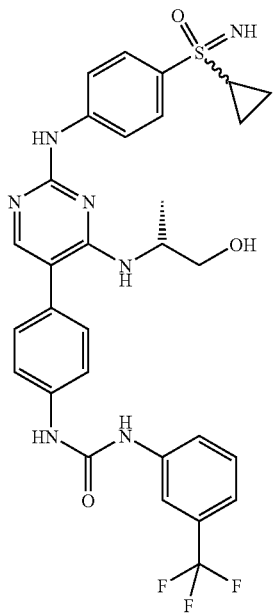
Example 2.13
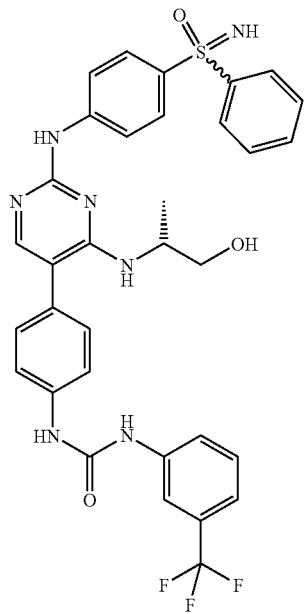
Example 2.15
-continued
Example 2.14
Example 2.16

-continued
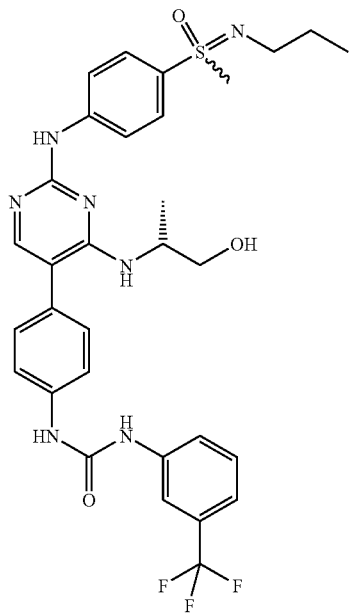
Example 2.17
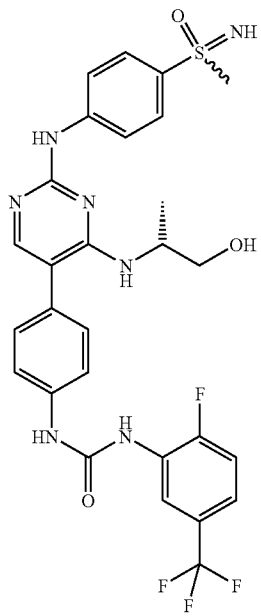
Example 2.19
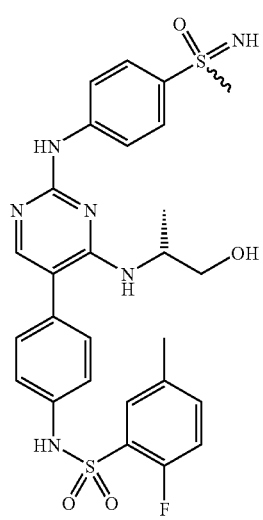
Example 2.18
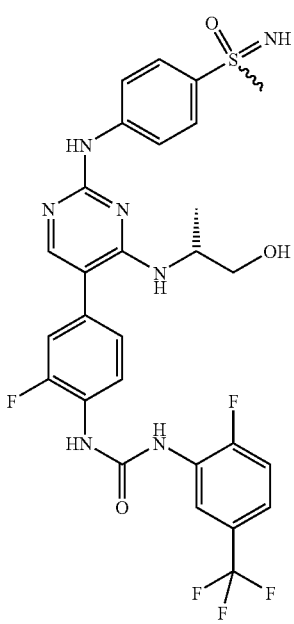
Example 2.20

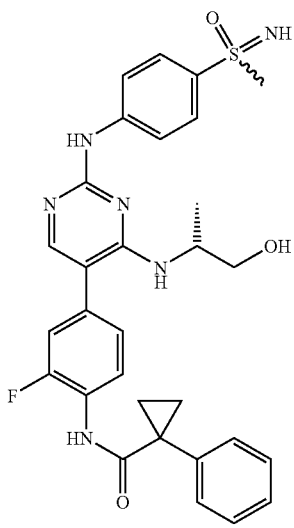
Example 2.21
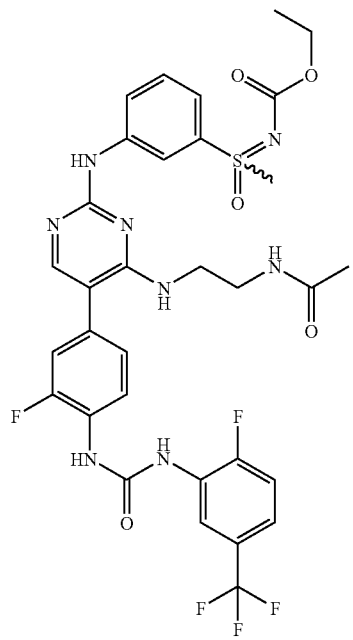
Example 2.23
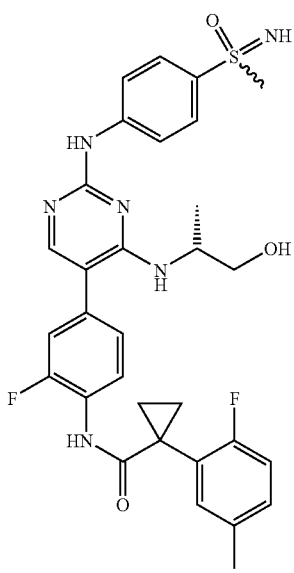
Example 2.22
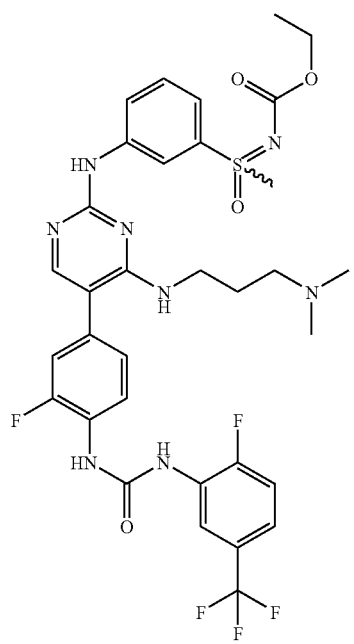
Example 2.24

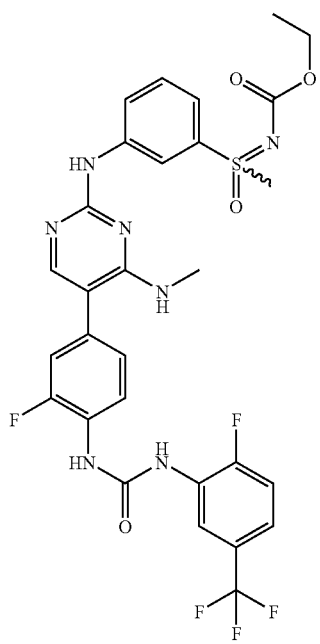
Example 2.25
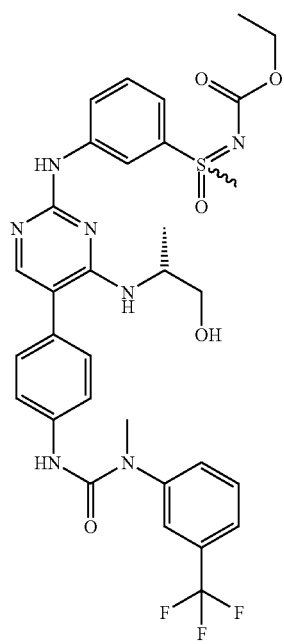
Example 2.27
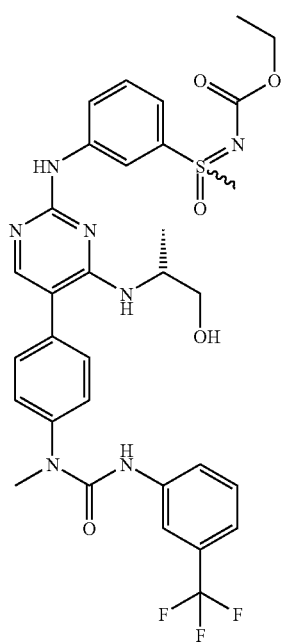
Example 2.26
Example 2.28

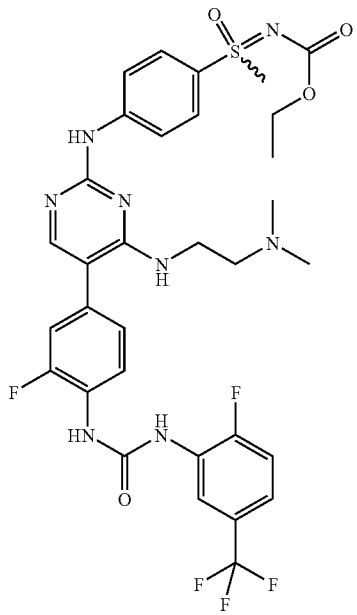
Example 2.29
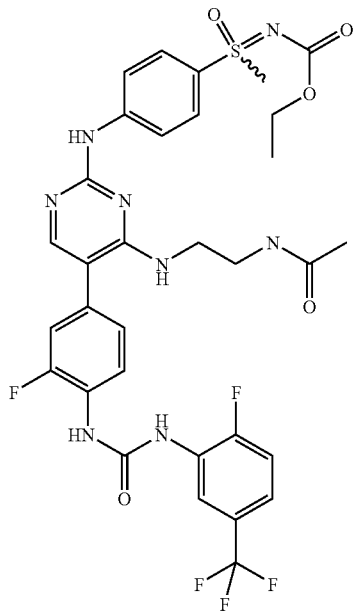
Example 2.31
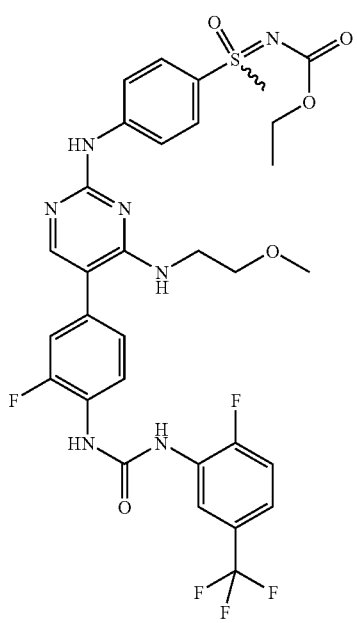
Example 2.30
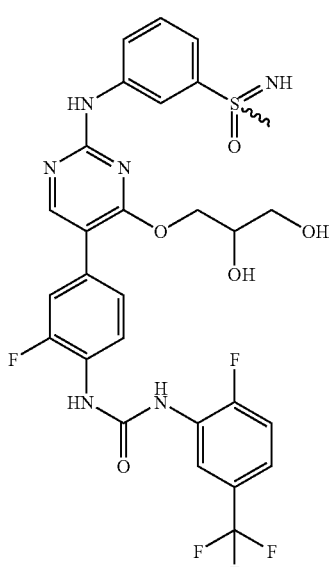
Example 2.32

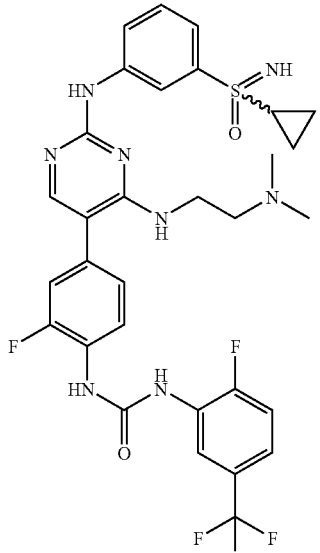

Example 2.33

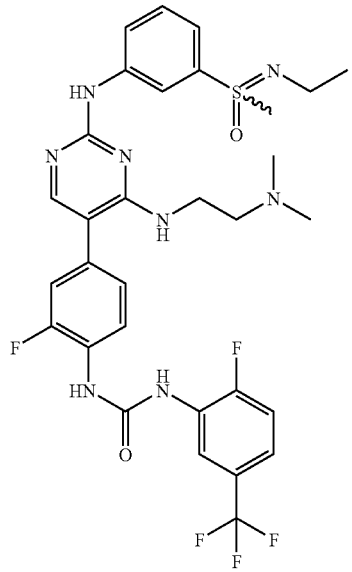

Example 2.34

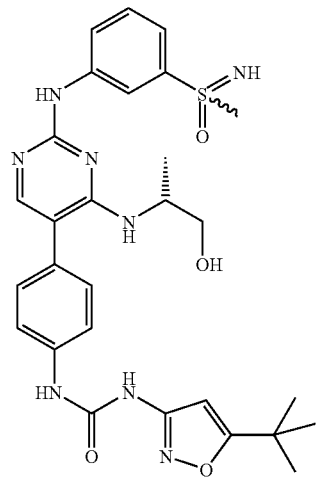

Example 2.35

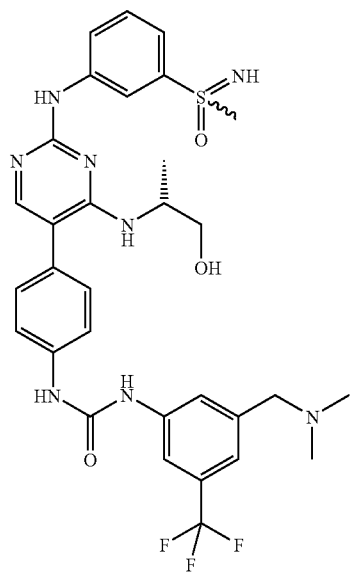

Example 2.36

Biological Data

Assay 1: Tie2 ELISA Assay

Cellular activity of compounds of the present invention as inhibitors of Tie2 kinase activity was measured employing a Tie2 ELISA assay as described in the following paragraphs. Herein CHO cell-cultures, which are stably transfected by known techniques with Tie2 using DHFR deficiency as selection marker, are stimulated by angiopoietin-2. The specific autophosphorylation of Tie2 receptors is quantified with a sandwich-ELISA using anti-Tie2 antibodies for catch and anti-phosphotyrosine antibodies coupled to HRP for detection.

Materials:
  96well tissue culture plate, sterile, Greiner
  96well FluoroNunc plate MaxiSorp Surface C, Nunc
  96well plate polypropylene for compound dilution in DMSO
  CHO Tie2/DHFR (transfected cells)

PBS−; PBS++, DMSO
MEM alpha Medium with Glutamax-I without Ribonucleosides and Deoxyribonucleosides (Gibco #32561-029) with 10% FCS after dialysis! and 1% PenStrep
Lysis buffer: 1 Tablet "Complete" protease inhibitor
1 cap Vanadate (1 mL>40 mg/mL; working solution 2 mM)
ad 50 mL with Duschl-Puffer
pH 7.6
Anti-Tie2-antibody 1:425 in Coating Buffer pH 9.6
Stock solution: 1.275 mg/mL>working.: 3 µg/mL
PBST: 2 bottles PBS(10×)+10 ml Tween, fill up with VE-water
RotiBlock 1:10 in VE-water
Anti-Phosphotyrosine HRP-Conjugated 1:10000 in 3% TopBlock 3% TopBlock in PBST
BM Chemiluminescence ELISA Substrate (POD) solution B 1:100 solution A
SF9 cell culture medium
Ang2-Fc in SF9 cell culture medium Cell Experiment:
Dispense 5×10$^4$ cells/well/98 µL in 96well tissue culture plate
Incubate at 37° C./5% CO$_2$
After 24 h add compounds according to desired concentrations
Add also to control and stimulated values without compounds 2 µL DMSO
And mix for a few min at room temperature
Add 100 µL Ang2-Fc to all wells except control, which receives insect medium
Incubate 20 min at 37° C.
Wash 3× with PBS++
Add 100 µl Lysis buffer/well and shake a couple of min at room temperature
Store lysates at 20° C. before utilizing for the ELISA Performance of Sandwich-ELISA
Coat 96well FluoroNunc Plate MaxiSorp Surface C with anti-Tie2 mAb 1:425 in Coating buffer pH 9.6; 100 µL/well overnight at 4° C.
Wash 2× with PBST
Block plates with 250 µL/well RotiBlock 1:10 in VE-water
Incubate for 2 h at room temperature or overnight at 4° C. shaking
Wash 2× in PBST
Add thawed lysates to wells and incubate overnight shaking at 4° C.
Wash 2× with PBST
Add 100 µL/well anti-Phosphotyrosine HRP-Conjugated 1:10000 in 3% TopBlock (3% TopBlock in PBST) and incubate overnight under shaking
Wash 6× with PBST
Add 100 µL/well BM Chemiluminescence ELISA Substrate (POD) solutions 1 and 2 (1:100)
Determine luminescence with the LumiCount.

Assay 2: Tie2-Kinase HTRF-Assay Without Kinase Preactivation

Tie2-inhibitory activity of compounds of the present invention was quantified employing two Tie2 HTRF assay as described in the following paragraphs.

A recombinant fusion protein of GST and the intracellular domains of Tie2, expressed in insect cells (Hi-5) and purified by Glutathion-Sepharose affinity chromatography was used as kinase. Alternatively, commercially available GST-Tie2-fusion protein (Upstate Biotechnology, Dundee, Scotland) can be used as substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany). Detection of phosphorylated product is achieved specifically by a trimeric detection complex consisting of the phosphorylated substrate, streptavidin-XLent (SA-XLent) which binds to biotin, and Europium Cryptate-labeled anti-phosphotyrosine antibody PT66 which binds to phosphorylated tyrosine.

Tie2 (3.5 ng/measurement point) was incubated for 60 min at 22° C. in the presence of 10 µM adenosine-tri-phosphate (ATP) and 1 µM substrate peptide (biotin-Ahx-EPKDDAY-PLYSDFG-NH$_2$) with different concentrations of test compounds (0 µM and concentrations in the range 0.001-20 µM) in 5 µl assay buffer [50 mM Hepes/NaOH pH 7, 10 mM MgCl$_2$, 0.5 mM MnCl$_2$, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointernational, Marcoule, France) and PT66-Eu-Chelate (0.3 ng/µl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and IC$_{50}$ values were calculated by a 4 parameter fit using an inhouse software.

Assay 3: Tie2-Kinase HTRF-Assay with Kinase Preactivation

A recombinant fusion protein of GST and the intracellular domains of Tie2, expressed in insect cells (Hi-5) and purified by Glutathion-Sepharose affinity chromatography was used as kinase. As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany).

For activation, Tie2 was incubated at a conc. 12.5 ng/µl of for 20 min at 22° C. in the presence of 250 µM adenosine-tri-phosphate (ATP) in assay buffer [50 mM Hepes/NaOH pH 7, 10 mM MgCl$_2$, 0.5 mM MnCl$_2$, 1.0 mM dithiothreitol, 0.01% NP40, protease inhibitor mixture ("Complete w/o EDTA" from Roche, 1 tablet per 2.5 ml)].

For the subsequent kinase reaction, the preactivated Tie2 (0.5 ng/measurement point) was incubated for 20 min at 22° C. in the presence of 10 µM adenosine-tri-phosphate (ATP) and 1 µM substrate peptide (biotin-Ahx-EPKDDAYPLYS-DFG-NH$_2$) with different concentrations of test compounds (0 µM and concentrations in the range 0.001-20 µM) in 5 µl assay buffer [50 mM Hepes/NaOH pH 7, 10 mM MgCl$_2$, 0.5 mM MnCl$_2$, 0.1 mM sodium ortho-vanadate, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 μl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 μM, from Cis Biointernational, Marcoule, France) and PT66-Eu-Chelate (0.3 ng/μl; a europium-chelate labelled anti-phosphotyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Assay 4: CDK2 HTRF Assay

CDK2/CycE-inhibitory activity of compounds of the present invention was quantified employing the CDK2/CycE HTRF assay as described in the following paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

CDK2/CycE was incubated for 60 min at 22° C. in the presence of different concentrations of test compounds in 5 μl assay buffer [50 mM Tris/HCl pH 8.0, 10 mM MgCl2, 1.0 mM dithiothreitol, 0.1 mM sodium ortho-vanadate, 10 μM adenosine-tri-phosphate (ATP), 0.75 μM substrate, 0.01% (v/v) Nonidet-P40 (Sigma), 1% (v/v) dimethylsulfoxide]. The concentration of CDK2/CycE was adjusted depending of the activity of the enzyme lot and was chosen appropriate to have the assay in the linear range, typical concentrations were in the range of 1 ng/ml. The reaction was stopped by the addition of 5 μl of a solution of HTRF detection reagents (0.2 μM streptavidine-XLent and 3.4 nM Phospho-(Ser) CDKs Substrate Antibody [product #2324B, Cell Signalling Technology, Danvers, Mass., USA} and 4 nM Prot-A-EuK [Protein A labeled with Europium Cryptate from Cis biointernational, France, product no. 61PRAKLB]) in an aqueous EDTA-solution (100 mM EDTA, 800 mM KF, 0.2% (w/v) bovine serum albumin in 100 mM HEPES/NaOH pH 7.0).

Compounds of the present invention were found to possess activity as inhibitors of Tie2 kinase. Preferred compounds of the present invention inhibit Tie2 kinase activity with $IC_{50}$ values below 1 μM. Surprisingly, it was found that compounds of the present invention were found to possess a selectivity profile, which is highly advantageous for Tie2 inhibitors, as they inhibit the activity of the kinase Tie2 more potently than that of the cell cycle kinase CDK2.

Selected representative data are given in the following Table. It is understood that the present invention is not limited to the compounds specified in the Table. The $IC_{50}$ values were converted to $pIC_{50}$ values, i.e. $-\log IC_{50}$ in molar concentration.

TABLE

| Example No. | Tie 2 activity (assay 2) | Tie 2 activity (assay 3) | CDK2 activity (assay 4) |
| --- | --- | --- | --- |
| 1 | + | | −− |
| 2 | + | + | −− |
| 6 | + | | −− |
| 7 | ++ | ++ | −− |
| 8 | ++ | | −− |
| 9 | + | + | −− |
| 10 | + | | −− |
| 13 | + | + | −− |
| 14 | + | | −− |
| 17 | ++ | | −− |
| 24 | + | | −− |
| 28 | ++ | + | −− |
| 29 | ++ | | −− |
| 31 | ++ | ++ | −− |
| 33 | ++ | + | −− |
| 39 | ++ | | −− |
| 42 | + | ++ | −− |
| 43 | ++ | ++ | −− |
| 44 | ++ | | −− |
| 45 | ++ | ++ | −− |
| 46 | + | + | −− |
| 48 | + | | −− |
| 49 | ++ | ++ | −− |

−− stands for $pIC_{50} < 5.0$
− stands for $pIC_{50}$ 5.0-6.0
+ stands for $pIC_{50}$ 6.0-7.0
++ stands for $pIC_{50} > 7.0$ Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 06090121.2, filed Jul. 12, 2006, and U.S. Provisional Application Ser. No. 60/831,197 filed Jul. 17, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of Formula I:

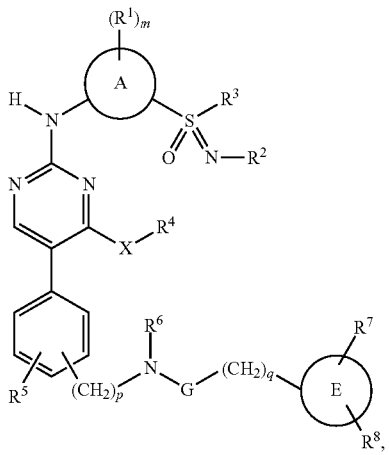

in which:

A and E are the same or different, and are each, independently from each other, phenylene or a five- or six-membered heteroarylene;

G is selected from —C(O)NR$^9$—, —S(O)$_2$—, and —C(O)—Y—;

X is selected from —O—, —S—, and —NR$^{10}$—;

Y is selected from —C$_1$-C$_6$-alkylene and —C$_3$-C$_8$-cycloalkylene;

R$^1$ is selected from hydrogen, halogen, nitro, cyano, —C$_1$-C$_6$-alkyl, —(CH$_2$)$_n$OR$^{11}$, —(CH$_2$)$_n$NR$^{11}$R$^{12}$, —(CH$_2$)$_n$C(O)R$^{13}$, —(CH$_2$)$_n$NHC(O)R$^{13}$, —(CH$_2$)$_n$NHC(O)NR$^{11}$R$^{12}$, —(CH$_2$)$_n$NHS(O)$_2$R$^{14}$, and —(CH$_2$)$_n$C(O)NR$^{11}$R$^{12}$;

R$^2$ is hydrogen, —C(O)R$^{13a}$, —S(O)$_2$R$^{14a}$, or —S(O)$_2$—(CH$_2$)$_r$—Si(R$^{15}$R$^{16}$R$^{17}$), or is selected from —C$_1$-C$_6$-alkyl, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_s$-aryl and —(CH$_2$)$_s$-heteroaryl, which in each case is unsubstituted or substituted one or more times, independently from each other, by halogen, nitro, cyano, —C$_1$-C$_6$-alkyl, —OR$^{11a}$, —NR$^{11a}$R$^{12a}$, C$_1$-C$_6$-haloalkyl, —C(O)R$^{13a}$, or —S(O)$_2$R$^{14a}$;

R$^3$ is selected from —C$_1$-C$_6$-alkyl, —C$_2$-C$_6$-alkenyl, —C$_2$-C$_6$-alkynyl, —C$_3$-C$_{10}$-cycloalkyl, —(CH$_2$)$_t$-aryl and —(CH$_2$)$_t$-heteroaryl, which in each case is unsubstituted or substituted one or more times, independently from each other, by halogen, nitro, cyano, —C$_1$-C$_6$-alkyl, —OR$^{11b}$, —NR$^{11b}$R$^{12b}$, —C$_1$-C$_6$-haloalkyl, —C(O)R$^{13b}$, or —S(O)$_2$R$^{14b}$;

R$^4$ is selected from —C$_1$-C$_6$-alkyl, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_u$-aryl and —(CH$_2$)$_u$-heteroaryl, which in each case is unsubstituted or substituted one or more times, independently from each other, by halogen, nitro, cyano, —C$_1$-C$_6$-alkyl, —C$_3$-C$_{10}$-cycloalkyl, —C$_3$-C$_{10}$-heterocycloalkyl, —OR$^{11c}$, —NR$^{11c}$R$^{12c}$, C$_1$-C$_6$-haloalkyl, —C(O)R$^{13c}$, or —S(O)$_2$R$^{14c}$;

R$^5$ is selected from hydrogen, halogen, nitro, cyano, —C$_1$-C$_6$-alkyl, —OR$^{11d}$, —NR$^{11d}$R$^{12d}$, —C$_1$-C$_6$-haloalkyl, —C$_1$-C$_6$-alkylthio and —C$_1$-C$_6$-alkylcarbonyl;

R$^6$ is hydrogen or —C$_1$-C$_6$-alkyl;

R$^7$, R$^8$ are the same or different, and are each independently selected from hydrogen, halogen, nitro, cyano, —(CH$_2$)$_v$OR$^{11e}$, —(CH$_2$)$_v$NR$^{11e}$R$^{12e}$, C$_1$-C$_6$-alkyl, —C$_3$-C$_{10}$-cycloalkyl, —C$_3$-C$_{10}$-heterocycloalkyl, —C$_1$-C$_6$-haloalkyl, —C$_1$-C$_6$-alkylthio, —(CH$_2$)$_v$C(O)R$^{13e}$, —(CH$_2$)$_v$C(O)NR$^{11e}$R$^{12e}$ and —(CH$_2$)$_v$S(O)$_2$NR$^{11e}$R$^{12e}$;

R$^9$ and R$^{10}$ are the same or different, and are each independently selected from hydrogen and —C$_1$-C$_6$-alkyl;

R$^{11}$, R$^{11a}$,
R$^{11b}$, R$^{11c}$,
R$^{11d}$, R$^{11e}$,
R$^{11f}$, R$^{11g}$,
R$^{12}$, R$^{12a}$,
R$^{12b}$, R$^{12c}$,
R$^{12d}$, R$^{12e}$, and
R$^{12f}$ are each, independently from each other, hydrogen, —C(O)R$^{13f}$, or —S(O)$_2$R$^{14f}$, or are selected from —C$_1$-C$_6$-alkyl, —C$_1$-C$_6$-alkoxy, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_x$-aryl and —(CH$_2$)$_x$-heteroaryl, wherein R$^{11}$, R$^{11a}$, R$^{11b}$, R$^{11c}$, R$^{11d}$, R$^{11e}$, R$^{11g}$, R$^{12}$, R$^{12a}$, R$^{12b}$, R$^{12c}$, R$^{12d}$, R$^{12e}$, are in each case unsubstituted or substituted one or more times, independently from each other, by halogen, nitro, cyano, —C$_1$-C$_6$-alkyl, —OR$^{11f}$, —NR$^{11f}$R$^{12f}$, —C$_1$-C$_6$-haloalkyl, —C$_1$-C$_6$-haloalkoxy, —C$_1$-C$_6$-alkylthio, —C(O)OR$^{18}$, —C(O)NR$^{18}$R$^{18a}$, or —S(O)$_2$NR$^{18}$R$^{18a}$, and wherein R$^{11f}$ and R$^{12f}$ are in each case unsubstituted or substituted one or more times, independently from each other, by halogen, nitro, cyano, —C$_1$-C$_6$-alkyl, —C$_1$-C$_6$-haloalkyl, —C$_1$-C$_6$-haloalkoxy, —C$_1$-C$_6$-alkylthio, —C(O)OR$^{18}$, —C(O)NR$^{18}$R$^{18a}$, or —S(O)$_2$NR$^{18}$R$^{18a}$, or substituted one time with —OR$^{11f}$ or —NR$^{11f}$R$^{12f}$; or R$^{11}$ and R$^{12}$,
R$^{11a}$ and R$^{12a}$,
R$^{11b}$ and R$^{12b}$,
R$^{11c}$ and R$^{12c}$,
R$^{11d}$ and R$^{12d}$,
R$^{11e}$ and R$^{12e}$,
and
R$^{12f}$ and R$^{12f}$ independently from each other, together with the nitrogen atom to which they are attached in groups —NR$^{11}$R$^{12}$, —NR$^{11a}$R$^{12a}$, —NR$^{11b}$R$^{12b}$, —NR$^{11c}$R$^{12c}$, —NR$^{11d}$R$^{12d}$, —NR$^{11e}$R$^{12e}$, and —NR$^{11f}$R$^{12f}$, each form a 3 to 10 membered heterocycloalkyl ring, wherein the carbon backbone of this heterocycloalkyl ring is optionally interrupted one or more times, the same way or differently, by a member of the group —NR$^{11g}$—, —O—, —S—, —C(O)—, —S(O)—, and —S(O)$_2$—, and optionally contains one or more double bonds;

R$^{13}$, R$^{13a}$,
R$^{13b}$, R$^{13c}$,
R$^{13e}$;

and R$^{13f}$ are each, independently from each other, hydrogen, hydroxy or —NR$^{19}$R$^{20}$, or are, independently from each other, selected from —C$_1$-C$_6$-alkyl, —C$_1$-C$_6$-alkoxy, —C$_3$-C$_{10}$-cycloalkyl and —C$_3$-C$_{10}$-heterocycloalkyl, which in each is unsubstituted or substituted one or more times, independently from each other, by halogen, nitro, cyano, —C$_1$-C$_6$-alkyl, —C$_1$-C$_6$-haloalkyl, aryl, or heteroaryl, wherein aryl or heteroaryl are unsubstituted or substituted one or more times with halogen, nitro, cyano, —C$_1$-C$_6$-alkyl, —C$_1$-C$_6$-alkoxy, —C$_1$-C$_6$-haloalkyl, or —C$_1$-C$_6$-haloalkoxy;

R$^{14}$, R$^{14a}$, $R^{14b}$, $R^{14c}$, and $R^{14f}$ are each, independently from each other, hydrogen or —$NR^{19a}R^{20a}$, or are, independently from each other, selected from —$C_1$-$C_6$-alkyl, —$C_3$-$C_{10}$-cycloalkyl and —$C_3$-$C_{10}$-heterocycloalkyl, which in each is unsubstituted or substituted one or more times, independently from each other, by halogen, nitro, cyano, —$C_1$-$C_6$-alkyl, —$C_1$-$C_6$-haloalkyl, aryl, or heteroaryl, wherein aryl or heteroaryl are unsubstituted or substituted one or more times with halogen, nitro, cyano, —$C_1$-$C_6$-alkyl, —$C_1$-$C_6$-alkoxy, —$C_1$-$C_6$-haloalkyl, or —$C_1$-$C_6$-haloalkoxy;

$R^{15}$, $R^{16}$, and $R^{17}$ are each, independently from each other, —$C_1$-$C_6$-alkyl or phenyl;

$R^{18}$ and $R^{18a}$ are each, independently from each other, hydrogen, or are selected from —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{10}$-heterocycloalkyl, —$(CH_2)_y$-aryl and —$(CH_2)_y$-heteroaryl, which in each case is unsubstituted or substituted one or more times, independently from each other, by halogen, nitro, cyano, —$C_1$-$C_6$-alkyl, or —$C_1$-$C_6$-haloalkyl; or $R^{18}$ and $R^{18a}$, together with the nitrogen atom to which they are attached form a 3 to 10 membered heterocycloalkyl ring, wherein the carbon backbone of this heterocycloalkyl ring is optionally interrupted one or more times, the same way or differently, by a member of the group —$NR^{11g}$—, —O—, —S—, —C(O)—, —S(O)—, and —$S(O)_2$—, and optionally contains one or more double bonds;

$R^{19}$, $R^{19a}$, $R^{20}$, and $R^{20a}$ are each, independently from each other, hydrogen, —$C_1$-$C_6$-alkyl or —$(CH_2)_z$-phenyl;

m and r are each, independently from each other, 1 or 2;

n, p, q, r, s, t, u, v, x, y and z are each, independently from each other, 0, 1, 2, 3 or 4, wherein when m is 2, each of the $R^1$ substituents is independent of the others, heterocycloalkyl, unless otherwise indicated, is a cycloalkyl group wherein one or more ring atoms are selected from —$NR^{11g}$—, O, S, and carbonyl, and heteroaryl is a monocyclic, bicyclic, or tricyclic aromatic ring having 3-16 ring atoms which contains at least one heteroatom, said heteroatom each being selected from oxygen, nitrogen and sulfur;

or a salt or N-oxide thereof.

2. A compound according to claim 1, wherein:

A and E are the same or different and are each phenylene or a five- or six-membered heteroarylene;

G is selected from —$C(O)NR^9$—, —$S(O)_2$—, and —C(O)—Y—;

X is selected from —O—, —S—, and —$NR^{10}$—;

Y is selected from —$C_1$-$C_6$-alkylene and —$C_3$-$C_8$-cycloalkylene;

$R^1$ is selected from hydrogen, halogen, nitro, cyano, —$C_1$-$C_6$-alkyl, —$(CH_2)_nOR^{11}$, —$(CH_2)_nNHC(O)R^{13}$, —$(CH_2)_nNHC(O)NR^{11}R^{12}$, and —$(CH_2)_nNHS(O)_2R^{14}$;

$R^2$ is hydrogen, —$C(O)R^{13a}$, —$S(O)_2R^{14a}$, or —$S(O)_2$—$(CH_2)_r$—$Si(R^{15}R^{16}R^{17})$, or is selected from —$C_1$-$C_6$-alkyl, —$C_3$-$C_{10}$-cycloalkyl, and —$(CH_2)_s$-aryl, which in each case is unsubstituted or substituted one or more times, independently from each other, by halogen, nitro, cyano, —$C_1$-$C_6$-alkyl, —$OR^{11a}$, —$NR^{11a}R^{12a}$, —$C_1$-$C_6$-haloalkyl, —$C(O)R^{13a}$, or —$S(O)_2R^{14a}$;

$R^3$ is selected from —$C_1$-$C_6$-alkyl, —$C_3$-$C_{10}$-cycloalkyl, and —$(CH_2)_t$-aryl, which in each case is unsubstituted or substituted one or more times, independently from each other, by halogen, nitro, cyano, —$C_1$-$C_6$-alkyl, —$OR^{11b}$, —$NR^{11b}R^{12b}$, —$C_1$-$C_6$-haloalkyl, —$C(O)R^{13b}$, or —$S(O)_2R^{14b}$;

$R^4$ is selected from —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{10}$-heterocycloalkyl, —$(CH_2)_u$-aryl and —$(CH_2)_u$-heteroaryl, which in each case is unsubstituted or substituted one or more times, independently from each other, by halogen, nitro, cyano, —$C_1$-$C_6$-alkyl, —$C_3$-$C_{10}$-cycloalkyl, —$C_3$-$C_{10}$-heterocycloalkyl, —$OR^{11c}$, —$NR^{11c}R^{12c}$, —$C_1$-$C_6$-haloalkyl, —$C(O)R^{13c}$, or —$S(O)_2R^{14c}$;

$R^5$ is selected from hydrogen, halogen, —$C_1$-$C_6$-alkyl, —$OR^{11d}$, and —$NR^{11d}R^{12d}$;

$R^6$ is hydrogen or —$C_1$-$C_6$-alkyl;

$R^7$, $R^8$ are the same or different, and are independently selected from hydrogen, halogen, nitro, cyano, —$(CH_2)_vOR^{11e}$, —$(CH_2)_vNR^{11e}R^{12e}$, —$C_1$-$C_6$-alkyl, —$C_3$-$C_{10}$-cycloalkyl, —$C_3$-$C_{10}$-heterocycloalkyl, —$C_1$-$C_6$-haloalkyl, —$C_1$-$C_6$-alkylthio, —$(CH_2)_vC(O)R^{13e}$, —$(CH_2)_vC(O)NR^{11e}R^{12e}$ and —$(CH_2)_vS(O)_2NR^{11e}R^{12e}$;

$R^9$ and $R^{10}$ are the same or different, and are independently selected from hydrogen and —$C_1$-$C_6$-alkyl;

$R^{11}$, $R^{11a}$, $R^{11b}$, $R^{11c}$, $R^{11d}$, $R^{11e}$, $R^{11f}$, $R^{11g}$, $R^{12}$, $R^{12a}$, $R^{12b}$, $R^{12c}$, $R^{12d}$, $R^{12e}$, and $R^{12f}$ are, independently from each other, hydrogen, —$C(O)R^{13f}$, or —$S(O)_2R^{14f}$, or are selected from —$C_1$-$C_6$-alkyl, —$C_1$-$C_6$-alkoxy, —$C_2$-$C_6$-alkenyl, —$C_2$-$C_6$-alkynyl, —$C_3$-$C_{10}$-cycloalkyl, —$C_3$-$C_{10}$-heterocycloalkyl, —$(CH_2)_x$-aryl and —$(CH_2)_x$-heteroaryl, wherein said $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are in each case unsubstituted or substituted one or more times, independently from each other, by halogen, nitro, cyano, —$C_1$-$C_6$-alkyl, —$OR^{11f}$, —$NR^{11f}R^{12f}$, $C_1$-$C_6$-haloalkyl, —$C_1$-$C_6$-haloalkoxy, —$C_1$-$C_6$-alkylthio, —$C(O)OR^{18}$, —$C(O)NR^{18}R^{18a}$, or —$S(O)_2NR^{18}R^{18a}$, and $R^{11f}$ and $R^{12f}$ are in each case unsubstituted or substituted one or more times, independently from each other, by halogen, nitro, cyano, —$C_1$-$C_6$-alkyl, —$C_1$-$C_6$-haloalkyl, —$C_1$-$C_6$-haloalkoxy, —$C_1$-$C_6$-alkylthio, —$C(O)OR^{18}$, —$C(O)NR^{18}R^{18a}$, or —$S(O)_2NR^{18}R^{18a}$, or substituted one time with —$OR^{11f}$ or —$NR^{11f}R^{12f}$; or $R^{11}$ and $R^{12}$, $R^{11a}$ and $R^{12a}$, $R^{11b}$ and $R^{12b}$, $R^{11c}$ and $R^{12c}$, $R^{11d}$ and $R^{12d}$, $R^{11e}$ and $R^{12e}$, and $R^{12f}$ and $R^{12f}$ independently from each other, together with the nitrogen atom to which they are attached in groups —$NR^{11}R^{12}$, —$NR^{11a}R^{12a}$, —$NR^{11b}R^{12b}$, —$NR^{11c}R^{12c}$, —$NR^{11d}R^{12d}$, $NR^{11e}R^{12e}$, and —$NR^{11f}R^{12f}$, and each form a 3 to 10 membered heterocycloalkyl ring, wherein the carbon backbone of this heterocycloalkyl ring is optionally interrupted one or more times, the same way or differently, by a member of the group —NR$^{11g}$—, —O, S, C(O)—, —S(O)—, and —S(O)$_2$—, and optionally contains one or more double bonds;

R$^{13}$, R$^{13a}$,
R$^{13b}$, R$^{13c}$,
R$^{13e}$, and R$^{13f}$ are each, independently from each other, hydrogen, hydroxy or —NR$^{19}$R$^{20}$, or are each, independently from each other, selected from —C$_1$-C$_6$-alkyl, —C$_1$-C$_6$-alkoxy, —C$_3$-C$_{10}$-cycloalkyl, and —C$_3$-C$_{10}$-heterocycloalkyl, which in each case is unsubstituted or substituted one or more times, independently from each other, by halogen, nitro, cyano, —C$_1$-C$_6$-alkyl, —C$_1$-C$_6$-haloalkyl, aryl, or heteroaryl, wherein aryl or heteroaryl are each unsubstituted or substituted one or more times with halogen, nitro, cyano, —C$_1$-C$_6$-alkyl, —C$_1$-C$_6$-alkoxy, —C$_1$-C$_6$-haloalkyl, or —C$_1$-C$_6$-haloalkoxy;

R$^{14}$, R$^{14a}$,
R$^{14b}$, R$^{14c}$, and R$^{14f}$ are each, independently from each other, hydrogen or —NR$^{19a}$R$^{20a}$, or are each, independently from each other, selected from —C$_1$-C$_6$-alkyl, —C$_3$-C$_{10}$-cycloalkyl, and —C$_3$-C$_{10}$-heterocycloalkyl, which in each case is unsubstituted or substituted one or more times, independently from each other, by halogen, nitro, cyano, —C$_1$-C$_6$-alkyl, —C$_1$-C$_6$-haloalkyl, aryl, or heteroaryl, wherein aryl or heteroaryl are each unsubstituted or substituted one or more times with halogen, nitro, cyano, —C$_1$-C$_6$-alkyl, —C$_1$-C$_6$-alkoxy, —C$_1$-C$_6$-haloalkyl, or —C$_1$-C$_6$-haloalkoxy;

R$^{15}$, R$^{16}$, and R$^{17}$ are each, independently from each other, —C$_1$-C$_6$-alkyl or phenyl;

R$^{18}$ and R$^{18a}$ are each, independently from each other, hydrogen, or are selected each from —C$_1$-C$_6$-alkyl, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_y$-aryl, and —(CH$_2$)$_y$-heteroaryl, which in each case is unsubstituted or substituted one or more times, independently from each other, by halogen, nitro, cyano, —C$_1$-C$_6$-alkyl, or —C$_1$-C$_6$-haloalkyl; or R$^{18}$ and R$^{18a}$, together with the nitrogen atom to which they are attached form a 3 to 10 membered heterocycloalkyl ring, wherein the carbon backbone of this heterocycloalkyl ring is optionally interrupted one or more times, the same way or differently, by a member of the group —NR$^{11g}$—, —O—, —S—, —C(O)—, —S(O)—, and —S(O)$_2$—, and optionally contains one or more double bonds;

R$^{19}$, R$^{19a}$,
R$^{20}$, and R$^{20a}$ are each, independently from each other, hydrogen, —C$_1$-C$_6$-alkyl or —(CH$_2$)$_z$-phenyl;

m is 1 or 2;
r is 2;
s and t are each, independently from each other, 0, 1, or 2;
n is 0 or 1;
p, q,
u, v, x
y and z are each, independently from each other, 0, 1, 2, 3 or 4, wherein when m is 2, each of the R$^1$ substituents are independent of each other.

3. A compound according to claim 1, wherein:

A is phenylene;
E is phenylene or a five- or six-membered heteroarylene;
G is selected from —C(O)NR$^9$—, —S(O)$_2$—, and —C(O)—Y—;
X is selected from —O—, —S—, and —NR$^{10}$—;
Y is selected from —C$_1$-C$_6$-alkylene and —C$_3$-C$_8$-cycloalkylene;
R$^1$ is hydrogen;
R$^2$ is hydrogen or —C(O)R$^{13a}$, or is selected from —C$_1$-C$_6$-alkyl, —C$_3$-C$_{10}$-cycloalkyl, and —(CH$_2$)$_s$-aryl, which in each case is unsubstituted or substituted one or more times, independently from each other, by halogen, nitro, cyano, C$_1$-C$_6$ alkyl, OR$^{11a}$, —NR$^{11a}$R$^{12a}$, or —C$_1$-C$_6$-haloalkyl;
R$^3$ is selected from a group comprising, preferably consisting of —C$_1$-C$_6$-alkyl, —C$_3$-C$_{10}$-cycloalkyl, and —(CH$_2$)$_t$-aryl, which in each case is unsubstituted or substituted one or more times, independently from each other, by halogen, nitro, cyano, —C$_1$-C$_6$-alkyl, or —C$_1$-C$_6$-haloalkyl;
R$^4$ is selected from —C$_1$-C$_6$-alkyl, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_u$-aryl and —(CH$_2$)$_u$-heteroaryl, which in each case is unsubstituted or substituted one or more times, independently from each other, by halogen, nitro, cyano, —C$_1$-C$_6$-alkyl, —C$_3$-C$_{10}$-cycloalkyl, —C$_3$-C$_{10}$-heterocycloalkyl, —OR$^{11c}$, —NR$^{11c}$R$^{12c}$, —C$_1$-C$_6$-haloalkyl, —C(O)R$^{13c}$, or —S(O)$_2$R$^{14c}$;
R$^5$ is selected from hydrogen, methyl, fluoro, and chloro;
R$^6$ is hydrogen or methyl;
R$^7$, R$^8$ are the same or different, and are each independently selected from hydrogen, halogen, nitro, cyano, —(CH$_2$)$_v$OR$^{11e}$, —(CH$_2$)$_v$NR$^{11e}$R$^{12e}$, C$_1$-C$_6$-alkyl, —C$_3$-C$_{10}$-cycloalkyl, —C$_3$-C$_{10}$-heterocycloalkyl, —C$_1$-C$_6$-haloalkyl, —C$_1$-C$_6$-alkylthio, —(CH$_2$)$_v$C(O)R$^{13e}$, —(CH$_2$)$_v$C(O)NR$^{11e}$R$^{12e}$, and —(CH$_2$)$_v$S(O)$_2$NR$^{11e}$R$^{12e}$;
R$^9$ is hydrogen or methyl;
R$^{10}$ is hydrogen;
R$^{11a}$, R$^{11b}$,
R$^{11c}$, R$^{11e}$,
R$^{11f}$, R$^{11g}$,
R$^{12a}$, R$^{12b}$,
R$^{12c}$, R$^{12e}$, and R$^{12f}$ are each, independently from each other, hydrogen, —C(O)R$^{13f}$, or —S(O)$_2$R$^{14f}$, or are selected from —C$_1$-C$_6$-alkyl, —C$_3$-C$_{10}$-cycloalkyl, and —(CH$_2$)$_x$-aryl, wherein R$^{11}$, R$^{11a}$, R$^{11b}$, R$^{11c}$, R$^{11d}$, R$^{11e}$, R$^{11g}$, R$^{12}$, R$^{12a}$, R$^{12b}$, R$^{12c}$, R$^{12d}$, R$^{12e}$, are each unsubstituted or substituted one or more times, independently from each other, by halogen, nitro, cyano, —C$_1$-C$_6$-alkyl, —OR$^{11f}$, —NR$^{11f}$R$^{12f}$, —C$_1$-C$_6$-haloalkyl, or —C$_1$-C$_6$-haloalkoxy, and R$^{11f}$ and R$^{12f}$ are each unsubstituted or substituted one or more times, independently from each other, by halogen, nitro, cyano, —C$_1$-C$_6$-alkyl, —C$_1$-C$_6$-haloalkyl, or —C$_1$-C$_6$-haloalkoxy, or substituted one time with —OR$^{11f}$ or —NR$^{11f}$R$^{12f}$; or R$^{11a}$ and R$^{12a}$,
R$^{11b}$ and R$^{12b}$,
R$^{11c}$ and R$^{12c}$,
R$^{11e}$ and R$^{12e}$,
and R$^{12f}$ and R$^{12f}$ independently from each other, together with the nitrogen atom to which they are attached in groups —NR$^{11a}$R$^{12a}$, —NR$^{11b}$R$^{12b}$, —NR$^{11c}$R$^{12c}$, —NR$^{11e}$R$^{12e}$, and NR$^{11f}$R$^{12f}$, each form a 3 to 7 membered heterocycloalkyl ring, wherein the carbon backbone of this heterocycloalkyl ring is optionally interrupted one or more times, the same way or differently, by a member of the group —$NR^{11g}$— and —O—;

$R^{13a}$, $R^{13c}$, $R^{13e}$, and $R^{13f}$ are each, independently from each other, hydrogen, hydroxy or —$NR^{19}R^{20}$, or are, independently from each other, selected from —$C_1$-$C_6$-alkyl, —$C_1$-$C_6$-alkoxy, —$C_3$-$C_{10}$-cycloalkyl, and —$C_3$-$C_{10}$-heterocycloalkyl, which in each case is unsubstituted or substituted one or more times, independently from each other, by halogen, nitro, cyano, —$C_1$-$C_6$-alkyl, or aryl, wherein aryl is unsubstituted or substituted one or more times with halogen, nitro, cyano, —$C_1$-$C_6$-alkyl, —$C_1$-$C_6$-alkoxy, —$C_1$-$C_6$-haloalkyl, or —$C_1$-$C_6$-haloalkoxy;

$R^{14c}$ and $R^{14f}$ are each, independently from each other, hydrogen or —$NR^{19a}R^{20a}$, or are, independently from each other, selected from —$C_1$-$C_6$-alkyl, —$C_3$-$C_{10}$-cycloalkyl and —$C_3$-$C_{10}$-heterocycloalkyl, which in each case is unsubstituted or substituted one or more times, independently from each other, by halogen, —$C_1$-$C_6$-alkyl, or aryl, wherein aryl is unsubstituted or substituted one or more times with halogen, nitro, cyano, —$C_1$-$C_6$-alkyl, —$C_1$-$C_6$-alkoxy, —$C_1$-$C_6$-haloalkyl, or —$C_1$-$C_6$-haloalkoxy;

$R^{19}$, $R^{19a}$, $R^{20}$, and $R^{20a}$ are each, independently from each other, hydrogen, —$C_1$-$C_6$-alkyl or —$(CH_2)_z$-phenyl;

s, t and x are each, independently from each other, 0, 1, or 2;

p, q, u, and v are each, independently from each other, 0, 1, 2, 3 or 4;

z is 0 or 1.

4. A compound according to claim 1, wherein:

A and E are each phenylene;

G is selected from —$C(O)NR^9$—, —$S(O)_2$—, and —$C(O)$—Y—;

X is selected from —O—, —S—, and —$NR^{10}$—;

Y is selected —$C_1$-$C_3$-alkylene and —$C_3$-cycloalkylene;

$R^1$ is hydrogen;

$R^2$ is hydrogen, or —$C(O)R^{13a}$;

$R^3$ is selected from —$C_1$-$C_6$-alkyl, $C_3$-$C_6$-cycloalkyl, and phenyl;

$R^4$ is selected from —$C_1$-$C_6$-alkyl, and —$(CH_2)_u$-aryl, which in each case is unsubstituted or substituted one or more times, independently from each other, by halogen, —$C_1$-$C_6$-alkyl, —$C_3$-$C_{10}$-cycloalkyl, —$C_3$-$C_{10}$-heterocycloalkyl, —$OR^{11c}$, or —$NR^{11c}R^{12c}$;

$R^5$ is selected from hydrogen, methyl, fluoro, and chloro;

$R^6$ is hydrogen;

$R^7$ is selected from hydrogen, halogen, cyano, hydroxyl, $C_1$-$C_6$-alkoxy, $C_1$-$C_6$-haloalkoxy, —$C_1$-$C_6$-alkyl, and —$C_1$-$C_6$-haloalkyl;

$R^8$ is selected from hydrogen, halogen, cyano, —$(CH_2)_vOR^{11e}$, —$(CH_2)_vNR^{11e}R^{12e}$, —$C_1$-$C_6$-alkyl, —$C_3$-$C_{10}$-cycloalkyl, —$C_3$-$C_{10}$-heterocycloalkyl, —$C_1$-$C_6$-haloalkyl, —$(CH_2)_vC(O)R^{13e}$, —$(CH_2)_vC(O)NR^{11e}R^{12e}$ and —$(CH_2)_vS(O)_2NR^{11e}R^{12e}$;

$R^9$ and $R^{10}$ are each hydrogen;

$R^{11c}$, $R^{11e}$, $R^{11f}$, $R^{11g}$, $R^{12c}$, $R^{12e}$, and $R^{12f}$ are each, independently from each other, hydrogen, or —$C(O)R^{13f}$, or are selected from —$C_1$-$C_6$-alkyl, and —$C_3$-$C_{10}$-cycloalkyl, wherein $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are each unsubstituted or substituted one or more times, independently from each other, by halogen, —$OR^{11f}$, or —$NR^{11f}R^{12f}$, and $R^{11f}$ and $R^{12f}$ are each unsubstituted or substituted one or more times, independently from each other, with halogen, or substituted one time with —$OR^{11f}$ or —$NR^{11f}R^{12f}$; or $R^{11c}$ and $R^{12c}$, $R^{11e}$ and $R^{12e}$, and $R^{12f}$ and $R^{12f}$ independently from each other, together with the nitrogen atom to which they are attached in groups —$NR^{11c}R^{12c}$, —$NR^{11e}R^{12e}$, and —$NR^{11f}R^{12f}$, each form a 3 to 7 membered heterocycloalkyl ring, wherein the carbon backbone of this heterocycloalkyl ring is optionally interrupted one or more times, the same way or differently, by a member of the group —$NR^{11g}$— and —O—;

$R^{13a}$, $R^{13e}$, and $R^{13f}$ are each, independently from each other, hydrogen, hydroxy or —$NR^{19}R^{20}$, or are, independently from each other, selected from —$C_1$-$C_6$-alkyl or —$C_1$-$C_6$-alkoxy, which in each case is unsubstituted or substituted one or more times, independently from each other, by halogen or phenyl;

$R^{19}$ and $R^{20}$ are each, independently from each other, hydrogen, —$C_1$-$C_6$-alkyl or —$(CH_2)_z$-phenyl;

p, q, and z, are each, independently of each other, 0 or 1;

u, and v are each, independently of each other, 0, 1, 2, 3, or 4.

5. A compound according to claim 1, wherein:

A and E are each phenylene;

G is selected from —$C(O)NR^9$—, —$S(O)_2$—, and —$C(O)$—Y—;

X is selected from —O—, —S—, and —$NR^{10}$—;

Y is selected from —$C_1$-$C_3$-alkylene and —$C_3$-cycloalkylene;

$R^1$ is hydrogen;

$R^2$ is hydrogen, or —$C(O)R^{13a}$;

$R^3$ is selected from —$C_1$-$C_6$-alkyl, $C_3$-$C_6$-cycloalkyl, and phenyl;

$R^4$ is selected from —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{10}$-heterocycloalkyl, —$(CH_2)_u$-aryl and —$(CH_2)_u$-heteroaryl, which in each case is unsubstituted or substituted one or more times, independently from each other, by halogen, nitro, cyano, —$C_1$-$C_6$-alkyl, —$C_3$-$C_{10}$-cycloalkyl, —$C_3$-$C_{10}$-heterocycloalkyl, —$OR^{11c}$, —$NR^{11c}R^{12c}$, $C_1$-$C_6$-haloalkyl, —$C(O)R^{13c}$, or —$S(O)_2R^{14c}$;

$R^5$ is selected from hydrogen, methyl, fluoro, and chloro;

$R^6$ is hydrogen;

$R^7$ is hydrogen, halogen, $C_1$-$C_6$-alkyl, or $C_1$-$C_6$-haloalkyl;

$R^8$ is selected from hydrogen, halogen, $C_1$-$C_6$-alkyl, $C_1$-$C_6$-alkoxy, $C_1$-$C_6$-haloalkyl, and $C_1$-$C_6$-haloalkoxy;

$R^9$ and $R^{10}$ are each hydrogen;

$R^{11a}$, $R^{11c}$, $R^{11e}$, $R^{11f}$, $R^{11g}$, $R^{12c}$, $R^{12e}$, $R^{12f}$ are each, independently from each other, hydrogen or —$C(O)R^{13f}$, or are selected from —$C_1$-$C_6$-alkyl and —$C_3$-$C_{10}$-cycloalkyl, wherein $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are unsubstituted or substituted one or more times, independently from each other, by halogen, —$OR^{11f}$, or —$NR^{11f}R^{12f}$, and wherein $R^{11f}$ and $R^{12f}$ are unsubstituted or substituted one or more times, independently from each other, with halogen, or substituted one time with —$OR^{11f}$ or —$NR^{11f}R^{12f}$; or $R^{11c}$ and $R^{12c}$, $R^{11e}$ and $R^{12e}$, and $R^{12f}$ and $R^{12f}$ independently from each other, together with the nitrogen atom to which they are attached in groups —$NR^{11c}R^{12c}$, —$NR^{11e}R^{12e}$, and —$NR^{11f}R^{12f}$, each form a 3 to 7 membered heterocycloalkyl ring, wherein the carbon backbone of this heterocycloalkyl ring is optionally interrupted one or more times, the same way or differently, by a member of the group —$NR^{11g}$— and —O—;

$R^{13a}$, $R^{13e}$, and $R^{13f}$ are each, independently from each other, hydrogen, hydroxy or —$NR^{19}R^{20}$, or are, independently from each other, selected from —$C_1$-$C_6$-alkyl, and —$C_1$-$C_6$-alkoxy, which in each case is unsubstituted or substituted one or more times, independently from each other, by halogen or phenyl;

$R^{14c}$ is hydrogen, —$NR^{19a}R^{20a}$, or —$C_1$-$C_6$-alkyl, wherein —$C_1$-$C_6$-alkyl is unsubstituted or substituted one or more times with halogen or phenyl;

$R^{19}$, $R^{19a}$, $R^{20}$, and $R^{20a}$ are each, independently from each other, hydrogen, —$C_1$-$C_6$-alkyl or —$(CH_2)_z$-phenyl;

p, q, and z, are each, independently of each other, 0 or 1;

u, and v are each, independently of each other, 0, 1, 2, 3, or 4.

6. A compound according to claim 1, wherein:

A and E are each phenylene;

G is selected from —$C(O)NR^9$—, —$S(O)_2$—, and —$C(O)$—Y—;

X is —S— or —$NR^{10}$—;

Y is $C_3$-cycloalkylene;

$R^1$ is hydrogen;

$R^2$ is hydrogen or —$C(O)OC_2H_5$;

$R^3$ is methyl;

$R^4$ is $C_1$-$C_6$-alkyl, which is unsubstituted or substituted one or more times, independently from each other, by —$C_3$-$C_{10}$-heterocycloalkyl, —$OR^{11c}$ or —$NR^{11c}R^{12c}$;

$R^5$ is hydrogen or fluoro;

$R^6$ is hydrogen;

$R^7$ is hydrogen or halogen;

$R^8$ is selected from hydrogen, halogen, —$C_1$-$C_3$-alkyl, and $C_1$-$C_3$-haloalkyl;

$R^9$ and $R^{10}$ are each hydrogen;

$R^{11c}$ and $R^{12c}$ are each, independently from each other, hydrogen or $C_1$-$C_6$-alkyl; or together with the nitrogen atom to which they are attached, form a 5- to 6-membered heterocycloalkyl ring, wherein the carbon backbone of this heterocycloalkyl ring is optionally interrupted one or more times, the same way or differently, by a member of the group —$NCH_3$— and —O—;

p, q are each 0.

7. A compound according to claim 1, wherein said compound is selected from:

N-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]phenyl}-1-phenylcyclopropanecarboxamide;

2,3-Dichloro-N-{4-[2-({3-[(RS)-N-(ethoxycarbonyl)-S-methylsulfonimidoyl]phenyl}amino)-4-{[(R)-2-hydroxy-1-methylethyl]amino}pyrimidin-5-yl]-phenyl}benzenesulfonamide;

N-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}benzene-sulfonamide;

2,3-Dichloro-N-{4-[2-({4-[(RS)-N-(ethoxycarbonyl)-S-methylsulfonimidoyl]phenyl}amino)-4-{[(R)-2-hydroxy-1-methylethyl]amino}-pyrimidin-5-yl]-phenyl}benzene-sulfonamide;

2,3-Dichloro-N-{4-[2-({4-[(RS)-N-(ethoxycarbonyl)-S-methylsulfonimidoyl]phenyl}amino)-4-{[(R)-2-hydroxy-1-methylethyl]amino}-pyrimidin-5-yl]-2-fluorophenyl}-benzenesulfonamide;

1-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[phenyl]urea;

1-{4-[2-({4-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[3-(trifluoromethyl)-phenyl]urea;

1-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]-2-fluorophenyl}-3-[2-fluoro-5-(trifluoromethyl)-phenyl]urea;

N-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]phenyl}-1-phenylcyclopropane-carboxamide;

1-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[3-(trifluoromethyl)-phenyl]urea;

N-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}benzene-sulfonamide;

1-{4-[2-({3-[(RS)-N-(Ethoxycarbonyl)-S-methylsulfonimidoyl]phenyl}amino)-4-{[(R)-2-hydroxy-1-methylethyl]amino}-pyrimidin-5-yl]-phenyl}-3-[phenyl]urea;

2,3-Dichloro-N-{4-[2-({3-[(RS)-N-(ethoxycarbonyl)-S-methylsulfonimidoyl]phenyl}amino)-4-{[(R)-2-hydroxy-1-methylethyl]amino}-pyrimidin-5-yl]-2-fluorophenyl}-benzenesulfonamide;

1-{4-[4-{[(R)-2-hydroxy-1-methylethyl]amino}-2-({3-[(RS)-N-(isopropylcarbamoyl)-S-methylsulfonimidoyl]phenyl}amino)-pyrimidin-5-yl]phenyl}-3-[3-(trifluoromethyl)-phenyl]urea;

N-{4-[4-{[(R)-2-hydroxy-1-methylethyl]amino}-2-({3-[(RS)-N-(isopropylcarbamoyl)-S-methylsulfonimidoyl]phenyl}amino)-pyrimidin-5-yl]phenyl}-1-[3-(trifluoromethyl)-phenyl]cyclopropanecarboxamide;

2,3-dichloro-N-{4-[4-{[(1R)-2-hydroxy-1-methylethyl]amino}-2-({3-[(RS)-N-(isopropylcarbamoyl)-S-methylsulfonimidoyl]phenyl}amino)-pyrimidin-5-yl]phenyl}benzene-sulfonamide;

1-{4-[2-({3-[(RS)-N-(Ethoxycarbonyl)-S-methylsulfonimidoyl]phenyl}amino)-4-(methylsulfanyl)pyrimidin-5-yl]-2-fluorophenyl}-3-[2-fluoro-5-(trifluoromethyl)phenyl]urea;

2,3-Dichloro-N-{4-[2-({3-[(RS)-N-(ethoxycarbonyl)-S-methylsulfonimidoyl]phenyl}amino)-4-(methoxy)-pyrimidin-5-yl]-2-fluorophenyl}-benzenesulfonamide;

N-{4-[4-{[(R)-2-Hydroxy-1-methylethyl]amino}-2-({3-[(RS)-S-methylsulfonimidoyl]phenyl}amino)pyrimidin-5-yl]-2-fluorophenyl}-3-[2-fluoro-5-(trifluoromethyl)phenyl]urea;

N-[4-(4-{[(R)-2-hydroxy-1-methylethyl]amino}-2-{[4-(RS)-(S-methylsulfonimidoyl)phenyl]amino}-pyrimidin-5-yl)phenyl]benzene-sulfonamide;

1-[4-(4-{[(R)-2-hydroxy-1-methylethyl]amino}-2-{[4-(RS)-(S-methylsulfonimidoyl)phenyl]amino}-pyrimidin-5-yl)phenyl]-3-phenylurea;

1-[4-(4-{[(R)-2-hydroxy-1-methylethyl]amino}-2-{[4-(RS)-(S-methylsulfonimidoyl)phenyl]amino}-pyrimidin-5-yl)phenyl]-3-[3-(trifluoromethyl)-phenyl]urea;

2,3-dichloro-N-[2-fluoro-4-(4-{[(R)-2-hydroxy-1-methylethyl]amino}-2-{[4-(RS)-(S-methylsulfonimidoyl)phenyl]amino}-pyrimidin-5-yl)phenyl]benzene-sulfonamide;

2,3-dichloro-N-[4-(4-{[(R)-2-hydroxy-1-methylethyl]amino}-2-{[4-(RS)-(S-methylsulfonimidoyl)phenyl]amino}-pyrimidin-5-yl)-phenyl]benzene-sulfonamide;

1-{4-[2-({3-[(RS)-N-(Ethoxycarbonyl)-S-methylsulfonimidoyl]phenyl}amino)-4-{[2-(pyrrolidin-1-yl)ethyl]amino}pyrimidin-5-yl]-2-fluorophenyl}-3-[2-fluoro-5-(trifluoromethyl)phenyl]urea;

1-{4-[4-{[2-N,N-(Dimethylamino)ethyl]amino}2-({3-[(RS)-N-(ethoxycarbonyl)-S-methylsulfonimidoyl]phenyl}amino)pyrimidin-5-yl]-2-fluorophenyl}-3-[2-fluoro-5-(trifluoromethyl)-phenyl]urea;

1-{4-[2-({3-[(RS)-N-(Ethoxycarbonyl)-S-methylsulfonimidoyl]phenyl}amino)-4-{[2-(N-methyl-piperazin-4-yl)ethyl]amino}pyrimidin-5-yl]-2-fluorophenyl}-3-[2-fluoro-5-(trifluoromethyl)-phenyl]urea;

1-{4-[2-({3-[(RS)-N-(Ethoxycarbonyl)-S-methylsulfonimidoyl]phenyl}amino)-4-{[2-(morpholin-4-yl)ethyl]amino}pyrimidin-5-yl]-2-fluorophenyl}-3-[2-fluoro-5-(trifluoromethyl)-phenyl]urea;

1-{4-[2-({3-[(RS)-N-(Ethoxycarbonyl)-S-methylsulfonimidoyl]phenyl}amino)-4-{[3-(morpholin-4-yl)propyl]amino}pyrimidin-5-yl]-2-fluorophenyl}-3-[2-fluoro-5-(trifluoromethyl)-phenyl]urea;

1-{4-[2-({3-[(RS)-N-(Ethoxycarbonyl)-S-methylsulfonimidoyl]phenyl}amino)-4-(methoxy)-pyrimidin-5-yl]-2-fluorophenyl}-3-[2-fluoro-5-(trifluoromethyl)-phenyl]urea;

N-{4-[4-{[(R)-2-Hydroxy-1-methylethyl]amino}-2-({4-[(RS)-S-methylsulfonimidoyl]phenyl}amino)pyrimidin-5-yl]phenyl}-1-phenylcyclopropanecarboxamide;

N-{4-[4-{[(R)-2-Hydroxy-1-methylethyl]amino}-2-({3-[(RS)-S-methylsulfonimidoyl]phenyl}amino)pyrimidin-5-yl]phenyl}-1-phenylcyclopropanecarboxamide;

1-{4-[2-({3-[(RS)-S-Methylsulfonimidoyl]phenyl}amino)-4-{[2-(pyrrolidin-1-yl)ethyl]amino}pyrimidin-5-yl]-2-fluorophenyl}-3-[2-fluoro-5-(trifluoromethyl)-phenyl]urea;

1-[4-(4-{[2-(Dimethylamino)ethyl]amino}-2-{[3-(RS)-(S-methylsulfonimidoyl)phenyl]amino}-pyrimidin-5-yl)-2-fluorophenyl]-3-[2-fluoro-5-(trifluoromethyl)-phenyl]urea;

1-[2-Fluoro-4-(4-{[2-(4-methylpiperazin-1-yl)ethyl]amino}-2-{[3-(RS)-(S-methylsulfonimidoyl)phenyl]amino}-pyrimidin-5-yl)phenyl]-3-[2-fluoro-5-(trifluoromethyl)-phenyl]urea;

1-[2-Fluoro-4-(2-{[3-(RS)-(S-methylsulfonimidoyl)phenyl]amino}-4-[(2-morpholin-4-ylethyl)amino]-pyrimidin-5-yl)phenyl]-3-[2-fluoro-5-(trifluoromethyl)-phenyl]urea;

2,3-Dichloro-N-[4-(4-{[(R)-2-hydroxy-1-methylethyl]amino}-2-{[3-(RS)-(S-methylsulfonimidoyl)phenyl]amino}-pyrimidin-5-yl)phenyl]benzene-sulfonamide;

1-[4-(4-{[(R)-2-Hydroxy-1-methylethyl]amino}-2-{[3-(RS)-(S-methylsulfonimidoyl)phenyl]amino}-pyrimidin-5-yl)phenyl]-3-[3-(trifluoromethyl)-phenyl]urea;

N-[4-(4-{[(R)-2-Hydroxy-1-methylethyl]amino}-2-{[3-(RS)-(S-methylsulfonimidoyl)phenyl]amino}-pyrimidin-5-yl)phenyl]benzene-sulfonamide;

1-[4-(4-{[(R)-2-Hydroxy-1-methylethyl]amino}-2-{[3-(RS)-(S-methylsulfonimidoyl)phenyl]amino}-pyrimidin-5-yl)phenyl]-3-phenylurea;

2,3-Dichloro-N-[2-fluoro-4-(4-{[(R)-2-hydroxy-1-methylethyl]amino}-2-{[3-(RS)-(S-methylsulfonimidoyl)phenyl]amino}-pyrimidin-5-yl)phenyl]benzene-sulfonamide;

1-[2-Fluoro-4-(2-{[3-(RS)-(S-methylsulfonimidoyl)phenyl]amino}-4-[(3-morpholin-4-ylpropyl)amino]-pyrimidin-5-yl)phenyl]-3-[2-fluoro-5-(trifluoromethyl)-phenyl]urea;

1-{2-Fluoro-4-[2-{[3-(RS)-(S-methylsulfonimidoyl)phenyl]amino}-4-(methylthio)-pyrimidin-5-yl]phenyl}-3-[2-fluoro-5-(trifluoromethyl)-phenyl]urea;

1-[2-Fluoro-4-(4-methoxy-2-{[3-(RS)-(S-methylsulfonimidoyl)phenyl]-amino}pyrimidin-5-yl)phenyl]-3-[2-fluoro-5-(trifluoromethyl)phenyl]urea;

2,3-Dichloro-N-[2-fluoro-4-(4-methoxy-2-{[3-(RS)-(S-methylsulfonimidoyl)phenyl]amino}pyrimidin-5-yl)phenyl]benzenesulfonamide;

1-{2-Fluoro-4-[2-{[3-(RS)-(S-methylsulfonimidoyl)phenyl]amino}-4-(prop-2-yn-1-ylamino)pyrimidin-5-yl]phenyl}-3-[2-fluoro-5-(trifluoromethyl)-phenyl]urea;

1-[2-Fluoro-4-(2-{[3-(RS)-(S-methylsulfonimidoyl)phenyl]amino}-4-[(2-phenylethyl)amino]-pyrimidin-5-yl)phenyl]-3-[2-fluoro-5-(trifluoromethyl)-phenyl]urea;

1-{2-Fluoro-4-[4-(methylamino)-2-{[3-(RS)-(S-methylsulfonimidoyl)phenyl]amino}-pyrimidin-5-yl]phenyl}-3-[2-fluoro-5-(trifluoromethyl)-phenyl]urea;

1-{4-[4-(Dimethylamino)-2-{[3-(RS)-(S-methylsulfonimidoyl)phenyl]amino}-pyrimidin-5-yl]-2-fluorophenyl}-3-[2-fluoro-5-(trifluoromethyl)-phenyl]urea;

1-{4-[4-(Ethylamino)-2-{[3-(RS)-(S-methylsulfonimidoyl)phenyl]amino}-pyrimidin-5-yl]-2-fluorophenyl}-3-[2-fluoro-5-(trifluoromethyl)-phenyl]urea;

1-[4-(4-[(Cyanomethyl)-amino]-2-{[3-(RS)-(S-methyl-sulfonimidoyl)phenyl]amino}-pyrimidin-5-yl)-2-fluorophenyl]-3-[2-fluoro-5-(trifluoromethyl)-phenyl]urea; and 1-[2-Fluoro-4-(4-[(2-furylmethyl)amino]-2-{[3-(RS)-(S-methylsulfonimidoyl)phenyl]amino}-pyrimidin-5-yl)phenyl]-3-[2-fluoro-5-(trifluoromethyl)-phenyl]urea; and salts thereof.

8. A compound of formula Ib:

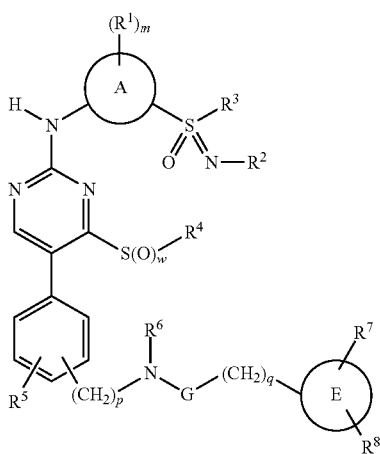

Ib in which

R$^1$, R$^2$, R$^3$, R$^5$, R$^6$, R$^7$, R$^8$, A, E, G, m, p, and q are as defined in claim 1, w is 1 or 2, and R$^4$ is —C$_1$-C$_6$-alkyl or —(CH$_2$)$_u$-aryl.

9. A compound according to claim 1, wherein:

A is phenylene;

E is phenylene or pyridinyl;

G is selected from —C(O)NH—, —C(O)N(CH$_3$)—, —S(O)$_2$—, and —C(O)—Y—;

X is selected from —O—, —S—, —NH—, and —N(CH$_3$)—;

Y is —C$_3$-C$_8$-cycloalkylene;

R$^1$ is hydrogen;

R$^5$ is hydrogen or halogen, —C$_1$-C$_6$-alkyl, —OR$^{11d}$, and —NR$^{11d}$R$^{12d}$;

R$^6$ is hydrogen or —C$_1$-C$_6$-alkyl;

R$^7$, R$^8$ are the same or different, and are independently selected from hydrogen, halogen, nitro, cyano, —(CH$_2$)$_v$OR$^{11e}$, —(CH$_2$)$_v$NR$^{11e}$R$^{12e}$, —C$_1$-C$_6$-alkyl, —C$_3$-C$_{10}$-cycloalkyl, —C$_1$-C$_6$-haloalkyl, —C$_1$-C$_6$-alkylthio, —(CH$_2$)$_s$C(O)R$^{13e}$, —(CH$_2$)$_s$C(O)NR$^{11e}$R$^{12e}$ and —(CH$_2$)$_s$S(O)$_2$NR$^{11e}$R$^{12e}$;

R$^{11a}$, R$^{11b}$, R$^{11c}$, R$^{11d}$, R$^{11e}$, R$^{11f}$, R$^{11g}$, R$^{12a}$, R$^{12b}$, R$^{12c}$, R$^{12d}$, R$^{12e}$, and R$^{12f}$ are, independently from each other, hydrogen, —C(O)R$^{13f}$, or —S(O)$_2$R$^{14f}$, or are selected from —C$_1$-C$_6$-alkyl, —C$_1$-C$_6$-alkoxy, —C$_2$-C$_6$-alkenyl, —C$_2$-C$_6$-alkynyl, —C$_3$-C$_{10}$-cycloalkyl, —(CH$_2$)$_x$-aryl and —(CH$_2$)$_x$-heteroaryl, wherein said R$^{11}$, R$^{11a}$, R$^{11b}$, R$^{11c}$, R$^{11d}$, R$^{11e}$, R$^{11g}$, R$^{12}$, R$^{12a}$, R$^{12b}$, R$^{12c}$, R$^{12d}$, R$^{12e}$, are in each case unsubstituted or substituted one or more times, independently from each other, by halogen, nitro, cyano, —C$_1$-C$_6$-alkyl, —OR$^{11f}$, —NR$^{11f}$R$^{12f}$, —C$_1$-C$_6$-haloalkyl, —C$_1$-C$_6$-haloalkoxy, —C$_1$-C$_6$-alkylthio, —C(O)OR$^{18}$, —C(O)NR$^{18}$R$^{18a}$, or —S(O)$_2$NR$^{18}$R$^{18a}$, and R$^{11f}$ and R$^{12f}$ are in each case unsubstituted or substituted one or more times, independently from each other, by halogen, nitro, cyano, —C$_1$-C$_6$-alkyl, —C$_1$-C$_6$-haloalkyl, —C$_1$-C$_6$-haloalkoxy, —C$_1$-C$_6$-alkylthio, —C(O)OR$^{18}$, —C(O)NR$^{18}$R$^{18a}$, or —S(O)$_2$NR$^{18}$R$^{18a}$;

R$^{13a}$, R$^{13b}$, R$^{13c}$, R$^{13e}$, and R$^{13f}$ are each, independently from each other, hydrogen, hydroxy or —NR$^{19}$R$^{20}$, or are each, independently from each other, selected from —C$_1$-C$_6$-alkyl, —C$_1$-C$_6$-alkoxy, and —C$_3$-C$_{10}$-cycloalkyl, which in each case is unsubstituted or substituted one or more times, independently from each other, by halogen, nitro, cyano, —C$_1$-C$_6$-alkyl, —C$_1$-C$_6$-haloalkyl, or aryl, wherein aryl is unsubstituted or substituted one or more times with halogen, nitro, cyano, —C$_1$-C$_6$-alkyl, —C$_1$-C$_6$-alkoxy, —C$_1$-C$_6$-haloalkyl, or —C$_1$-C$_6$-haloalkoxy;

R$^{14a}$, R$^{14b}$, R$^{14c}$, and R$^{14f}$ are each, independently from each other, hydrogen or —NR$^{19a}$R$^{20a}$, or are each, independently from each other, selected from —C$_1$-C$_6$-alkyl, and —C$_3$-C$_{10}$-cycloalkyl, which in each case is unsubstituted or substituted one or more times, independently from each other, by halogen, nitro, cyano, —C$_1$-C$_6$-alkyl, —C$_1$-C$_6$-haloalkyl, or aryl, wherein aryl is unsubstituted or substituted one or more times with halogen, nitro, cyano, —C$_1$-C$_6$-alkyl, —C$_1$-C$_6$-alkoxy, —C$_1$-C$_6$-haloalkyl, or —C$_1$-C$_6$-haloalkoxy;

R$^{18}$ and R$^{18a}$ are each, independently from each other, hydrogen, or are selected each from —C$_1$-C$_6$-alkyl, —C$_2$-C$_6$-alkenyl, —C$_2$-C$_6$-alkynyl, —C$_3$-C$_{10}$-cycloalkyl, and —(CH$_2$)$_y$-aryl, which in each case is unsubstituted or substituted one or more times, independently from each other, by halogen, nitro, cyano, —C$_1$-C$_6$-alkyl, or —C$_1$-C$_6$-haloalkyl;

R$^{19}$, R$^{19a}$, R$^{20}$, and R$^{20a}$ are each, independently from each other, hydrogen, —C$_1$-C$_6$-alkyl or —(CH$_2$)$_z$-phenyl; and p and q are each 0.

10. A compound according to claim 1, wherein

R$^{11}$, R$^{11a}$, R$^{11b}$, R$^{11c}$, R$^{11d}$, R$^{11e}$, R$^{11f}$, R$^{11g}$, R$^{12}$, R$^{12a}$, R$^{12b}$, R$^{12c}$, R$^{12d}$, R$^{12e}$, and R$^{12f}$ are each, independently from each other, hydrogen, —C(O)R$^{13f}$, or —S(O)$_2$R$^{14f}$, or are selected from —C$_1$-C$_6$-alkyl, —C$_1$-C$_6$-alkoxy, —C$_2$-C$_6$-alkenyl, —C$_2$-C$_6$-alkynyl, —C$_3$-C$_{10}$-cycloalkyl, —C$_3$-C$_{10}$-heterocycloalkyl, —(CH$_2$)$_x$-aryl and —(CH$_2$)$_x$-heteroaryl, wherein R$^{11}$, R$^{11a}$, R$^{11b}$, R$^{11c}$, R$^{11d}$, R$^{11e}$, R$^{11g}$, R$^{12}$, R$^{12a}$, R$^{12b}$, R$^{12c}$, R$^{12d}$, R$^{12e}$, are in each case unsubstituted or substituted one or more times, independently from each other, by halogen, nitro, cyano, —C$_1$-C$_6$-alkyl, —OR$^{11f}$, —NR$^{11f}$R$^{12f}$, —C$_1$-C$_6$-haloalkyl, —C$_1$-C$_6$-haloalkoxy, —C$_1$-C$_6$-alkylthio, —C(O)OR$^{18}$, —C(O)NR$^{18}$R$^{18a}$, or —S(O)$_2$NR$^{18}$R$^{18a}$, and wherein R$^{11f}$ and R$^{12f}$ are in each case unsubstituted or substituted one or more times, independently from each other, by halogen, nitro, cyano, —$C_1$-$C_6$-alkyl, —$C_1$-$C_6$-haloalkyl, —$C_1$-$C_6$-haloalkoxy, —$C_1$-$C_6$-alkylthio, —C(O)OR$^{18}$, —C(O)NR$^{18}$R$^{18a}$, or —S(O)$_2$NR$^{18}$R$^{18a}$; or $R^{11}$ and $R^{12}$, $R^{11a}$ and $R^{12a}$, $R^{11b}$ and $R^{12b}$, $R^{11c}$ and $R^{12c}$, $R^{11d}$ and $R^{12d}$, $R^{11e}$ and $R^{12e}$, and $R^{12f}$ and $R^{12f}$ independently from each other, together with the nitrogen atom to which they are attached in groups —NR$^{11}$R$^{12}$, —NR$^{11a}$R$^{12a}$, —NR$^{11b}$R$^{12b}$, —NR$^{11c}$R$^{12c}$, —NR$^{11d}$R$^{12d}$, NR$^{11e}$R$^{12e}$, and —NR$^{11f}$R$^{12f}$, each form a 3 to 10 membered heterocycloalkyl ring, wherein the carbon backbone of this heterocycloalkyl ring is optionally interrupted one or more times, the same way or differently, by a member of the group —NR$^{11g}$—, —O—, —S—, —C(O)—, —S(O)—, and —S(O)$_2$—, and optionally contains one or more double bonds.

11. A compound according to claim 2,
wherein
$R^{11}$, $R^{11a}$, $R^{11b}$, $R^{11c}$, $R^{11d}$, $R^{11e}$, $R^{11f}$, $R^{11g}$, $R^{12}$, $R^{12a}$, $R^{12b}$, $R^{12c}$, $R^{12d}$, $R^{12e}$, and $R^{12f}$ are, independently from each other, hydrogen, —C(O)R$^{13f}$, or —S(O)$_2$R$^{14f}$, or are selected from —$C_1$-$C_6$-alkyl, —$C_1$-$C_6$-alkoxy, —$C_2$-$C_6$-alkenyl, —$C_2$-$C_6$-alkynyl, —$C_3$-$C_{10}$-cycloalkyl, —$C_3$-$C_{10}$-heterocycloalkyl, —(CH$_2$)$_x$-aryl and —(CH$_2$)$_x$-heteroaryl, wherein said $R^{11}$, $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are in each case unsubstituted or substituted one or more times, independently from each other, by halogen, nitro, cyano, —$C_1$-$C_6$-alkyl, —OR$^{11f}$, —NR$^{11f}$R$^{12f}$, —$C_1$-$C_6$-haloalkyl, —$C_1$-$C_6$-haloalkoxy, —$C_1$-$C_6$-alkylthio, —C(O)OR$^{18}$, —C(O)NR$^{18}$R$^{18a}$, or —S(O)$_2$NR$^{18}$R$^{18a}$, and wherein $R^{11f}$ and $R^{12f}$ are in each case unsubstituted or substituted one or more times, independently from each other, by halogen, nitro, cyano, —$C_1$-$C_6$-alkyl, —$C_1$-$C_6$-haloalkyl, —$C_1$-$C_6$-haloalkoxy, —$C_1$-$C_6$-alkylthio, —C(O)OR$^{18}$, —C(O)NR$^{18}$R$^{18a}$, or —S(O)$_2$NR$^{18}$R$^{18a}$, or substituted one time with —OR$^{11f}$ or —NR$^{11f}$R$^{12f}$; or $R^{11}$ and $R^{12}$, $R^{11a}$ and $R^{12a}$, $R^{11b}$ and $R^{12b}$, $R^{11c}$ and $R^{12c}$, $R^{11d}$ and $R^{12d}$, $R^{11e}$ and $R^{12e}$, and $R^{12f}$ and $R^{12f}$ independently from each other, together with the nitrogen atom to which they are attached in groups —NR$^{11}$R$^{12}$, —NR$^{11a}$R$^{12a}$, —NR$^{11b}$R$^{12b}$, —NR$^{11c}$R$^{12c}$, —NR$^{11d}$R$^{12d}$, NR$^{11e}$R$^{12e}$, and —NR$^{11f}$R$^{12f}$, each form a 3 to 10 membered heterocycloalkyl ring, wherein the carbon backbone of this heterocycloalkyl ring is optionally interrupted one or more times, the same way or differently, by a member of the group —NR$^{11g}$—, —O—, —S—, —C(O)—, —S(O)—, and —S(O)$_2$—, and optionally contains one or more double bonds.

12. A compound according to claim 3,
wherein
$R^{11a}$, $R^{11b}$, $R^{11c}$, $R^{11e}$, $R^{11f}$, $R^{11g}$, $R^{12a}$, $R^{12b}$, $R^{12c}$, $R^{12e}$, and $R^{12f}$ are, are each independently from each other, hydrogen, —C(O)R$^{13f}$, or —S(O)$_2$R$^{14f}$, or are selected from —$C_1$-$C_6$-alkyl, —$C_3$-$C_{10}$-cycloalkyl, and —(CH$_2$)$_x$-aryl, wherein $R^{11a}$, $R^{11b}$, $R^{11c}$, $R^{11d}$, $R^{11e}$, $R^{11g}$, $R^{12}$, $R^{12a}$, $R^{12b}$, $R^{12c}$, $R^{12d}$, $R^{12e}$, are each unsubstituted or substituted one or more times, independently from each other, by halogen, nitro, cyano, —$C_1$-$C_6$-alkyl, —OR$^{11f}$, —NR$^{11f}$R$^{12f}$, —$C_1$-$C_6$-haloalkyl, or —$C_1$-$C_6$-haloalkoxy, and wherein $R^{11f}$ and $R^{12f}$ are each unsubstituted or substituted one or more times, independently from each other, by halogen, nitro, cyano, —$C_1$-$C_6$-alkyl, —$C_1$-$C_6$-haloalkyl, or —$C_1$-$C_6$-haloalkoxy, or substituted one time with —OR$^{11f}$ or —NR$^{11f}$R$^{12f}$; or $R^{11a}$ and $R^{12a}$, $R^{11b}$ and $R^{12b}$, $R^{11c}$ and $R^{12c}$, $R^{11e}$ and $R^{12e}$, and $R^{12f}$ and $R^{12f}$ independently from each other, together with the nitrogen atom to which they are attached in groups —NR$^{11a}$R$^{12a}$, —NR$^{11b}$R$^{12b}$, —NR$^{11c}$R$^{12c}$, —NR$^{11e}$R$^{12e}$, and NR$^{11f}$R$^{12f}$, each form a 3 to 7 membered heterocycloalkyl ring, wherein the carbon backbone of this heterocycloalkyl ring is optionally interrupted one or more times, the same way or differently, by a member of the group —NR$^{11g}$— and —O—.

13. A compound according to claim 4,
wherein
$R^{11c}$, $R^{11e}$, $R^{11f}$, $R^{11g}$, $R^{12c}$, $R^{12e}$, and $R^{12f}$ are each, independently from each other, hydrogen, or —C(O)R$^{13f}$, or are selected from —$C_1$-$C_6$-alkyl, and —$C_3$-$C_{10}$-cycloalkyl, wherein $R^{11c}$, $R^{11d}$, $R^{11e}$, $R^{11g}$, $R^{12c}$, and $R^{12e}$, are each unsubstituted or substituted one or more times, independently from each other, by halogen, —OR$^{11f}$, or —NR$^{11f}$R$^{12f}$, and wherein $R^{11f}$ and $R^{12f}$ are each unsubstituted or substituted one or more times, independently from each other, with halogen, or substituted one time with —OR$^{11f}$ or —NR$^{11f}$R$^{12f}$; or $R^{11c}$ and $R^{12c}$, $R^{11e}$ and $R^{12e}$, and $R^{12f}$ and $R^{12f}$ independently from each other, together with the nitrogen atom to which they are attached in groups —NR$^{11c}$R$^{12c}$, —NR$^{11e}$R$^{12e}$, and —NR$^{11f}$R$^{12f}$, each form a 3 to 7 membered heterocycloalkyl ring, wherein the carbon backbone of this heterocycloalkyl ring is optionally interrupted one or more times, the same way or differently, by a member of the group —NR$^{11g}$— and —O—.

14. A compound according to claim 5,
wherein
$R^{11a}$, $R^{11c}$, $R^{11e}$, $R^{11f}$, $R^{11g}$, $R^{12c}$, $R^{12e}$, and $R^{12f}$ are each, independently from each other, hydrogen or —C(O)R$^{13f}$, or are selected from —$C_1$-$C_6$-alkyl and —$C_3$-$C_{10}$-cycloalkyl, wherein $R^{11a}$, $R^{11c}$, $R^{11e}$, $R^{11g}$, $R^{12c}$, and $R^{12e}$ are unsubstituted or substituted one or more times, independently from each other, by halogen, —OR$^{11f}$, or —NR$^{11f}$R$^{12f}$, and wherein $R^{11f}$ and $R^{12f}$ are unsubstituted or substituted one or more times, independently from each other, with halogen, or substituted one time with —OR$^{11f}$ or —NR$^{11f}$R$^{12f}$; or $R^{11c}$ and $R^{12c}$, $R^{11e}$ and $R^{12e}$, and $R^{12f}$ and $R^{12f}$ independently from each other, together with the nitrogen atom to which they are attached in groups —NR$^{11c}$R$^{12c}$, —NR$^{11e}$R$^{12e}$, and —NR$^{11f}$R$^{12f}$, each form a 3 to 7 membered heterocycloalkyl ring, wherein the carbon backbone of this heterocycloalkyl ring is optionally interrupted one or more times, the same way or differently, by a member of the group —NR[11g]— and —O—.
15. A compound according to claim 1, wherein said compound is of one of the following formulas:
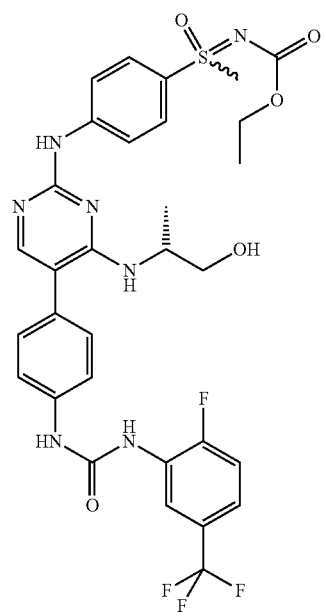
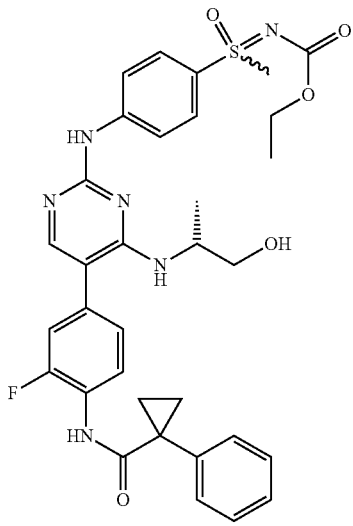
-continued
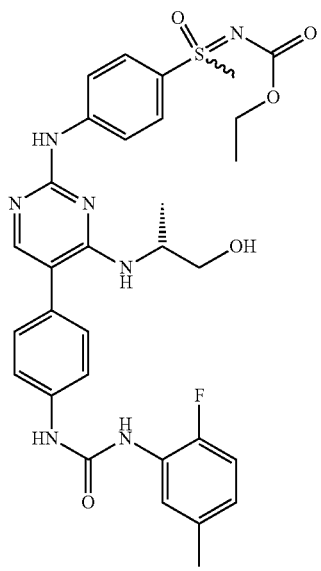
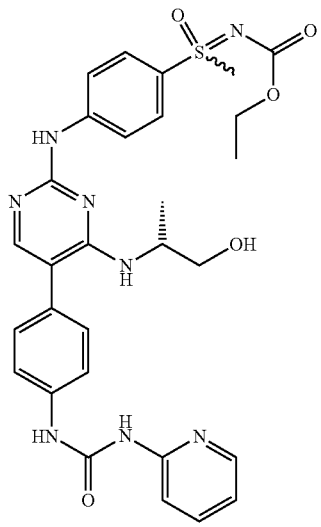

137
-continued
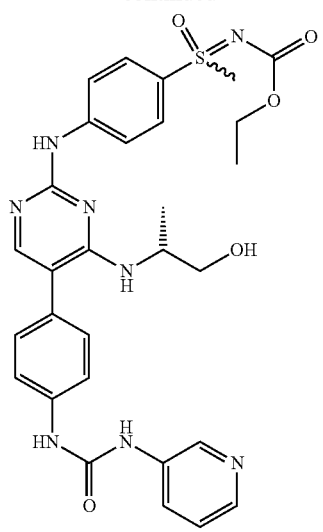
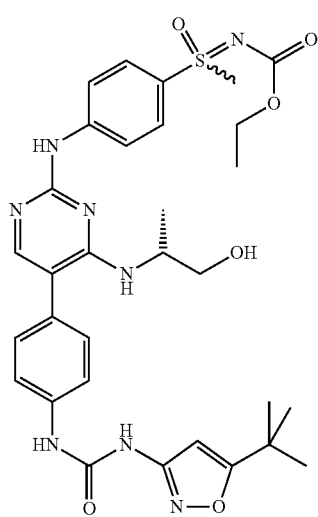
138
-continued
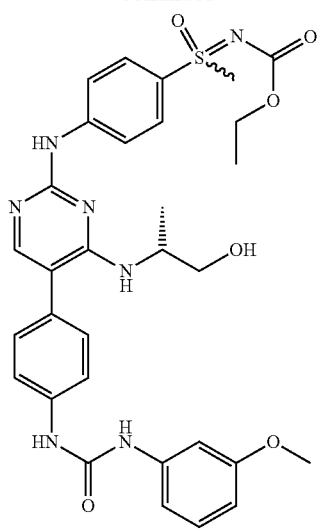
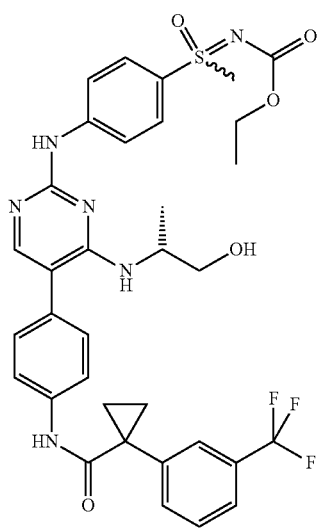
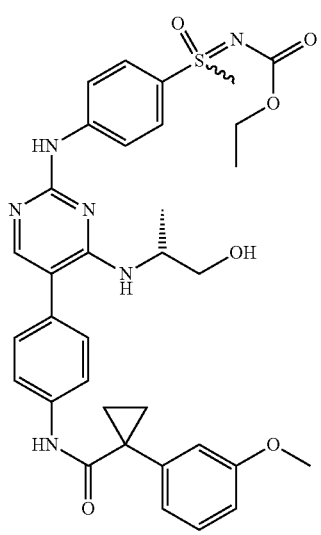

139
-continued
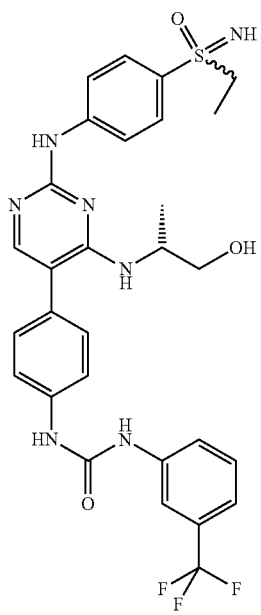
140
-continued
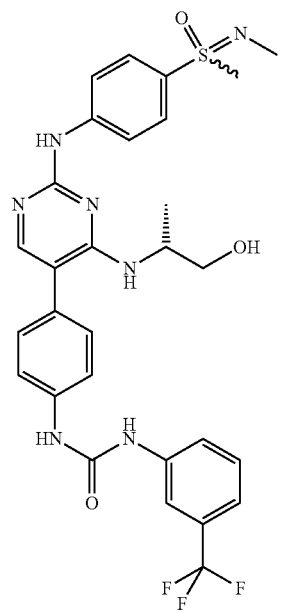
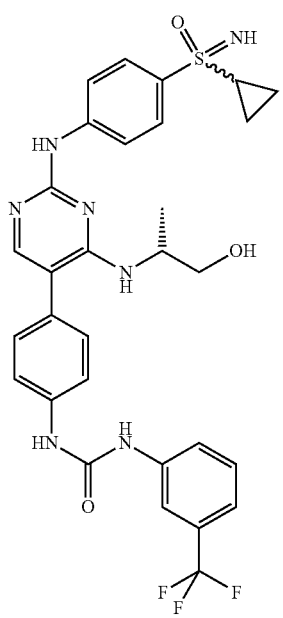
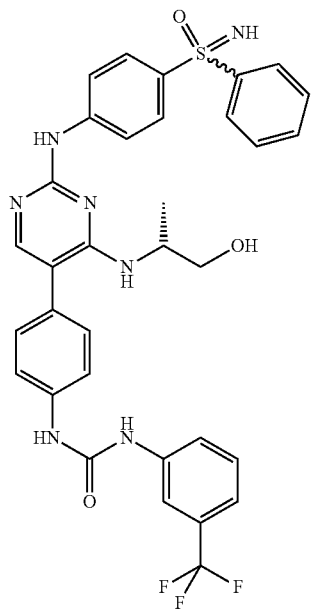

141
-continued
142
-continued
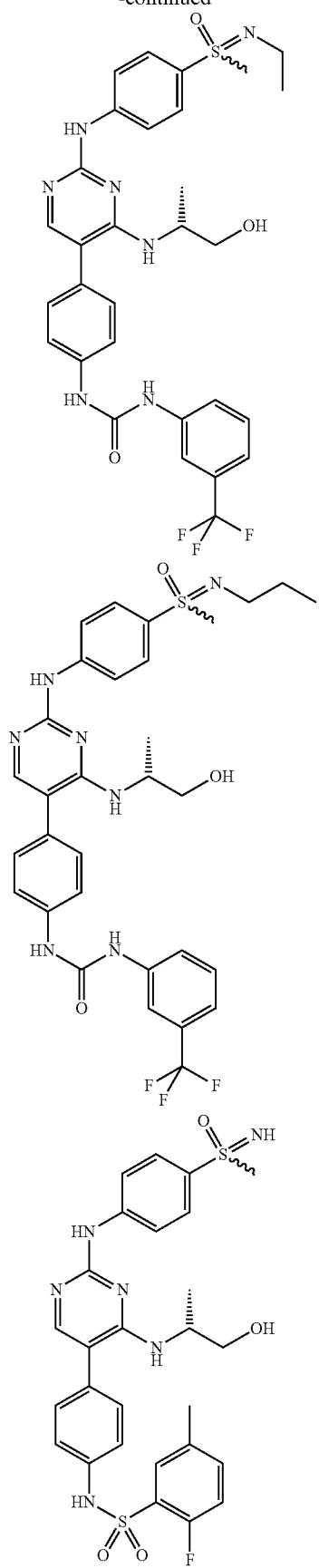
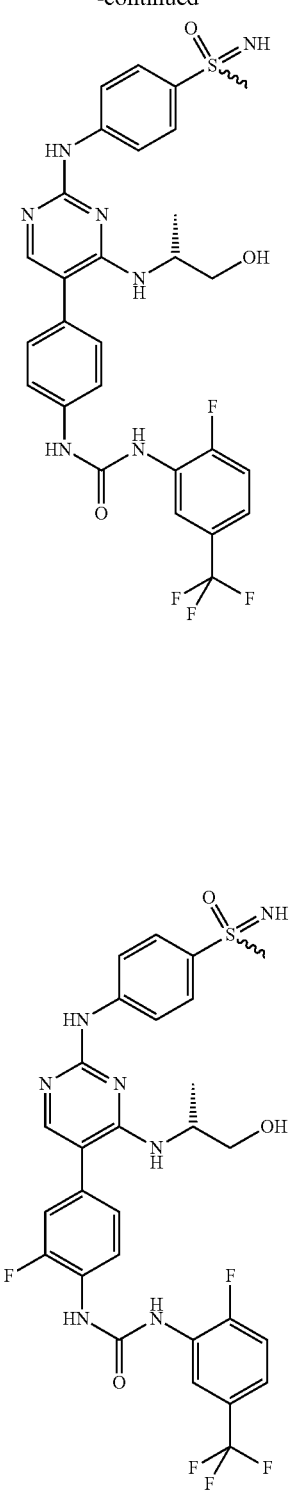

143
-continued
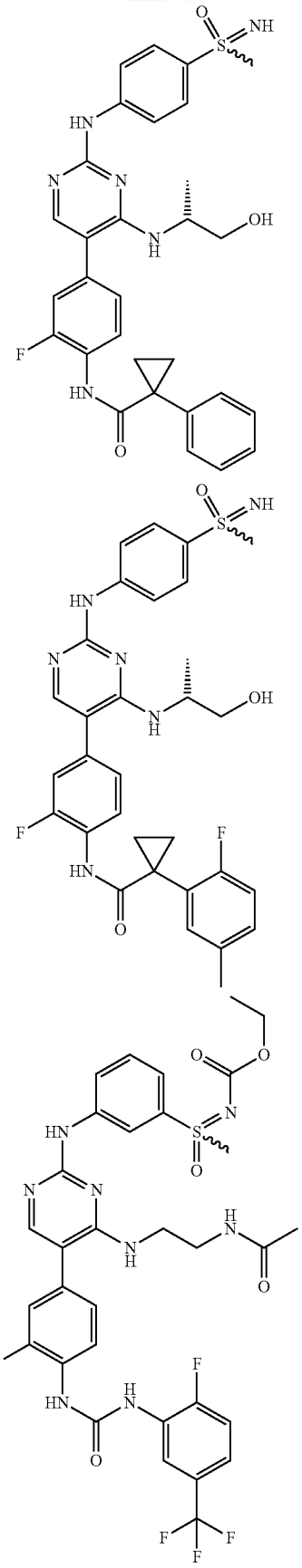
144
-continued
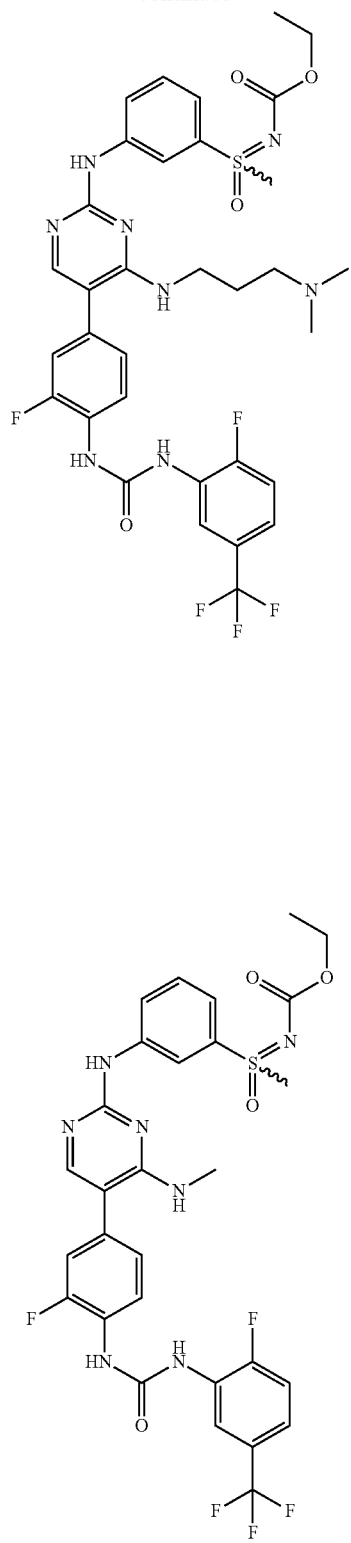

145
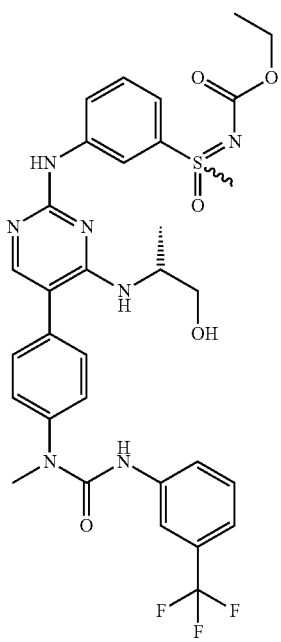
146
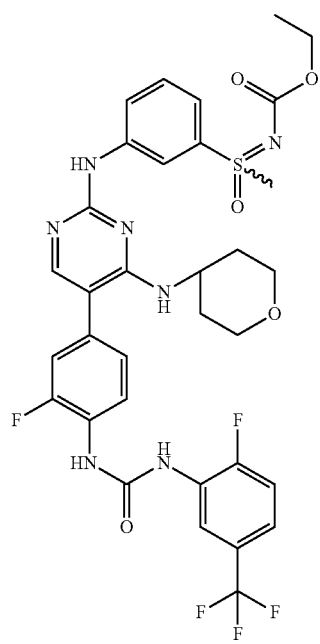
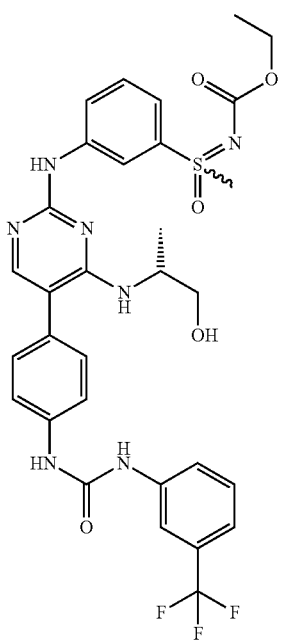
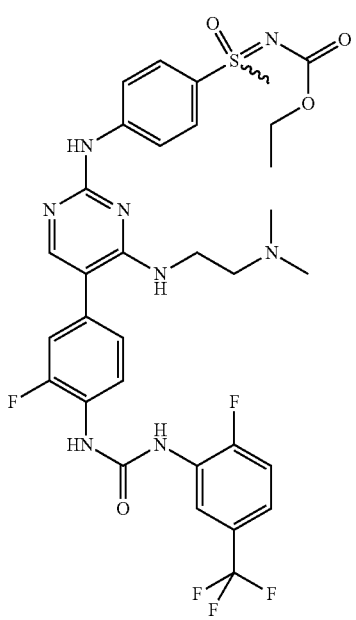

147
-continued
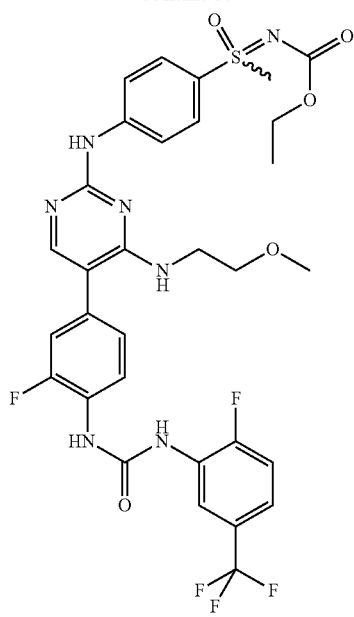
148
-continued
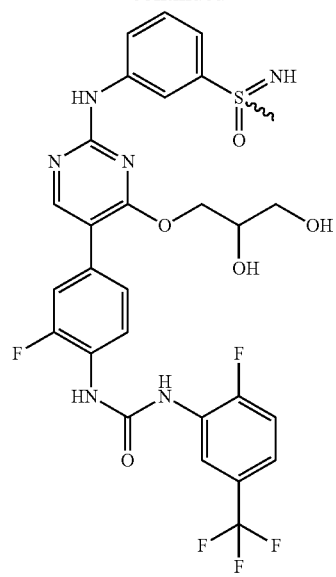
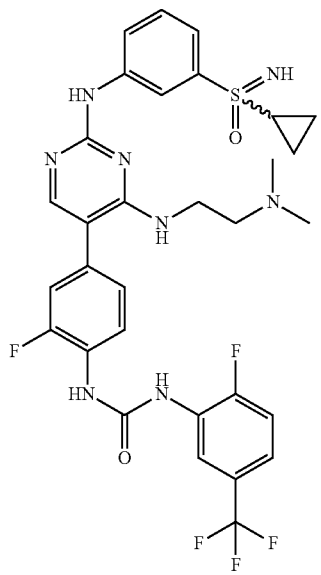
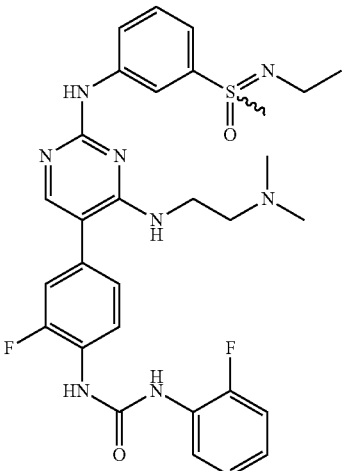

-continued

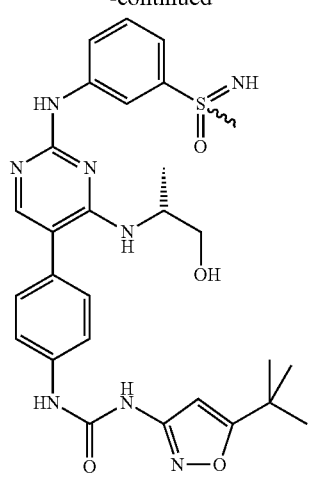

16. A compound according to claim 1, wherein heterocycloalkyl is, in each case, oxyranyl, oxetanyl, aziridinyl, azetidinyl, tetrahydrofuranyl, pyrrolidinyl, morpholinyl, dithianyl, thiomorpholinyl, piperazinyl, trithianyl or chinuclidinyl.

17. A compound according to claim 1, wherein heteroaryl is, in each case, thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl, benzofuranyl, benzothienyl, benzoxazolyl, benzimidazolyl, benzotriazolyl, indazolyl, indolyl, isoindolyl, pyridyl, pyridazinyl, pyrimidinyl, pyrazinyl, triazinyl, quinolinyl, isoquinolinyl, azocinyl, indolizinyl, purinyl, cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl.

18. A method of preparing a compound according to claim 1, wherein said method comprises:

reacting an intermediate compound of formula 5:

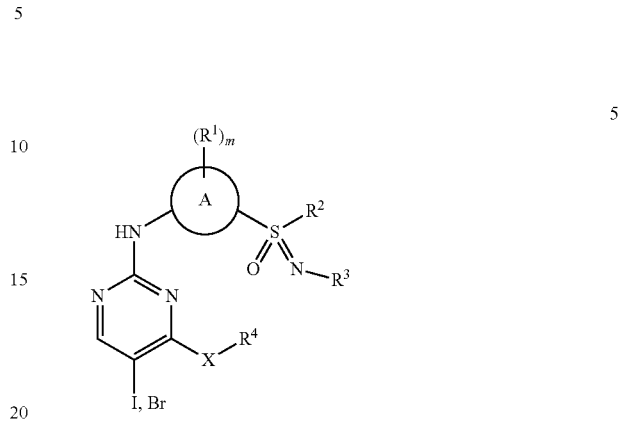

5 with an intermediate of formula 6:

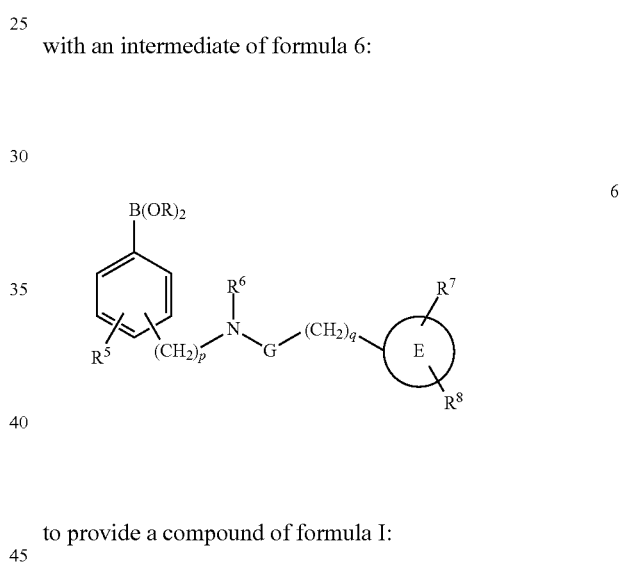

6 to provide a compound of formula I:

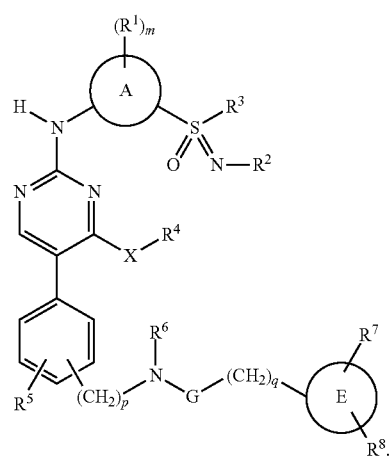

I

19. A method of preparing a compound according to claim 1, wherein said method comprises:

reacting an intermediate compound of formula I':

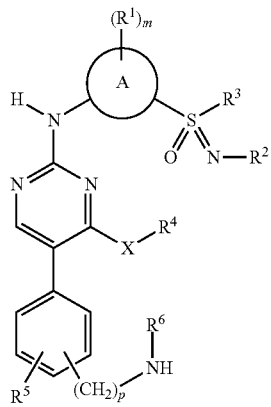

I' with an intermediate of formula 14a:

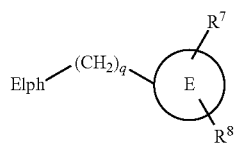

14a to provide a compound of formula I:

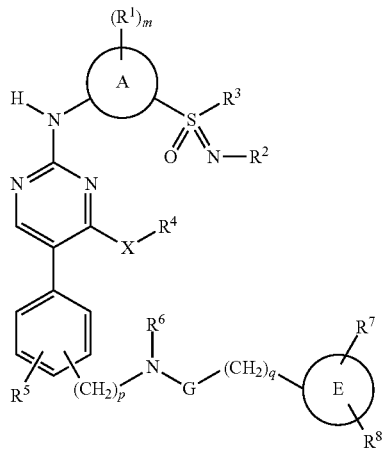

I wherein Elph is an electrophilic group suitable to act as a precursor of G.

20. A method of preparing a compound according to claim 1, wherein said method comprises:

reacting an intermediate compound of formula Ib

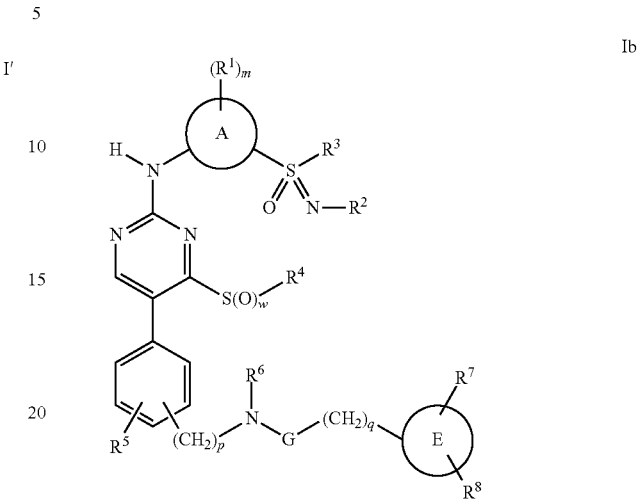

Ib wherein
w is 1 or 2,
$R^4$ forms, together with the —S(O)$_w$— to which it is attached, a leaving group, with an intermediate of formula 7a:

$$HXR^4 \qquad 7a,$$

to provide a compound of formula I:

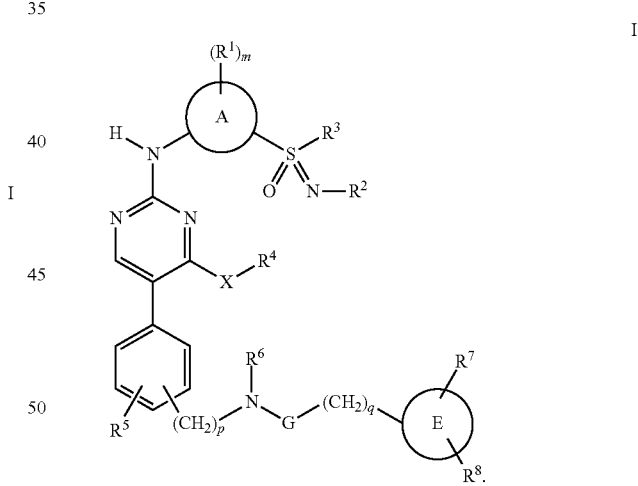

I

21. A method according to claim 19, wherein Elph is HOC(O)—Y—, ClS(O)$_2$—, or OCN—.

22. A method according to claim 20, wherein $R^4$ is —C$_1$-C$_6$-alkyl or —(CH$_2$)$_u$-aryl.

23. A pharmaceutical composition comprising a compound according to claims 1 and a pharmaceutically-acceptable diluent or carrier.

* * * * *

UNITED STATES PATENT AND TRADEMARK OFFICE
CERTIFICATE OF CORRECTION

| | |
|---|---|
| PATENT NO. | : 8,003,655 B2 |
| APPLICATION NO. | : 11/776231 |
| DATED | : August 23, 2011 |
| INVENTOR(S) | : Ingo Hartung et al. |

It is certified that error appears in the above-identified patent and that said Letters Patent is hereby corrected as shown below:

Column 124, Line 20 reads: "other, by halogen, nitro, cyano, -$C_1$-$C_6$-alkyl, or -$C_1$-" should read -- other, by halogen, nitro, cyano, -$C_1$-$C_6$-alkyl, -$OR^{11b}$, $NR^{11b}R^{12b}$, or -$C_1$- --.

Signed and Sealed this
Third Day of January, 2012

David J. Kappos
*Director of the United States Patent and Trademark Office*